United States Patent
Phelan et al.

(10) Patent No.: US 12,416,043 B2
(45) Date of Patent: Sep. 16, 2025

(54) PARALLELIZED SAMPLE PROCESSING AND LIBRARY PREP

(71) Applicant: Fluidigm Corporation, South San Francisco, CA (US)

(72) Inventors: Michael L. Phelan, South San Francisco, CA (US); Christopher J. Kubu, South San Francisco, CA (US); Brian Fowler, San Mateo, CA (US); Gang Sun, Cupertino, CA (US); Nikita Patel, San Bruno, CA (US); Naveen Ramalingam, Foster City, CA (US)

(73) Assignee: STANDARD BIOTOOLS INC., South San Francisco, CA (US)

( * ) Notice: Subject to any disclaimer, the term of this patent is extended or adjusted under 35 U.S.C. 154(b) by 945 days.

(21) Appl. No.: 17/333,792

(22) Filed: May 28, 2021

(65) Prior Publication Data
US 2022/0017953 A1   Jan. 20, 2022

Related U.S. Application Data

(63) Continuation-in-part of application No. 17/181,966, filed on Feb. 22, 2021, now Pat. No. 12,097,501.

(60) Provisional application No. 63/049,998, filed on Jul. 9, 2020, provisional application No. 62/979,832, filed on Feb. 21, 2020, provisional application No. 62/979,209, filed on Feb. 20, 2020.

(51) Int. Cl.
*C12Q 1/6851* (2018.01)
*C12Q 1/6806* (2018.01)
*C12Q 1/70* (2006.01)

(52) U.S. Cl.
CPC ......... *C12Q 1/6851* (2013.01); *C12Q 1/6806* (2013.01); *C12Q 1/70* (2013.01)

(58) Field of Classification Search
CPC ...... C12Q 1/6806; C12Q 1/6851; C12Q 1/70; C12Q 1/686; C12Q 2535/125; C12Q 2537/143; C12Q 2565/629
See application file for complete search history.

(56) References Cited

U.S. PATENT DOCUMENTS

| | | | |
|---|---|---|---|
| 6,605,451 B1* | 8/2003 | Marmaro | C12Q 1/6844 435/6.12 |
| 7,351,376 B1 | 4/2008 | Quake et al. | |
| 7,601,270 B1 | 10/2009 | Unger et al. | |
| 7,691,333 B2 | 4/2010 | McBride et al. | |
| 7,766,055 B2 | 8/2010 | Unger et al. | |
| 8,157,434 B2 | 4/2012 | Cohen et al. | |
| 8,420,017 B2 | 4/2013 | Jones et al. | |
| 9,205,468 B2 | 12/2015 | Wang et al. | |
| 9,429,500 B2 | 8/2016 | Fow et al. | |
| 9,714,443 B2 | 7/2017 | Maerkl et al. | |
| 12,097,501 B2 | 9/2024 | Phelan et al. | |
| 2005/0003361 A1 | 1/2005 | Fredriksson | |
| 2006/0051353 A1* | 3/2006 | Colombel | C07K 16/241 435/6.16 |
| 2008/0088952 A1 | 4/2008 | Unger et al. | |
| 2008/0129736 A1 | 6/2008 | Sun et al. | |
| 2010/0120038 A1 | 5/2010 | Mir | |
| 2010/0230613 A1 | 9/2010 | Pieprzyk et al. | |
| 2012/0261007 A1 | 10/2012 | Pieprzyk et al. | |
| 2013/0296196 A1* | 11/2013 | Fowler | C12P 19/34 435/6.12 |
| 2013/0302883 A1 | 11/2013 | Fowler et al. | |
| 2014/0193896 A1 | 7/2014 | Cohen | |
| 2015/0024436 A1 | 1/2015 | Eberhart et al. | |
| 2015/0132743 A1 | 5/2015 | Egidio | |
| 2015/0276089 A1 | 10/2015 | Unger et al. | |
| 2016/0024557 A1 | 1/2016 | Jones | |
| 2016/0153026 A1 | 6/2016 | Livak et al. | |

OTHER PUBLICATIONS

Lau et al., "A real-time PCR for SARS-coronavirus incorporating target gene pre-amplification," Biochemical and Biophysical Research Communications, vol. 312, pp. 1290-12196. (Year: 2003).*
Jiang et al., "A novel asymmetric and competitive allele specific real-time fluorescent PCR with MGB universal probes for detection of SNPs and point mutations," Int. J. Clin. Med., vol. 10, No. 7, pp. 10411-10421. (Year: 2017).*
Mattarucchi et al., "Different Real Time PCR Approaches for the Fine Quantification of SNP's Alleles in DNA Pools: Assays Development, Characterization and Pre-validation," Journal of Biochemistry and Molecular Biology, September, vol. 38, No. 5, pp. 555-562. (Year: 2005).*
Final Office Action for U.S. Appl. No. 17/181,966 mailed Jul. 24, 2023, all pages.
International Application No. PCT/US2021/019101 received an International Search Report and Written Opinion mailed Jun. 23, 2021, 13 pages.
International Application No. PCT/US2021/019101 received Invitation to Pay Additional Fees mailed Apr. 16, 2021, 3 pages.
U.S. Appl. No. 17/181,966, Notice of Allowance, Mailed on May 14, 2024, 9 pages.
Application No. EP21757384.9 , Extended European Search Report, Mailed on Feb. 21, 2024, 7 pages.
Canadian Application No. CA3,168,563 , Office Action, Mailed on Jan. 23, 2025, 4 pages.
Japanese Application No. JP2022-549901, Office Action Mailed On Apr. 25, 2025, 7 pages.

* cited by examiner

*Primary Examiner* — Young J Kim
(74) *Attorney, Agent, or Firm* — Kilpatrick Townsend & Stockton LLP

(57) ABSTRACT

Described herein are methods, kits and systems for sample enrichment, multi-step library preparation, sample normalization, detection of sample biomolecules and combinations thereof. Enrichment and multi-step library preparation is described in the context of microfluidic workflows. Sample barcoding methods and kits are described for increasing sample throughput while reducing background in negative samples. Integrated microfluidic devices comprising sample processing unit cells coupled to an array of reaction sites are provided for integrated workflows.

27 Claims, 31 Drawing Sheets

Barcoded multiplex pooling method significantly improve the pooling efficiency over the simple Dorfman pooling method.

PARALLELIZED SAMPLE PROCESSING AND LIBRARY PREP

CROSS-REFERENCES TO RELATED APPLICATIONS

This application is a Continuation in Part of U.S. patent application Ser. No. 17/181,966, filed Feb. 22, 2021, which claims the benefit of priority to U.S. Provisional Application No. 63/049,998, filed Jul. 9, 2020; U.S. Provisional Application No. 62/979,832, filed Feb. 21, 2020; and U.S. Provisional Application No. 62/979,209, filed Feb. 20, 2020, the entire contents of all of which are incorporated herein by reference for all purposes.

BACKGROUND

Automated microfluidic systems and/or parallel library preparation of samples can reduce labor, reagent use, and variability in sample processing. These benefits are further improved by sample indexing (barcoding), which allows samples processed in parallel to be combined prior to sequencing or detection by qPCR. In additional, a more fully integrated microfluidic workflow would reduce hands-on time and human error.

SUMMARY

As described herein, an integrated microfluidic device may therefore include, an array of reaction sites and a plurality of sample processing unit cells including a plurality of sample processing sites, wherein the unit cell is in fluidic communication with a plurality of different reagent inlets, and wherein sample inlets to the array are downstream of the plurality of sample processing sites of the plurality of unit cells.

The plurality of reagent inlets may share a common channel to each unit cell. The microfluidic device may include a multiplexor configured to control which reagent inlet is used to load a processing site of the unit cell.

The plurality of sample processing sites may include a plurality of loops and/or chambers. Each unit cell further includes one or more of a sample inlet channel, a waste outlet channel, additional reagent inlets, and/or additional columns.

Each unit cells may include a plurality of valves configured to control the unit cell. The plurality of valves may be configured to deliver sample and reagents to different locations in the unit cell. The plurality of valves may be configured to place sample processing locations in isolation or in communication with one another. The plurality of valves may be configured to drive mixing at different locations. The plurality of valves are configured to direct flow of sample or reagents solution out of the unit cell For example, the unit cell includes a peristaltic pump (e.g., defined by a set of valves in series).

Wherein individual unit cells further includes at least one column configured to retain beads. The column may include a sieve architecture providing a plurality of openings through which fluid may flow but beads larger than the outlet opening may be retained.

In certain aspects, an integrated microfluidic device may include: an array of reaction sites; and a plurality of sample processing unit cells including a plurality of sample processing sites, wherein the unit cell is in fluidic communication with a plurality of different reagent inlets; wherein sample inlets to the array are downstream of the plurality of sample processing sites of the plurality of unit cells.

A method may include loading beads into a column of a unit cell and capturing sample (i.e., biomolecules of a sample such as proteins, antibodies, RNA, viral particles, etc.) on the bead (e.g., before or after loading the beads into the column). As discussed herein, the bead may include (e.g., present on its surface) one or more of a protein (e.g., an antibody, such as an antibody to a target serum protein or viral antigen) and oligonucleotide (e.g., that hybridizes to target RNA, such as a viral RNA). Additional steps may include washing beads, such that a wash buffer flows over the beads in the column and into a waste outlet. Optionally a reporter, such as an oligonucleotide-conjugated antibody that binds to target biomolecules or a oligonucleotide probe that hybridizes to target biomolecules may be flowed over the beads. Additional steps may include eluting from the beads, such as by flowing an elution buffer over the beads in the column and optionally further cycling the elution buffer across the beads such as by passing the buffer around a loop using a peristaltic pump.

In certain aspects, a method of detecting the presence of at least one of a plurality of alleles of a gene in a sample may include the steps of: preamplifying a gene by PCR to obtain a preamplified sample such that a plurality of alleles of the gene would be amplified by the same preamplification primer pair; separating the preamplified sample into a plurality of reaction sites; and detecting a cycle threshold (CT) of each of the plurality of alleles in a separate reaction site of the plurality of reaction sites, wherein detection is by qPCR and wherein each allele is specifically amplified with a different allele-specific primer pair. The method may further include step d) of identifying the presence of an allele in the sample based on a difference in the CT values (dCT) of the allele and another allele of the plurality of alleles, or any other aspects described further herein. One or more of the steps may be performed on a microfluidic device, such as an array or integrated microfluidic device as described further herein. Aspects also include kits for detecting the presence of at least on of a plurality of alleles of a gene, as described further herein.

Sample barcoding for multiplexing may increase sample throughput but the leftover primers (e.g., from sample with little or no target) may create crosstalk, leading to a false positive and/or higher background. Discussed herein are methods and kits for reducing such crosstalk.

In certain aspects, an assay method for detecting at least one target nucleic acid in a plurality of samples includes:
  a) reverse transcribing and preamplifying a target nucleotide sequence in each of S separate samples to produce a tagged target nucleotide sequence from each sample, wherein at least one of the S samples includes the target nucleotide sequence, wherein the tagged target nucleotide sequence includes a sample tag and a target nucleotide sequence,
     wherein preamplifying is with a tagged target-specific primer that includes a sample tag and a target-specific sequence, and
     wherein the target-specific sequence hybridizes to a portion of the target nucleotide sequence;
  b) mixing the tagged target nucleotide sequences of each of the S samples to produce a mixture of tagged target nucleotide sequences;
  c) splitting the mixture into a plurality of reaction sites;
  d) adding different primer pairs to each reaction sites;
  e) amplifying the tagged target nucleotide sequence from a different sample in each reaction site, wherein each different primer pair includes a primer that hybridizes to a different sample tag; and/or f) detecting the presence of the of the amplified tagged target nucleic acid by qPCR with a fluorescent target-specific probe that includes at least a portion of the target-specific sequence but does not include a sample tag; wherein step e of amplifying is in the presence of the target-specific probe.

More generally, an assay method for detecting at least one target nucleic acid in a plurality of samples may include:

a) separately subjecting each of S samples to an encoding reaction that produces a tagged target nucleotide sequence using at least one tagged target-specific primer, wherein at least one of the S samples includes the target nucleotide sequence and wherein the tagged target nucleotide sequence includes a sample tag and a target nucleotide sequence;

b) mixing the tagged target nucleotide sequences of each of the S samples to produce a mixture of tagged target nucleotide sequences;

c) splitting the mixture into a plurality of reaction sites;

d) adding different primer pairs to different reaction sites, wherein each different primer pair includes a primer that hybridizes to a different sample tag to amplify a tagged target nucleotide sequence from a specific sample;

e) amplifying the tagged target nucleotide sequence from the at least one of the S samples in the presence of a target-specific probe, wherein the target-specific probe includes a sequence identical to at least a portion of a target-specific sequence of the target-specific primer but does not include a sample tag; and/or f) detecting the presence of the tagged target nucleotide.

An assay method for detecting at least one target nucleic acid in a plurality of samples may include:

a) separately subjecting each of S samples to an encoding reaction that produces a tagged target nucleotide sequence using at least one tagged target-specific primer, wherein at least one of the S samples includes the target nucleotide sequence and wherein the tagged target nucleotide sequence includes a sample tag and a target nucleotide sequence;

b) mixing the tagged target nucleotide sequences of each of the S samples to produce a mixture of tagged target nucleotide sequences;

c) amplifying the tagged target nucleotide sequence from the at least one of the S samples in the presence of a target-specific probe, wherein the target-specific probe includes a sequence identical to at least a portion of a target-specific sequence of the target-specific primer but does not include a sample tag; and/or d) detecting the presence of the tagged target nucleotide. Also described herein are kits for performing any of the methods described herein.

Aspects of the subject application also include methods, kits and devices for parallel processing of samples, such as for library preparation and/or normalization.

In some embodiments, a method of library normalization includes one or more of:

a. obtaining aliquots from a plurality of samples, wherein samples polynucleotides have spaced inverted repeats;

b. performing suppression PCR on the aliquots of step a;

c. quantifying amplification products from step b;

d. pooling the plurality of samples to form a library normalized based on the quantification of step c; and/or wherein the pooled plurality of samples have not undergone the suppression PCR of step b.

Methods of the above embodiments may further include aspects of sample type, sample number, suppression PCR, polynucleotide characteristics, sample enrichment and/or preparation, primers, sample quantitation and/or normalization, microfluidic devices, metrics of improvement, and/or sequencing applications as described herein.

In some embodiments, a kit for library quantification of polynucleotides by suppression qPCR may include a primer including a sequence identical to at least 8 nucleotides of one of the inverted repeats of another polynucleotide in the kit, such as a library quantification standard having spaced inverted repeats separated by at least 150 nucleotides.

In some embodiments, a kit for library preparation and quantification may include adaptors (or primers) together providing an inverted repeat at least 8 nucleotides in length (e.g., capable of producing polynucleotides with inverted repeats flanking inserts); and/or a primer including a sequence identical to at least 8 nucleotides of an inverted repeat.

Kits of any of the above embodiments may further include, or provide support for performing methods that include, a sample type, sample number, reagents for suppression PCR, polynucleotide characteristics, reagent for sample enrichment and/or preparation, primers, reagents for sample quantitation and/or normalization, microfluidic devices, metrics of improvement, and/or sequencing applications as described herein. Kits may include beads, microfluidic devices, reverse transcription reagents, primers and/or master mix for PCR (such as suppression PCR) reagents, dye (such as a passive reference dye).

In general, aspects of the subject application may include one or more of: a kit for performing any of the method aspects above, a method of library normalization based on suppression qPCR, a method of suppression qPCR, a method of sequencing a library normalized by suppression qPCR, and/or a pool of samples normalized based on suppression qPCR of any of the method aspects above.

In certain aspects, a method of parallel sample processing includes splint ligation in which a target nucleic acid is the splint template.

For example, a method of processing a splint hybridization product may include hybridizing a first probe and a second probe to a target nucleic acid to form a hybridization product, where a 3'-OH end of the first probe adjacent to a 5'-PO4 end of the second probe. At least one of the first probe and the second probe comprises a binding moiety. The method may further include capturing the hybridization product by specifically binding the binding moiety to a solid support.

In another example, a method of detecting a splint ligation product may include, hybridizing a first probe and a second probe to a target nucleic acid to form a hybridization product, wherein a 3'-OH end of the first probe is adjacent to a 5'-PO4 end of the second probe. The method may further include ligating the first probe and second probes to form a ligation product. The method may further include detecting the presence of the ligation product.

Hybridization product or ligation product may be captured on a solid support (e.g., beads such as beads in a column of a microfluidic device) as described further herein. Splint ligation probes may comprise one or more sample barcode sequences, allowing for pooling of samples, processing of samples together (e.g., capture, ligation and/or preamplification) prior to splitting the pool and separately detecting ligation products of different samples (e.g., on an array IFC). The target nucleic acid may be DNA or an RNA, such as a viral genomic RNA (or any viral gene) or a mammalian gene transcript.

In certain aspects, a kit for parallel sample process may include reagent for splint ligation methods described herein. Such a kit may have two splint ligation probes described in any embodiments herein, and may optionally further comprise ligase for forming ligation products, primers for amplifying ligation products, and/or additional reagents such as reagents for separating ligation product from solid support. Splinted ligation kits may further include one or more microfluidic devices described herein.

BRIEF DESCRIPTION OF THE FIGURES

FIG. 2A shows the device itself, an 48.Atlas IFC (Fluidigm). FIG. 2B shows the device overlaid with markings indicating sample inlets 204, sample barcode reagent inlets 206, common reagent inlets 208, wash solution inlets 210, as well as waste outlets 212. Inlets can be loaded onto the microfluidic through backpressure applied by a pneumatic system (controller). Control ports 214 are also marked, and can be pressurized by the pneumatic system to operate elastomeric valves on the device to direct flow and fluidic communication. A substrate underlying the microfluidic circuit thermally couples to a thermocycler.

DETAILED DESCRIPTION

Figure 1:
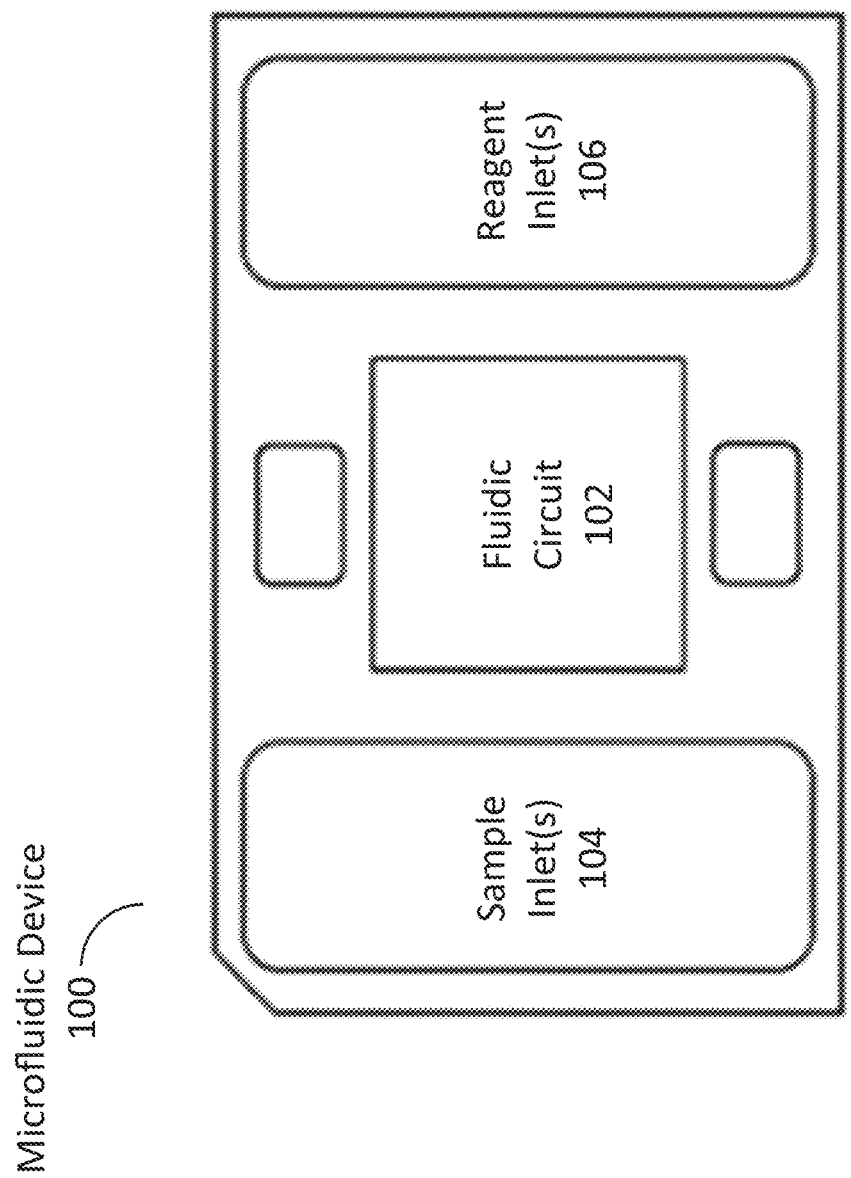
FIG. 1 is an abstraction of a microfluidic device 100 having at least sample inlet(s) 104 and reagent inlet(s) 106 that feed into a fluidic circuit 102. Such a device may perform sample preparation steps described herein. The device may include additional inlets and outlets.

Methods, microfluidic systems and kits for sample preparation, including library preparation and normalization, are provided herein. Some embodiments may provide for specific sequencing applications including mRNA sequencing applications or DNA sequencing applications described herein.

The methods, systems, and kits may include microfluidic devices and/or controllers for enrichment and multi-step sample preparation.

Definitions

The terms used in this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The term "molecule" means any distinct or distinguishable structural unit of matter comprising one or more atoms, and includes for example polypeptides and polynucleotides.

The term "polymer" means any substance or compound that is composed of two or more building blocks ('mers') that are repetitively linked to each other. For example, a "dimer" is a compound in which two building blocks have been joined together.

The term "polynucleotide" (also referred to as oligonucleotides) as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages. In the context of a sample for library normalization, a polynucleotide may refer to a sample indexed (or barcoded) polynucleotide. Such a polynucleotide may also have sequencing adaptors flanking an "insert" sequence derived from mRNA or gDNA.

Thus, a "polynucleotide" or "nucleotide sequence" is a series of nucleotide bases (also called "nucleotides") generally in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

"DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases, that are linked together on a ribose sugar backbone. RNA typically has one strand of nucleotide bases.

A "polypeptide" or "protein" (one or more peptides) is a chain of chemical building blocks called amino acids that are linked together by chemical bonds called peptide bonds. A protein or polypeptide, including an enzyme, may be "native" or "wild-type", meaning that it occurs in nature; or it may be a "mutant", "variant" or "modified", meaning that it has been made, altered, derived, or is in some way different or changed from a native protein, or from another mutant.

A "probe" in the context of an oligonucleotide reaction (e.g., encoding reaction, reverse transcription, amplification, and so forth) refers simply to an oligonucleotide sequence that binds to (hybridizes) a target. Described herein are splint ligation probes and competition probes do not necessarily provide a signal when bound to a target nucleotide sequence. However, qPCR probes, or probes described as having a fluorophore (or fluorophore and quencher), may be used to detect a target.

A "sample biomolecule of interest" is a target, often a specific oligonucleotide or protein, that may be specifically bound, processed and/or detected in an assay as described herein.

The term "flow" means any movement of liquid or solid through a device or in a method of the invention, and encompasses without limitation any fluid stream, and any material moving with, within or against the stream, whether or not the material is carried by the stream. For example, the movement of molecules or cells through a device or in a method of the invention, e.g. through channels of a microfluidic chip of the invention, comprises a flow. This is so, according to the invention, whether or not the molecules or cells are carried by a stream of fluid also comprising a flow, or whether the molecules or cells are caused to move by some other direct or indirect force or motivation, and whether or not the nature of any motivating force is known or understood. The application of any force may be used to provide a flow, including without limitation, pressure, capillary action, electroosmosis, electrophoresis, dielectrophoresis, optical tweezers, and combinations thereof, without regard for any particular theory or mechanism of action, so long as molecules or cells are directed for detection, measurement or sorting according to the invention.

An "inlet region" is an area of a microfabricated chip that receives molecules or cells for detection measurement or sorting. The inlet region may contain an inlet channel, a well or reservoir, an opening, and other features which facilitate the entry of molecules or cells into the device. A chip may contain more than one inlet region if desired. The inlet region is in fluid communication with the main channel and is upstream therefrom.

An "outlet region" is an area of a microfabricated chip that collects or dispenses molecules or cells after detection, measurement or sorting. An outlet region is downstream from a discrimination region, and may contain branch channels or outlet channels. A chip may contain more than one outlet region if desired.

A "loop" or "sample processing loop" is a looped channel that may be operated (e.g., by dilation pumping or peristaltic pumping) to mix solution in the loop. Loops may be dynamic, such that valves are operated to define loops and put different chambers in communication with one another. The loop may have any shape. The channel or channels comprising a loop may have or cooperate with pumps and/or valves to open and close the loop, and/or to provide or drain contents to and from the loop. In certain embodiments, the loop can be isolated or closed from other channels in a microfluidic device. Also in certain embodiments, fluid can be circulated in the loop, for example by providing a peristaltic pump comprising three or more microvalves.

In certain embodiments, a "circulation loop" is located within the chip, typically in or communicating with a unit cell, in which a fluid (e.g. the flow of a biological sample) is circulated. The circulation loop may comprise a "hybridization loop" or "target loop" in which the flow is directed past a series of targets or probes (e.g. DNA or proteins) that are in or exposed to the loop and its contents, such as in a column. For example, probes may be patterned on the surface of a substrate or beads, e.g. a solid substrate and also called a "probe substrate".

A "detection region" is a location within the chip, typically in or coincident with the main channel (or a portion thereof) and/or in or coincident with a detection loop, where molecules or cells to be identified, characterized, hybridized, measured, analysed or sorted (etc.), are examined on the basis of a predetermined characteristic. In a preferred embodiment, molecules or cells are examined one at a time. In other preferred embodiments, molecules, cells or samples are examined together, for example in groups, in arrays, in rapid, simultaneous or contemporaneous serial or parallel arrangements, or by affinity chromatography. In one such embodiment, a sample is exposed to probes in detection region, preferably probes having a predetermined pattern within or coincident with a detection region, e.g. a target hybridization or detection loop. Preferably, the molecule or cell characteristic is detected or measured optically, for example, by testing for the presence or amount of a reporter. For example, the detection region is in communication with one or more microscopes, diodes, light stimulating devices, (e.g., lasers), photomultiplier tubes, and processors (e.g., computers and software), and combinations thereof, which cooperate to detect a signal representative of a characteristic, marker, or reporter, and to determine and direct the measurement or the sorting action at the discrimination region. In sorting embodiments, the detection region is in fluid communication with a discrimination region and is at, proximate to, or upstream of the discrimination region.

A "discrimination region" or "branch point" is a junction of a channel where the flow of molecules or cells can change direction to enter one or more other channels, e.g., a branch channel, depending on a signal received in connection with an examination in the detection region. Typically, a discrimination region is monitored and/or under the control of a detection region, and therefore a discrimination region may "correspond" to such detection region. The discrimination region is in communication with and is influenced by one or more sorting techniques or flow control systems, e.g., electric, electro-osmotic, (micro-) valve, etc. A flow control system can employ a variety of sorting techniques to change or direct the flow of molecules or cells into a predetermined branch channel.

A "branch channel" is a channel which is in communication with a discrimination region and a main channel. Typically, a branch channel receives molecules or cells depending on the molecule or cell characteristic of interest as detected by the detection region and sorted at the discrimination region. A branch channel may be in communication with other channels to permit additional sorting. Alternatively, a branch channel may also have an outlet region and/or terminate with a well or reservoir to allow collection or disposal of the molecules or cells.

A "gene" is a sequence of nucleotides which code for a functional polypeptide. For the purposes of the invention a gene includes an mRNA sequence which may be found in the cell. For example, measuring gene expression levels according to the invention may correspond to measuring mRNA levels. "Genomic sequences" are the total set of genes in an organism. The term "genome" denotes the coding sequences of the total genome.

Polynucleotides may "hybridize" to each other when at least one strand of one polynucleotide can anneal to another polynucleotide under desired or defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences. (1×SSC is 0.15 M NaCl, 0.015 M Na citrate.) Polynucleotide sequences that "hybridize" to the polynucleotides herein may be of any length. In one embodiment, such polynucleotide sequences are at least 10, at least 15, or at least 20 nucleotides long.

A sample "barcode", "tag" or "index" as used herein may be interchangeable. In the context of an encoding reaction, such as with sample tagged (i.e., barcoded) primers, a tag (i.e., barcode) is a sequence identifying a sample, such that the sample may thereafter be pooled with other samples while still identifying reaction products that came from each sample. As such, a sample tagged primer comprises a sequence identifying the sample it amplifies a target nucleotide sequence from. For example, sequencing can read the sample tags (i.e., indexes) to identify which sample a target read came from. Aspects of the application include selective amplification of sample tagged nucleotide sequences, such as by qPCR using at least one primer to a sample tag (that hybridizes a sample tag sequence).

An "identical sequence" means sequences, usually 6 nucleotides or longer, which is identical to one another. When one sequence is of a oligonucleotide such as a target nucleotide sequence that has been amplified, either strand may be considered when determining if the sequence is identical (e.g., to a primer or probe).

Sample

In certain aspects, at least 8, 12, 24, 48, 96, or 384 samples are processed by the subject methods or kits. Samples may be from any biological source, such as eukaryotic sample (e.g., human, primate, rodent) or a bacterial sample. Samples may have biomolecules of interest, such as nucleic acids (e.g., polynucleotides) described herein. Samples may be derived from a cell sample, such as a tissue sample or cell culture. In certain aspects, samples may have been derived from a fixed tissue (e.g., solid tissue or cells). In certain aspects, fixed tissue (such as FFPE tissue) may have undergone fragmentation (e.g., of RNA) and be of variable quality that would result in variable sequencing depth. In certain aspects, such as when a target biomolecule is a biomarker or a viral antigen, the sample may comprise a blood sample (e.g., serum, plasma or whole blood), a saliva sample, or a nasal swab. Nucleic acids may be present in the sample in the absence or a minimal amount of protein. Aspects include providing or producing sample libraries in which sample polynucleotides are at least partially prepared for sequencing, such as by addition of sequencing adaptors.

Sequencing Technologies

Some embodiments may provide for specific sequencing applications including mRNA sequencing applications (such targeted RNA-seq, 3' RNA-seq, full-length RNA sequencing) or DNA sequencing applications (such as whole genome sequencing (WGS), targeted resequencing, chromatin immunoprecipitation (ChIP) sequencing, RNA immunoprecipitation (RIP-Seq), chromatin accessibility sequencing (ATAC-seq)) and epigenetics such as methylation sequencing (bisulfite sequencing). Any suitable sequencing technique discussed herein or known in the art is within the scope of the subject application.

Certain sequencing methods, and corresponding library preparation workflows, are known in the art, including workflows that allow for sample barcoding (e.g., through dual indexing). For example, an Illumina Adapter Sequences listing published by Illumina provides adapter sequences, index sequences, and primers, for common library prep kits including Nextera kits, AmpliSeq, TruSight, and TruSeq kits. These and other sequencing methods and library prep kits are within the scope of the application, and are partially described by Slatko et al. in "Overview of next-generation sequencing technologies." Current protocols in molecular biology 122.1 (2018): e59. Current sequencing methods may be referred to herein as Next Generation Sequencing (NGS). NGS includes many sequencing by synthesis technologies, including technologies based on clonal expansion (e.g., bridge amplification in Illumina sequencing) and single molecule sequencing technologies.

Sequencing Library Preparation and Applications

As used herein, library preparation generally refers to preparation of a sample for sequencing. Resulting polynucleotides may have sequencing adapters and may be sample barcoded (indexed).

These and other library preparation methods and kits may be adapted for the subject invention, and are partially described by Head et al. in "Library construction for next-generation sequencing: Overviews and challenges" Biotechniques. 2014; 56(2): 61—passim. and described further herein.

Of note, sample preparation steps prior to library preparation are within the scope of the application, and include without limitation one or more of sample lysis, nucleic acid purification, and enrichment of a particular group of nucleic acids (such as genomic DNA (gDNA), RNA, mRNA, target mRNA, etc.). Sequencing may be of RNA or gDNA targets, such as in whole genome sequencing, whole transcriptome sequencing, target specific sequencing such as TCR/BCR sequencing, or chromatin accessibility sequencing.

Library preparation steps may include fragmentation, reverse transcription (e.g., with tailing and template switching), and addition of sequencing adaptors and/or sample barcodes (e.g., through PCR).

Additional steps include harvesting from a microfluidic device, pooling based on sample quantitation (sample normalization), depletion steps (such as of ribosomal RNA through enzymatic degradation, cleavage, hybridization, etc.), cleanup steps to remove unwanted artefacts such as short products (e.g., primer dimer), amplification of pooled sample (e.g., with p5/P7 primers), and quantification of pooled sample prior to sequencing.

Fragmentation and Library Prep

In general, the core steps in preparing RNA or DNA for NGS analysis are: (i) fragmenting and/or sizing the target sequences to a desired length, (ii) converting target to double-stranded DNA, (iii) attaching oligonucleotide adapters to the ends of target fragments, and (iv) quantitating the final library product for sequencing.

Fragmentation may be performed by heating, shearing, or enzymatically (e.g., with a DNAse, RNAase, restriction enzyme, transposase, etc.).

The size of the target DNA fragments in the final library is a key parameter for NGS library construction. Three approaches are available to fragment nucleic acid chains: physical, enzymatic, and chemical. DNA fragmentation is typically done by physical methods (i.e., acoustic shearing and sonication) or enzymatic methods (i.e., non-specific endonuclease cocktails and transposase tagmentation reactions). In our laboratory, acoustic shearing with a Covaris instrument (Covaris, Woburn, MA) is typically done to obtain DNA fragments in the 100-5000 bp range, while Covaris g-TUBEs are employed for the 6-20 Kbp range necessary for mate-pair libraries. Enzymatic methods include digestion by DNase I or Fragmentase, a two enzyme mix (New England Biolabs, Ipswich MA).

However, Fragmentase produced a greater number of artificial indels compared with the physical methods. An alternative enzymatic method for fragmenting DNA is Illumina's Nextera tagmentation technology (Illumina, San Diego, CA) in which a transposase enzyme simultaneously fragments and inserts adapter sequences into dsDNA. This method has several advantages, including reduced sample handling and preparation time.

Desired library size is determined by the desired insert size (referring to the library portion between the adapter sequences), because the length of the adaptor sequences is a constant. In turn, optimal insert size is determined by the limitations of the NGS instrumentation and by the specific sequencing application. For example, when using Illumina technology, optimal insert size is impacted by the process of cluster generation in which libraries are denatured, diluted and distributed on the two-dimensional surface of the flowcell and then amplified. While shorter products amplify more efficiently than longer products, longer library inserts generate larger, more diffuse clusters than short inserts. Optimal library size is also dictated by the sequencing application. For exome sequencing, more than 80% of human exomes are under 200 bases in length In the case of microRNA (miRNA)/small RNA library preparation, the desired product is only 20-30 bases larger than the 120 bp adaptor dimers. Therefore, it is critical to perform a gel size selection to enrich the libraries as much as possible for the desired product.

Library preparation from DNA samples for sequencing whole genomes, targeted regions within genomes (for example exome sequencing), ChIP-seq experiments, or PCR amplicons (see below) follows the same general workflow. Ultimately, for any application, the goal is to make the libraries as complex as possible (see below).

Numerous kits for making sequencing libraries from DNA are available commercially from a variety of vendors. Competition has driven prices steadily down and quality up. Kits are available for making libraries from microgram down to picogram quantities of starting material. However, one should keep in mind the general principle that more starting material means less amplification and thus better library complexity.

With the exception of Illumina's Nextera prep, library preparation may include one or more of: (i) fragmentation, (ii) end-repair, (iii) phosphorylation of the 5' prime ends, (iv) A-tailing of the 3' ends to facilitate ligation to sequencing adapters, (v) ligation of adapters, and (vi) some number of PCR cycles to enrich for product that has adapters ligated to both ends. The primary differences in an Ion Torrent workflow are the use of blunt-end ligation to different adapter sequences.

Takara's sample prep kits implement first strand synthesis, tailing and template switching. A tailed first strand is synthesized from a first primer (e.g., poly(T), target specific, or degenerate primer). An oligonucleotide with a 3' sequence complementary to the tail sequence and provides a template primer binding site incorporated into the first strand by extension. Another primer binding site may have been provided by the first primer, or can be added by PCR with another primer (e.g., poly(T), target specific, or degenerate primer). The incorporated primer binding sites can be used for subsequent PCR and incorporation of adaptors sequences (e.g., indexes, read sequences, amplification sequences, etc.).

An oligonucleotide is hybridize Amplification is performed with a primer to the tail sequence and an application specific primer, such as a randomer (N6) primer, target specific primer, poly(A) primer. Sites for amplification by primers (including adaptor sequences) are introduced by Once the starting DNA has been fragmented, the fragment ends may be blunted and 5' phosphorylated using a mixture of three enzymes: T4 polynucleotide kinase, T4 DNA polymerase, and Klenow Large Fragment. Next, the 3' ends are A-tailed using either Taq polymerase or Klenow Fragment (exo-). Taq is more efficient at A-tailing, but Klenow (exo-) can be used for applications where heating is not desired, such as preparing mate-pair libraries. During the adapter ligation reaction the optimal adapter:fragment ratio is ~10:1, calculated on the basis of copy number or molarity. Too much adapter favours formation of adapter dimers that can be difficult to separate and dominate in the subsequent PCR amplification. Bead or column-based clean-ups can be performed after end repair and A-tail reactions, but after ligation we find bead-based clean-ups are more effective at removing excess adapter dimers.

To facilitate multiplexing, different barcoded adapters can be used with each sample. Alternatively, barcodes can be introduced at the PCR amplification step by using different barcoded PCR primers to amplify different samples. High quality reagents with barcoded adapters and PCR primers are readily available in kits from many vendors. However, all the components of DNA library construction are now well documented, from adapters to enzymes, and can readily be assembled into "home-brew" library preparation kits.

An alternative method is the Nextera DNA Sample Prep Kit (Illumina), which prepares genomic DNA libraries by using a transposase enzyme to simultaneously fragment and tag DNA in a single-tube reaction termed "tagmentation". The engineered enzyme has dual activity; it fragments the DNA and simultaneously adds specific adapters to both ends of the fragments. These adapter sequences are used to amplify the insert DNA by PCR. The PCR reaction also adds index (barcode) sequences. The preparation procedure improves on traditional protocols by combining DNA fragmentation, end-repair, and adaptor-ligation into a single step. This protocol is very sensitive to the amount of DNA input compared with mechanical fragmentation methods. In order to obtain transposition events separated by the appropriate distances, the ratio of transposase complexes to sample DNA is critical. Because the fragment size is also dependent on the reaction efficiency, all reaction parameters, such as temperatures and reaction time, are critical and must be tightly controlled.

RNA Sequencing Library Prep

It is important to consider the primary objective of an RNA sequencing experiment before making a decision on the best library protocol. If the objective is discovery of complex and global transcriptional events, the library should capture the entire transcriptome, including coding, noncoding, anti-sense and intergenic RNAs, with as much integrity as possible. However, in many cases the objective is to study only the coding mRNA transcripts that are translated into the proteins. Yet another objective might be to profile only small RNAs, most commonly miRNA, but also small nucleolar RNA (snoRNA), piwi-interacting RNA (piRNA), small nuclear RNA (snRNA), and transfer RNA (tRNA). While we will endeavour to describe the principles of RNA sequencing libraries in this review, it is not possible to explain all of the different protocols available. Interested readers should research the many options themselves.

One major limitation in miRNA library construction arises when the amount of input RNA is low (e.g., <200 ng total RNA); short adapter dimers compete in the RT-PCR reaction with the desired product, adapters, and miRNA inserts. When too many adapter dimers are present they stream up the gel during the size selection step and contaminate the product bands.

For mRNA sequencing libraries, methods have been developed based on cDNA synthesis (reverse transcription) using random primers, oligo-dT primers, or by attaching adapters to mRNA fragments followed by some form of amplification. mRNA can be primed by random oligomers or by an anchored oligo-dT to generate first strand cDNA. If random priming is used, the rRNA must first be removed or reduced. rRNA can be removed using oligonucleotide probe-based reagents, such as Ribo-Zero (Epicenter, Madison, WI) and RiboMinus (Life Technologies, Carlsbad, CA). Alternatively, poly-adenylated RNA can be positively selected using oligo-dT beads. Such poly-A tail may be added by end repair (e.g., A-tailing enzyme) to enable capture of short or fragmented RNA. Alternatively or in addition, a bead may comprise oligonucleotides that specifically hybridize to one or more target nucleic acids, such as TCR and/or BCR sequences. Alternatively or in addition, a bead may comprise oligonucleotides that specifically hybridize to one or more target nucleic acids, such as TCR and/or BCR sequences. Alternatively or in addition, target specific probes may hybridize to one or more target nucleic acids, such as TCR and/or BCR sequences, and said probes may comprise binding moieties that enable specific binding by beads.

It is often desirable to create libraries that retain the strand orientation of the original RNA targets. For example, in some cases transcription creates anti-sense RNA constructs that may play a role in regulating gene expression. In fact, long noncoding RNA (lncRNA) analysis depends on directional RNA sequencing. Methods for preparing directional RNA-seq libraries are readily available. The concept is to perform the cDNA reaction and remove one of the two strands selectively, by incorporating dUTP into the second strand cDNA synthesis reaction. The uracil-containing strand can then be removed enzymatically (NEBNext Ultra Directional RNA Library Prep Kit for Illumina) or prevented from further amplification with a PCR polymerase that cannot recognize uracil in the template strand (Illumina TruSeq Stranded Total RNA kit). In addition, actinomycin D is frequently added to the first strand cDNA synthesis reaction to reduce spurious antisense synthesis during the first strand synthesis reaction.

An alternative and hybrid method utilizes random or anchored oligo-dT primers with an adapter sequence on the 5' end of the primer to initiate first strand cDNA synthesis. Next, in a procedure called template switching (shown in FIG. 4B), a 3' adapter sequence is added to the cDNA molecule. This method has a distinct advantage in that the first strand cDNA molecule can be PCR amplified directly without second strand synthesis using the unique sequence tag put on the 3' end by the template switching reaction. A 5' unique sequence tag is also introduced by standard priming in the first strand synthesis.

Targeted DNA Sequencing

Targeted sequencing allows investigators to study a selected set of genes or specific genomic elements; for example, CpG islands and promoter/enhancer regions. A common application of targeted sequencing is exome sequencing and high quality kits are commercially available; SureSelect (Agilent Technologies), SeqCap (Roche NimbleGen, Madison, WI) and TruSeq Exome Enrichment Kit (Illumina). All three capture methods are based on probe hybridization to enrich sequencing libraries made from whole genome samples. Life Technologies has commercialized an alternative approach based on highly multiplexed, PCR-based AmpliSeq technology. There are options to customize all these products and investigators can design capture or PCR probes for target regions covering from thousands to millions of bases within a genome.

Hybridization capture approaches generally work well but can suffer from off-target capture and struggle to effectively capture sequences with high levels of repetition or low complexity (i.e., the Human Histocompatibility Locus region). The PCR-based AmpliSeq method is more efficient with lower amounts of DNA. It should also be noted that probes are based on a reference sequence, and variations that substantially deviate from the reference, as well as significant insertion/deletion mutations, are not always going to be identified.

Sequencing of short amplicons also makes obtaining entire sequences possible in either a single read or using a paired-end read design. Here, adapters can be added directly to the ends of the amplicons and sequenced to retain haplotype information essential for reconstructing antibody or T cell receptor gene sequences as well as identifying species in micro-biome projects.

However, it is often necessary to design longer amplicons for targeted sequencing applications. In this case, the PCR products need to be fragmented for sequencing. Amplicons can be fragmented as-is using acoustic shearing, sonication, or enzymatic digestion. Alternatively, they can be first concatenated into longer fragments using ligation followed by fragmentation. One problem associated with amplicon sequencing is the presence of chimeric amplicons generated during PCR by PCR-mediated recombination. This problem is exacerbated in low complexity libraries and by overamplification. The presence of the PCR primer sequences or other highly conserved sequences presents a technical limitation on some sequencing platforms that utilize fluorescent detection (i.e., Illumina). This can occur with amplicon-based sequencing such as microbiome studies using 16S rRNA for species identification. In this situation, the PCR primer sequences at the beginning of the read will generate the exact same base with each cycle of sequencing, creating problems for the signal detection hardware and software. This limitation is not an issue with Ion Torrent systems (not fluorescence-based) and can be addressed on Illumina systems by sequencing multiple different amplicons in the same lane whenever possible. An alternative strategy we employ is to use several PCR primers during PCR of a specific amplicon. Each primer has a different number of bases (typically 1-3 random bases) added to the 5' end to offset/stagger the order of sequencing when adapters are ligated to the amplicons.

Additional Sequencing Approaches

Originally developed as a low-throughput PCR-based assay, the introduction of NGS technology has allowed ChIP-seq to be efficiently applied on a genome wide scale. The general principle of this assay involves immunoprecipitation of specific proteins along with their associated DNA. The procedure usually requires DNA-protein crosslinking with formaldehyde followed by fragmentation of the chromatin using micro-coccal nuclease (MNase) and/or sonication. Specific antibodies are used to target the protein or histone modification of interest, at which point the DNA is purified and subjected to high throughput sequencing. The sequencing results should be compared with a proper control. Data from a successful ChIP-seq should be enriched for the sequences that were crosslinked to the targeted protein/modified histone.

RNA binding proteins (RBPs) recognize ribonucleic acid motifs including specific sequences, single-stranded backbones, secondary structures, and double-stranded RNA (72, 73). These interactions involve all types of RNAs and occur at every step from transcription to degradation. Many steps in the post-transcriptional processing of messenger RNA overlap, resulting in multiple RBP complexes bound to a transcript at any given moment in its existence. RIP-seq can be done with protein-specific antibodies or by expressing tagged versions of the RBPs of interest. Furthermore, RIP-seq provides the ability to characterize the function of an RBP in a specific cell type and/or cell state based on the population of bound RNAs.

Methylation of the 5 position of cytosine (5 mC) is the most common form of DNA methylation, with 60%-80% of the 28 million CpG dinucleotides in the human genome being methylated. While genome-wide hypomethylation has been linked to increased rates of mutation and chromosomal instability, hypermethylation of promoters inhibits gene transcription. DNA methylation is also essential for genetic imprinting, suppression of transposable elements, and X chromosome inactivation. Aberrant DNA methylation is associated with many diseases including cancer, autoimmune diseases, inflammatory diseases, and metabolic disorders. Methylation sensitive restriction enzyme sequencing (MRE-seq) relies on restriction enzymes that are sensitive to CpG methylation. Affinity enrichment of methylated DNA requires either antibodies specific for methylated DNA (MeDIP) or other proteins capable of binding methylated DNA (MBDseq). Treatment of DNA with sodium bisulfite results in the chemical conversion of unmethylated cytosine to uracil while methylated cytosines are protected.

ATAC-seq identifies accessible DNA regions by probing open chromatin with hyperactive mutant Tn5 Transposase that inserts sequencing adapters into open regions of the genome. While naturally occurring transposases have a low level of activity, ATAC-seq employs the mutated hyperactive transposase. In a process called "tagmentation", Tn5 transposase cleaves and tags double-stranded DNA with sequencing adaptors. The tagged DNA fragments are then purified, PCR-amplified, and sequenced using next-generation sequencing. Sequencing reads can then be used to infer regions of increased accessibility as well as to map regions of transcription factor binding sites and nucleosome positions. The number of reads for a region correlate with how open that chromatin is, at single nucleotide resolution.

Addition of Adaptors and Sample Indexes

As described herein, sequences may be added to polynucleotides of the sample through transposition, ligation, tailing and template switching, and/or PCR with primers (e.g., that are degenerate, target specific, or that hybridize sequences added to fragments by transposition, ligation or tailing and template switching). Added sequences may flank inserts, such as cDNA or gDNA inserts. Added sequences may provide primer binding sites for further amplification, sequencing adaptors, unimolecular identifiers, and/or sample indexes (barcodes) that allow for pooling of samples. A sequencing adaptor may include indexes and optional index primers, amplification elements (e.g. for bridge amplification during sequencing), and read primers for sequencing.

Additional Steps

Additional steps include harvesting from a microfluidic device, depletion steps (such as of ribosomal RNA through enzymatic degradation, cleavage, hybridization, etc.), sample normalization, and pooling prior to sequencing. Sample normalization, and in particular, sample normalization based on suppression qPCR, is described further herein.

Bias

The main objective when preparing a sequencing library is to create as little bias as possible. Bias can be defined as the systematic distortion of data due to the experimental design. Since it is impossible to eliminate all sources of experimental bias, the best strategies are: (i) know where bias occurs and take all practical steps to minimize it and (ii) pay attention to experimental design so that the sources of bias that cannot be eliminated have a minimal impact on the final analysis.

The complexity of an NGS library can reflect the amount of bias created by a given experimental design. In terms of library complexity, the ideal is a highly complex library that reflects with high fidelity the original complexity of the source material. The technological challenge is that any amount of amplification can reduce this fidelity. Library complexity can be measured by the number or percentage of duplicate reads that are present in the sequencing data. Duplicate reads are generally defined as reads that are exactly identical or have the exact same start positions when aligned to a reference sequence. One caveat is that the frequency of duplicate reads that occur by chance (and represent truly independent sampling from the original sample source) increases with increasing depth of sequencing. Thus, it is critical to understand under what conditions duplicate read rates represent an accurate measure of library complexity.

Using duplicate read rates as a measure of library complexity works well when doing genomic DNA sequencing, because the nucleic acid sequences in the starting pool are roughly in equimolar ratios. However, RNA-seq is considerably more complex, because by definition the starting pool of sequences represents a complex mix of different numbers of mRNA transcripts reflecting the biology of differential expression. In the case of ChIP-seq the complexity is created by both the differential affinity of target proteins for specific DNA sequences (i.e., high versus low). These biologically significant differences mean that the number of sequences ending up in the final pool are not equimolar.

However, the point is the same—the goal in preparing a library is to prepare it in such a way as to maximize complexity and minimize PCR or other amplification-based clonal bias. This is a significant challenge for libraries with low input, such as with many ChIP-seq experiments or RNA/DNA samples derived from a limited number of cells. It is now technologically possible to perform genomic DNA and RNA sequencing from single cells. The key point is that the level of extensive amplification required creates bias in the form of preferential amplification of different sequences, and this bias remains a serious issue in the analysis of the resulting data. One approach to address the challenge is a method of digital sequencing that uses multiple combinations of indexed adapters to enable the differentiation of biological and PCR-derived duplicate reads in RNA-seq applications (41, 42). A version of this method is now commercially available as a kit from Bioo Scientific (Austin, TX).

When preparing libraries for NGS sequencing, it is also critical to give consideration to the mitigation of batch effects. It is also important to acknowledge the impact of systematic bias resulting from the molecular manipulations required to generate NGS data; for example, the bias introduced by sequence-dependent differences in adaptor ligation efficiencies in miRNA-seq library preparations. Batch effects can result from variability in day-to-day sample processing, such as reaction conditions, reagent batches, pipetting accuracy, and even different technicians. Additionally, batch effects may be observed between sequencing runs and between different lanes on an Illumina flow-cell. Mitigating batch affects can be fairly simple or quite complex. When in doubt, consulting a statistician during the experimental design process can save an enormous amount of wasted money and time.

There are many ways to minimize bias during library preparation. Within a single experiment, we aim to start with samples of similar quality and quantity. We also use master mixes of reagents whenever possible. One particularly egregious source of bias is from amplification reactions such as PCR; it is well documented that GC content has a substantial impact on PCR amplification efficiency. PCR enzymes such as Kapa HiFi (Kapa Biosystems, Wilmington, MA) or AccuPrime Taq DNA Polymerase High Fidelity (Life Technologies) have been shown to minimize amplification bias resulting from extremes of GC content.

In addition to enzymatic steps, bias can be reduced in purification steps by pooling barcoded samples before gel or bead purification. In the case of miRNA-seq libraries, we first run the individual libraries on an Agilent Bioanalyzer (Agilent Technologies, Santa Clara, CA) to quantitate the miRNA peaks. We use this information to create barcoded library pools of up to 24 samples and then perform gel purification in a single lane of an agarose gel to avoid sizing variation between samples.

Sample Normalization

Sample normalization as referred to herein is a physical step in which polynucleotides of samples to be pooled are quantified to determine the amount of each sample to add to the pool in order to achieve uniform sequencing across samples. This process may also called library quantification and pooling. Quantification is typically performed by traditional qPCR, or mobility (e.g., electrophoresis) assay such as on a Bioanalyzer (a chip-based capillary electrophoresis system), to quantify the amount of a desired product (polynucleotide) across samples. Samples are then pooled based on this quantitation, e.g., so as to improve uniformity of read depth across samples. For example, samples with a lower concentration of a library prepped polynucleotide (or desired library prepped polynucleotide) may be added to the pool at greater volume. Library prepped polynucleotides may be sample barcoded (e.g., comprise dual indexes), and may or may not include additional adaptor sequences. Read depth can be defined as the number of reads in a given sequencing run, and can further be defined as number of successful reads (e.g., reads mapped to a known sequence or genome). A related concept, sequencing depth uniformity, may also be used. The desired product may be, for example, a library prepped polynucleotide having an insert of a given length.

Traditional quantification methods may amplify artefacts such as primer dimer, or by mobility based assays such as electrophoresis in which artefacts such as bubble DNA (formed from adaptor rehybridization with insert mismatch) runs at similar speed as desired long products. As such, an aspect of the subject application is the use of suppression PCR (e.g., suppression qPCR) to quantify long desirable products over artefacts such as primer dimer, bubble DNA, and products with short inserts.

Read-depth is directly proportional to sequencing costs and thus less variation leads to better results and less costly sequencing.

Suppression PCR

Figure 5:
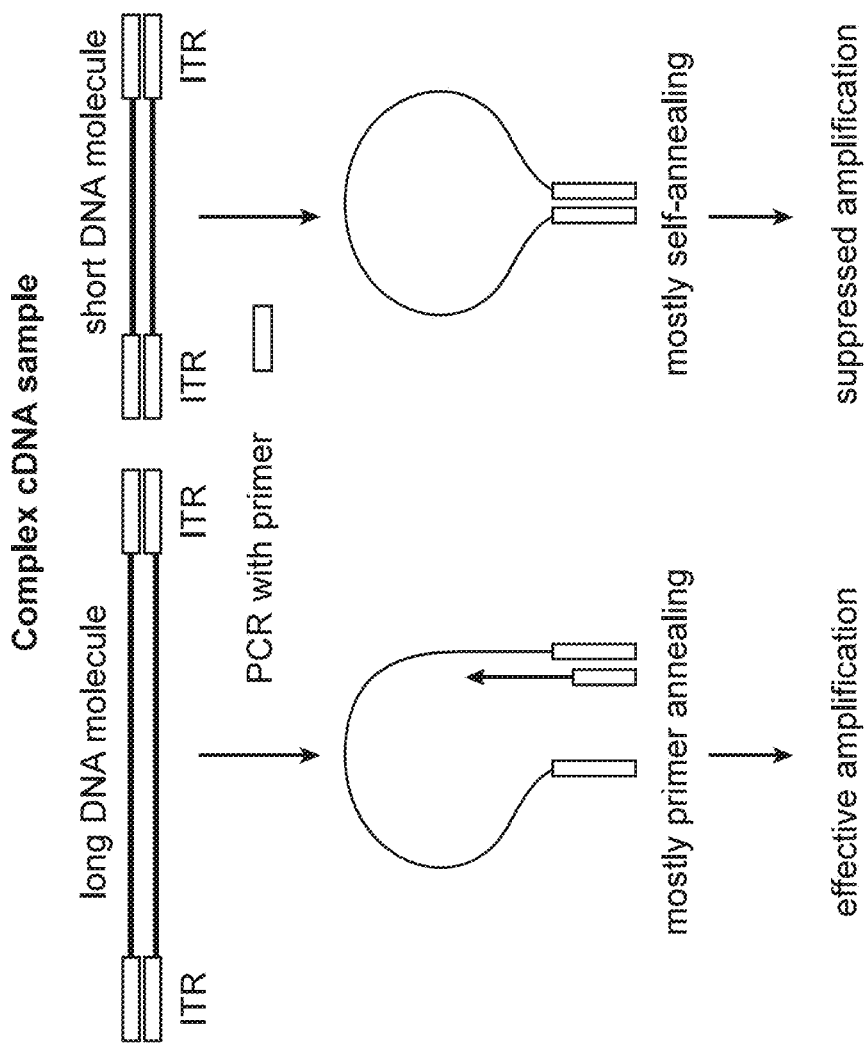
FIG. 5 shows the principal mechanism of suppression PCR in which a short sequence with spaced inverted repeats, such as ITRs, forms a hairpin that suppresses amplification by a primer that hybridizes to the inverted repeats exposed by the longer DNA molecule.

Suppression PCR been used to enrich for long products, as short products form hairpins at the primer binding site, for example to increase long products for use as vectors or to enrich for long products that for sequencing. Suppression PCR for regulation of product length was described by Shagin et al. in "Regulation of average length of complex PCR product." Nucleic Acids Research 27.18 (1999): e23-i. To the inventor's knowledge, suppression qPCR and its use in library normalization has not been disclosed. Suppression PCR is illustrated in FIG. 5.

In suppression PCR as used herein, a single primer (or primers) complementary to an inverted repeat will preferentially extend longer products in which the inverted repeat is spaced farther apart, as those longer products tend to remain linear. Shorter products, for example, in which the inverted repeat is spaced apart by less than 100, less than 80, less than 50, or less than 30 nucleotides, tend to form a hairpin in which the inverted terminal repeat forms the neck and prevents primer hybridization.

Figure 6:
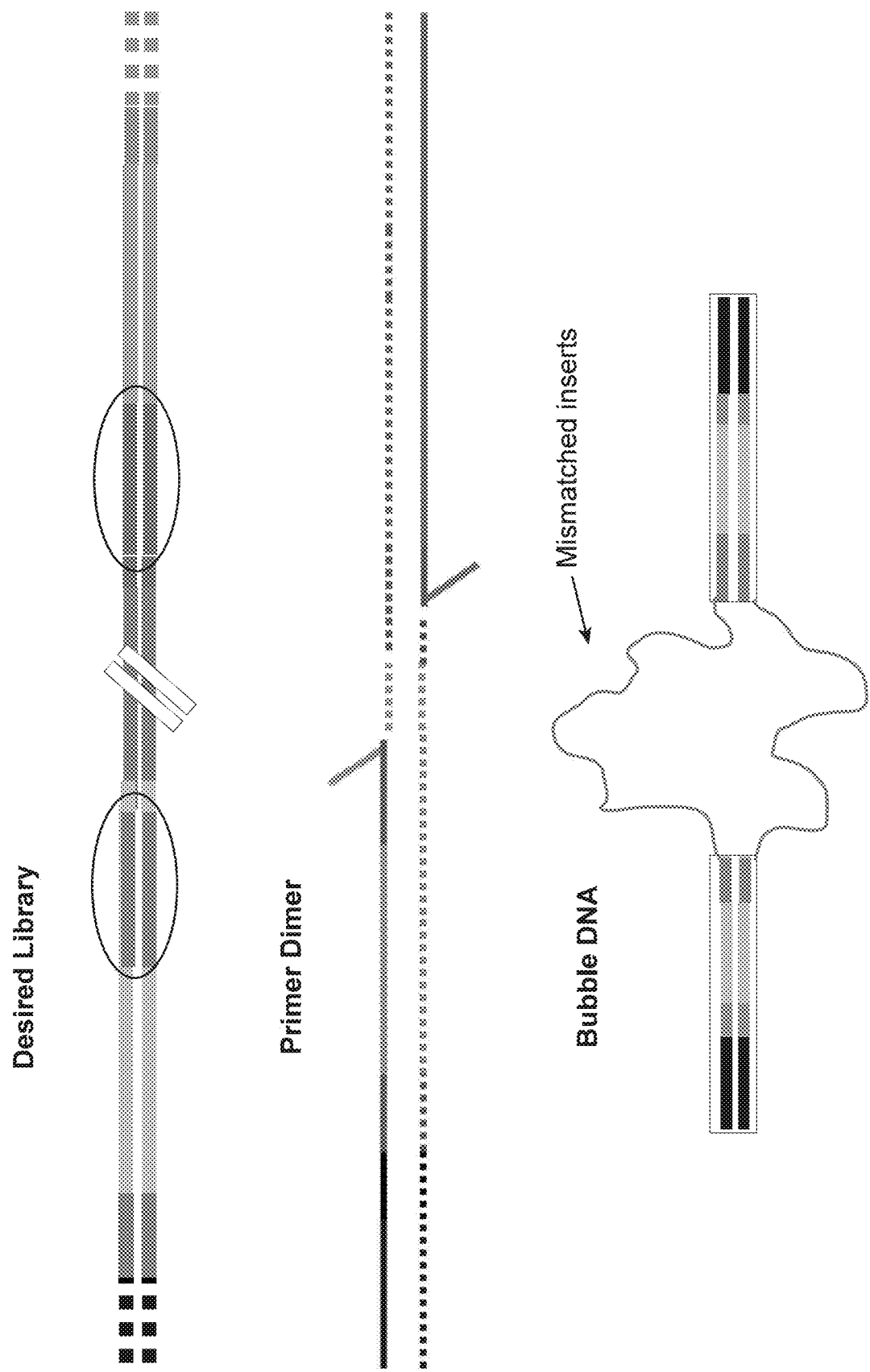
FIG. 6 shows various polynucleotides produced in certain library preparation workflows, such as through PCR based incorporation of inverted repeats, sequencing adapters and/or sample barcodes. A desired library product (top) with spaced inverted repeats (circled) that flank an insert which may comprise more than half the length of the polynucleotide. The polynucleotide further includes a sequencing adaptor (dotted line). A primer dimer product (middle) is shown that has inverted repeats in close proximity. Such a product may interfere with traditional qPCR. A "bubble DNA" product (bottom) is shown in which adapters have reannealed and the inserts are mismatched. Such a product may interfere with quantification of long products (e.g., by a mobility assay such as capillary electrophoresis).

As described above, quantification methods may amplify artefacts from library preparation (e.g., shown in FIG. 6) such as primer dimer that interferes with qPCR, or bubble DNA which interferes with mobility based assays such as capillary electrophoresis. As such, an aspect of the subject application is the use of suppression PCR (e.g., suppression qPCR) to quantify long desirable products over artefacts such as primer dimer, bubble DNA, and products with short inserts.

In certain aspects, suppression PCR is done with a primer that includes a sequence identical to at least 6, at least 8, at least 10, at least 12, or at least 15 nucleotides of a spaced inverted repeat (and therefore complementary to that length of nucleotides of the other spaced inverted repeat sequence). Sample preparation may be with primer identical to an inverted repeat of a polynucleotide (e.g., and complementary to the partner inverted repeat, such that it hybridizes to at least one inverted repeat during PCR).

Quantitation by suppression PCR may direct pooling of samples to normalize for read uniformity. In certain aspects, aliquots from samples, but not polynucleotides in the sample pool itself, undergo suppression PCR.

Suppression PCR may enrich for longer amplicons. For example, suppression PCR may enrich for long polynucleotides (e.g., with more than 100, more than 150, more than 200, more than 300, or more than 400 nucleotides between inverted repeats) at least 5 fold (e.g., at least 10 fold, at least 25 fold, at least 50 fold, at least 80 fold, at least 100 fold) more than shorter polynucleotides (e.g., with less than 100 nucleotides, less than 80 nucleotides, less than 50 nucleotides, less than 30 nucleotides, or less than 20 nucleotides between inverted repeats).

Suppression PCR may preferentially amplify longer polynucleotides. For example, suppression PCR may amplify long polynucleotides (e.g., with more than 100, more than 150, more than 200, more than 300, or more than 400 nucleotides between inverted repeats) at a PCR cycle efficiency of at least 0.20 (e.g., 0.25, 0.3, 0.4, 0.5, or 0.6) more than for shorter amplicons (e.g., with less than 100 nucleotides, less than 80 nucleotides, less than 50 nucleotides, less than 30 nucleotides, or less than 20 nucleotides between inverted repeats). For example, the PCR efficiency for a long polynucleotide may be greater than 1.6, 1.75, 1.8, 1.85, or 1.9. The PCR efficiency for a short polynucleotide may be less than 1.6, 1.5, 1.4, or 1.3.

Quantitation may be by qPCR (i.e., such as suppression qPCR) as described herein. Alternative methods of quantifying suppression PCR are also described herein. The length of the library quantification standards may be between 150 and 800 nucleotides, such as between 200 and 600 nucleotides. Methods may further include melting curve analysis of the suppression PCR products. Quantification may be based on a dilution series of a library quantification standard.

Some library prep workflows introduce palindromic sequences (spaced inverted repeats), which form hairpins in short products. Longer sequences can be quantified by suppression qPCR, in which a single primer complementary to an inverted repeat is used. Shorter products form hairpins, as the inverted repeats are in closer proximity, which competes with the primer and decreases amplification efficiency. If the amplification efficiency of long (e.g., >200 nt) products is 1.8 fold per cycle, and the amplification efficiency of short (e.g., <50 nt insert) products is around 1.5, then over 24 cycles the long products will amplify at $(1.8^{\wedge}24)/(1.5^{\wedge}24)$ =80 times more than the short products.

Library preparation workflows can lead to issues with read-depth uniformity per sample in each pool on sequencing runs. For example, in the initial commercial protocol, the Advanta™ RNA-Seq NGS Library Prep Kit (Fluidigm Corp) did not include a method to quantify each sample library and normalize prior to pooling. Read-depth is directly proportional to sequencing costs and thus less variation leads to better results and less costly sequencing. We seek to employ a method of quant-norm prior to pooling that also doesn't require any bead purification.

Aspects of a kit described herein use random primers, e.g., to introduce Illumina adaptor sequences through PCR, which creates unwanted primer dimer (e.g., p5 and p7 primer) that interferes with quantification by traditional qPCR. Primer dimer forms to a greater extent with lower inputs. When sample inputs are of variable quantity and/or quality, an unnormalized (or poorly normalized) pool will result in non-uniform read-depth. Bubble DNA produced by adapter-driven rehybridization complicates quantification by mobility (such as on a gel or bioanalyzer instrument), as bubble DNA runs at a similar speed to longer double stranded products that are desired.

Other library prep methods may also create undesired short products that complicate quantification, and that form hairpin structures due. For example, short fragments formed from transposases that introduce inverted terminal repeats may create similar issues that can be addressed by the invention.

As suppression PCR preferentially amplifies long products over short hairpins, suppression qPCR would allow quantification of such long products. Sample normalization by pooling samples based on suppression qPCR would allow for uniform sequencing of long reads across samples. As such, samples with abundant long products would not need to be oversequenced to achieve adequate sequencing depth for other samples in the pool, even if artefacts prevent or inhibit traditional quantification methods from being used for sample normalization.

In certain aspects, suppression qPCR may be combined with melting curve analysis to ensure short products were not amplified to higher abundance than long products (e.g., when short products vastly outnumber long products initially past the point that could be remediated by suppression qPCR, such as more than 80 fold in the above example).

Of note, other quantification workflows may not be suitable. Primer dimer formed with low inputs interferes with traditional qPCR. When the primer sequences include the inverted repeat, these primer dimers will form hairpins with a neck defined by the inverted repeat.

Bubble DNA formed by annealing of adapters on different inserts interferes with mobility based methods (e.g., electrophoresis).

Additional library prep workflows would lend themselves to quantification by suppression qPCR, which would preferentially amplify longer products that do not form hairpins. For example, inverted repeats introduced in transposase based workflows may form hairpins in smaller fragments.

Aspects of sample normalization by suppression qPCR find use in any library prep workflow that pools samples (not tied to Advanta workflow or IFC) and results in unwanted short hairpin by-products that have a known inverted repeat forming the neck. For example, primer (e.g., adapter) dimer may form if some samples have low input. Short products may form if sample nucleic acids are fragmented (e.g., RNA in FFPE samples). In either or both cases, if the primers have a shared sequence (such as a palindromic sequence 8 or more, 10 or more, or 12 or more nucleotides in length), these short products will form hairpin structures, and qPCR with primer(s) that hybridize the palindromic sequence will preferentially amplify long "readworthy" products over short hairpins that do not present single stranded palindromic sequence. In another example, a transposase based workflow such as for ATAC seq or WGS may incorporate inverted terminal repeats that form hairpin structures when the flanked sample DNA fragment is short.

PCR conditions (e.g., temperature and/or time of steps in the PCR cycle, number of cycles, buffer, etc.) may be tuned to improve suppression (e.g., the preferential amplification of long polynucleotides over short). In certain aspects, annealing and/or extension steps may be run at a higher temperature (e.g., at least 3, 5, or 10 degrees Celsius higher) in later cycles (e.g., starting at a cycle after cycle 1, 2, 5, 10, etc.). This may be most beneficial when the primer for suppression PCR comprises a 5' sequence that does not hybridize to the polynucleotide, but that will hybridize to amplicons of earlier cycles (increasing the melting temperature of primer hybridization after the first cycle). Short amplicons would still form hairpins at these higher temperatures, as the neck of the hairpin structure could include the 5' sequence.

Sample Polynucleotide

Sample polynucleotides for sample normalization may be any library prepped nucleotide that is sample barcoded (e.g., indexed) such that samples can be demultiplexed after pooling. The sample polynucleotide may have sequencing adaptors, or such sequencing adaptors may be added after pooling. For sample normalization by suppression qPCR, sample polynucleotides may have spaced inverted repeats (i.e., inverted repeats separated by another sequences, such as an insert).

Polynucleotides may be library prepped for sequencing (e.g., referred to as a sample library), and may comprise adapters (e.g., one or more sequences to assist sequencing, such as indexes, read primer binding sites, indexing primer binding sites, amplification primer binding sites such as P5/P7 sequences). Polynucleotides (e.g., adapter regions of polynucleotides) may include spaced inverted repeats as described herein. Adapters and/or spaced inverted repeats may be flanking an insert, such as a cDNA or gDNA sequence. The insert may be of variable length, such as when fragmentation is for sample preparation. Polynucleotides may include sample barcodes, such as on adaptor sequences. Sample barcodes may be dual indexes.

In certain aspects, polynucleotides comprise spaced inverted repeats, such as two spaced inverted repeats. The spaced inverted repeats are at least 6, at least 8, at least 10, at least 12, or at least 15 nucleotides long. Spaced inverted repeats are within 50 nucleotides of their respective ends (3' and 5' ends). For example, spaced inverted repeats may be terminal inverted repeats.

Spacing between inverted repeats may be variable. For example, longer polynucleotides in a sample may have more than 100, more than 150, more than 200, more than 300, or more than 400 nucleotides between inverted repeats. Shorter polynucleotides may have less than 100 nucleotides, less than 80 nucleotides, less than 50 nucleotides, less than 30 nucleotides, or less than 20 nucleotides between inverted repeats. Aspects of the subject application may include suppression PCR that preferentially amplifies longer polynucleotides. Some polynucleotides may include an insert, such as a cDNA or gDNA sequence, flanked by the inverted repeats. The insert may be randomly generated, or may be target specific (e.g., gene specific) sequence. The insert sequence may be an endogenous sequence or its reverse complement.

Figure 7:
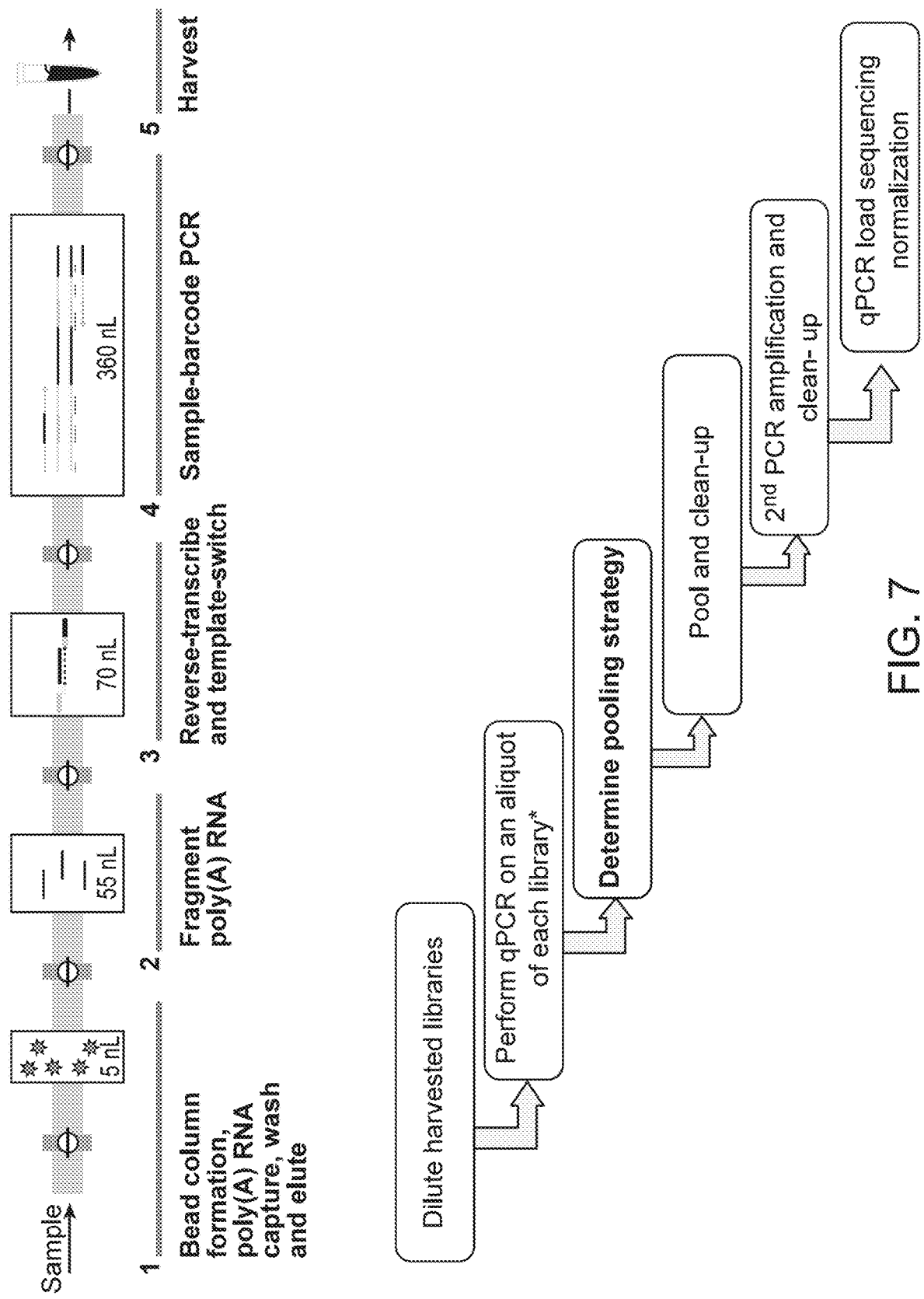
FIG. 7 shows a microfluidic multi-step sample preparation workflow (top) that provides sample barcoded libraries. A qPCR quantification and normalization workflow to guide pooling of the different samples different samples is shown (bottom). In the subject application, the qPCR step may be a suppression qPCR as described herein.

Polynucleotides may include, or may be sample prepared to include, a spaced inverted repeat (e.g., of a sequencing adaptor). For example, polynucleotides may include Illumina p5 and p7 sequencing adaptors. In certain aspects, a sample has an average polynucleotide length of less than half of the average polynucleotide length across the samples Production of Sample Polynucleotide Sample polynucleotides may be provided by any of the methods described herein for sample preparation (e.g., library preparation). For example, PCR may incorporate spaced inverted repeats (e.g., in addition to sample indexes and/or sequencing adaptors). In another example, transposases may fragment target DNA and introduce spaced inverted repeats, often described in the art as "inverted terminal repeats". An example of sample production (library preparation), using a microfluidic workflow and sample normalization, is shown in FIG. 7.

Polynucleotides may be library prepped for sequencing (e.g. referred to as a sample library), and may comprise adapters (e.g., one or more sequences to assist sequencing, such as indexes, read primer binding sites, indexing primer binding sites, amplification primer binding sites such as P5/P7 sequences). Polynucleotides (e.g., adapter regions of polynucleotides) may include spaced inverted repeats as described herein. Adapters and/or spaced inverted repeats may be flanking an insert, such as a cDNA or gDNA sequence. The insert may be of variable length, such as when fragmentation is for sample preparation. Polynucleotides may include sample barcodes, such as on adaptor sequences. Sample barcodes may be dual indexes.

In certain aspects, polynucleotides comprise spaced inverted repeats, such as two spaced inverted repeats. The spaced inverted repeats are at least 6, at least 8, at least 10, at least 12, or at least 15 nucleotides long. Spaced inverted repeats may be within 80 nucleotides, within 50 nucleotides, within 30 nucleotides, or within 20 nucleotides of their respective ends (3' and 5' ends). For example, spaced inverted repeats may be terminal inverted repeats.

Spacing between inverted repeats may be variable. For example, longer polynucleotides in a sample may have more than 100, more than 150, more than 200, more than 300, or more than 400 nucleotides between inverted repeats. Shorter polynucleotides may have less than 100 nucleotides, less than 80 nucleotides, less than 50 nucleotides, less than 30 nucleotides, or less than 20 nucleotides between inverted repeats. Aspects of the subject application may include suppression PCR that preferentially amplifies longer polynucleotides. Some polynucleotides may include an insert, such as a cDNA or gDNA sequence, flanked by the inverted repeats. The insert may be randomly generated, or may be target specific (e.g., gene specific) sequence. The insert sequence may be an endogenous sequence or its reverse complement.

Polynucleotides may include, or may be sample prepared to include, a spaced inverted repeat (e.g., of a sequencing adaptor). For example, polynucleotides may include Illumina p5 and p7 sequencing adaptors. In certain aspects, a sample has an average polynucleotide length of less than half of the average polynucleotide length across the samples.

Samples may be prepared by steps described in other sections.

Primers for Suppression PCR

A suppression PCR primer may be identical to an inverted repeat (and therefore complementary to its partner), or may include a subsequence that is identical or similar enough to specifically hybridize to an inverted repeat (or portion thereof) under stringency conditions of a PCR reaction.

In certain aspects, a primer for suppression PCR may have a 3' sequence identical to an inverted repeat or a portion thereof (i.e., complementary to the other inverted repeat). The sequence may be identical to at least 6, at least 8, at least 10, at least 12, or at least 15 nucleotides of the inverted repeat. The single primer may selectively amplify longer products (e.g., having more space between spaced inverted repeats), and is sufficient to drive the PCR reaction in the absence of another primer (e.g., in the presence of master mix and a suitable polymerase and thermocycling conditions). When the primer includes a sequence identical to a spaced inverted repeat at the 3' end of the primer, it may only hybridize when the polynucleotide is not forming a hairpin with a neck defined by the inverted repeats.

The primer may include a 5' sequence that is not complementary to the polynucleotide but that increases suppression of short amplicons over long amplicons produced in earlier PCR cycles. For example, the 5' sequence may be at least 4, at least 6, at least 8, at least 10, at least 12, or at least 15 nucleotides. The 5' sequence may increase the length of inverted repeats in amplicons, such that hairpins form with a longer neck (increasing suppression of shorter amplicons). As such, PCR annealing and/or extension temperature may, at least in initial cycles, be low (such as less than 60 degrees Celsius, less than 56 degrees Celsius, or less than 52 degrees Celsius). Later cycle annealing and/or extension temperatures may be higher than in initial cycles as described herein.

In general, PCR annealing and/or extension temperature may be more than 50 and/or less than 75 degrees Celsius.

Suppression PCR and kits thereof may only use one primer, or may use two different primers both having a 3' sequence identical to at least 6, at least 8, at least 10, at least 12, or at least 15 nucleotides of a spaced inverted repeat.

In some embodiments, the primer can (e.g., a single primer can), in the presence of master mix and polymerase, amplify sample polynucleotides having inverted repeats spaced 200 or more nucleotides apart at 0.25 or greater cycle efficiency than sample polynucleotides having inverted repeats spaced 50 nucleotides or less. The primer may, in the presence of master mix and polymerase, amplify the library quantification standard at 1.8 or greater efficiency per cycle, but will amplify sample polynucleotides having inverted repeats spaced by 50 nucleotides or less at 1.5 or less efficiency in per cycle.

The inverted repeat the primer hybridizes to (e.g., or is identical to) may be introduced by sequencing adaptors, such as those used in library preparation kits described herein. As such, suppression PCR primers that hybridize an inverted repeat of Illumina adapters provided by library preparation kits described herein are within the scope of the application.

Quantification

Sample libraries may be quantified to determine the amount of individual samples to add to a sample pool prior to sequencing. As described herein, suppression PCR may be used to amplify polynucleotides of aliquots from samples. Polynucleotides may be library prepped reaction products that comprise spaced inverted repeats (e.g., alongside sample barcode(s) and/or sequencing adaptors) flanking an insert sequence, such as cDNA or gDNA. Suppression PCR may preferentially amplify polynucleotides with longer inserts, as shorter polynucleotides may preferentially form hairpin structures in which the inverted repeats form a double stranded neck that prevents primer hybridization and/or extension.

Suppression PCR products may be quantified to determine the amount of a sample (e.g., sample library) to add to a pool of samples. Quantification may be performed during suppression PCR, such as in a suppression quantitative PCR or "qPCR". In qPCR, abundance of double stranded DNA (dsDNA) is measured over multiple cycles using a dye indicator (such as an dsDNA intercalating dye), and the linear phase of amplification curve is used to calculate a starting amount of the target that was amplified. Other forms of quantitation may include end point detection (e.g., measuring amount of amplified target after a set number of runs, such as by a dye or by detection of amplification products run on a gel) or digital PCR.

Pooling may be performed based on the quantification of the samples. For example, quantification may be used to determine which samples to pool and/or how much (e.g., volume) of particular samples to pool. In certain aspects, multiple sample pools may be created.

Metrics of Improvement

Figure 8:
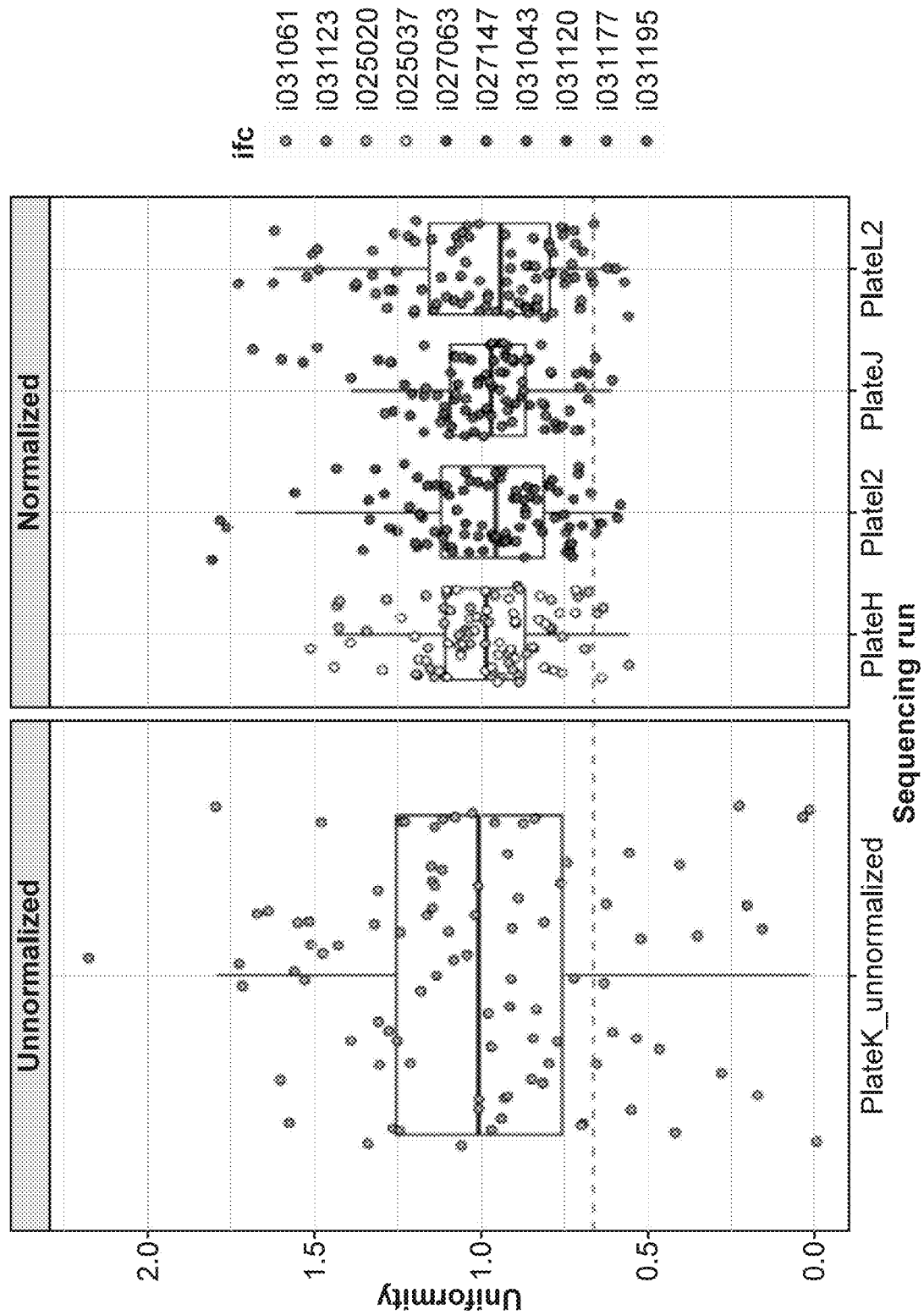
FIG. 8 shows read uniformity for unnormalized vs normalized sample pools. The normalized sample pools were pooled based on quantification by suppression qPCR. Traditional normalization (e.g., by bioanalyzer or by traditional qPCR) tends to show similarity to the unnormalized sample.
Figure 9:
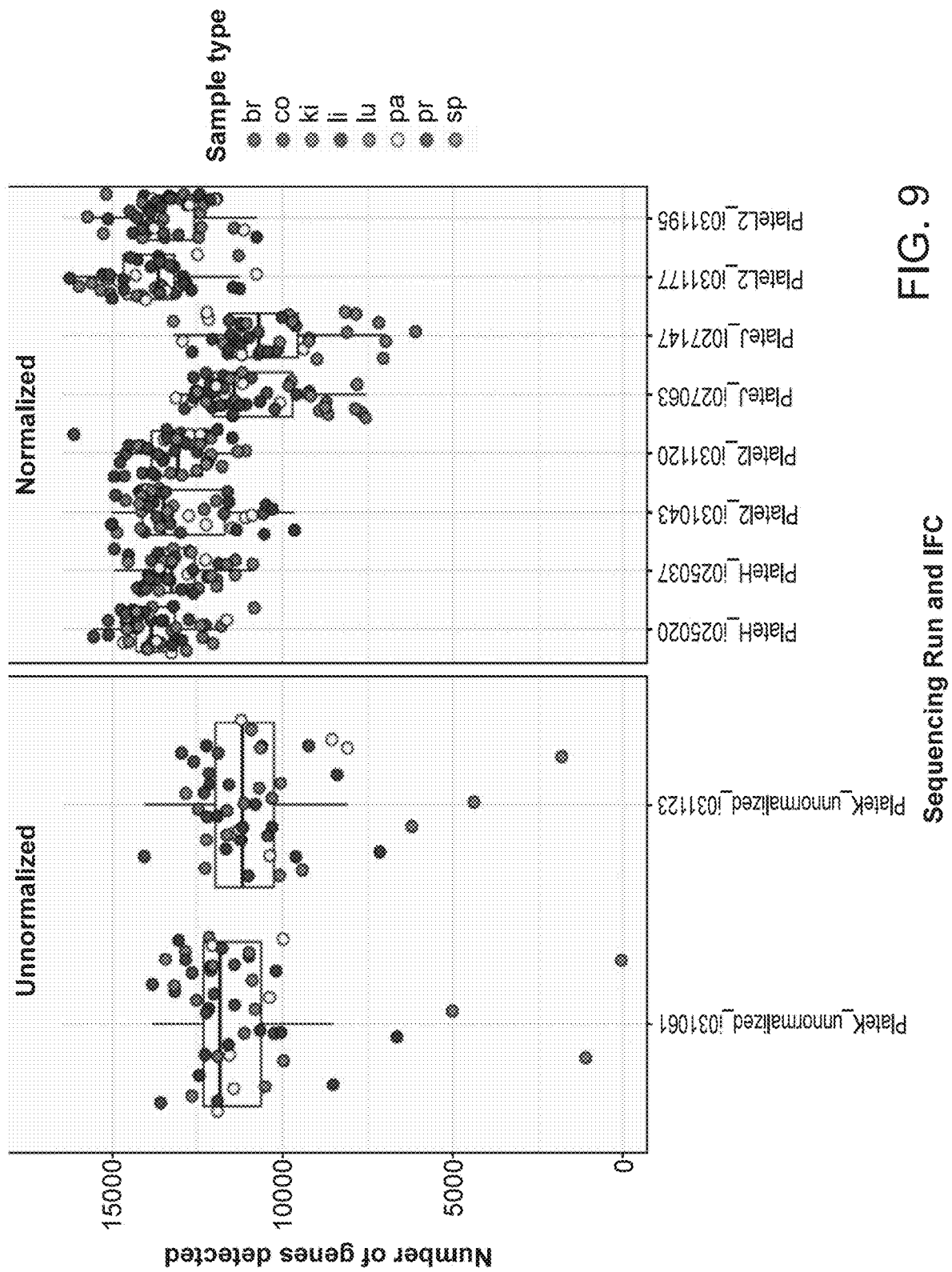
FIG. 9 shows number of genes detected for unnormalized vs normalized sample pools. The normalized sample pools were pooled based on quantification by suppression qPCR. Traditional normalization (e.g., by bioanalyzer or by traditional qPCR) tends to show similarity to the unnormalized samples.

The final library pool formed based on suppression qPCR quantification of the subject methods and/or kits may provide one or more metrics of success described herein. Some metrics of improvement are shown in FIGS. 8 and 9.

In certain aspects, one or more additional or alternative metrics below may be used. The library pool may be of at least 50 fmols, 100 fmols, 200 fmols, 300 fmols, 500 fmols, or 1000 fmols (e.g., and have at least 24 or 48 samples). The final library pool may provide a sequencing read depth uniformity of more than 80% or more than 90% of samples having at least half, or at least two thirds, the read depth of the average across samples.

Library normalization may read depth uniformity across pooled samples. For example, library normalization described herein may result in at least a two-fold reduction (e.g., at least a 3-fold reduction, or at least a 5 fold reduction) in read depth variation as measured by standard deviation and as compared to no normalization, or as compared to normalization based on normal qPCR (not suppression qPCR).

In some embodiments, fewer than 5% of the samples are at a read depth less than 50% of the average read depth across samples. For ample, in certain aspects, no library normalized samples are at a read depth less than 50% (e.g., less than 40%, less than 25%, or less than 10%) of the average read depth across samples. In addition, more than 5% of the samples may be at a read depth of less than 50% (e.g., less than 40%, less than 25%, or less than 10%) of the average read depth across samples, if the library were not normalized or were normalized by normal qPCR.

In some embodiments, all of normalized samples may have more than 2500 genes detected, such as more than 5000 genes detected, more than 7500 genes detected or more than 10,000 genes detected. In addition, at least some samples may have fewer than 5000 genes detected, fewer than 2500 genes detected, fewer than 1000 genes detected if the library were not normalized (e.g., for the same total number of reads).

Library normalization may result in at least a two-fold reduction (e.g., at least a 3-fold reduction, or at least a 5 fold reduction) in sequencing costs as compared to no normalization or as compared to normalization based on qPCR quantitation (e.g., after a bead cleanup step but not by suppression qPCR). In certain aspects, sequencing cost is the cost needed to achieve adequate coverage of all samples in the pool.

Kits

Kits of the subject application may include reagents and/or devices for performing any of the methods described herein, including methods of library preparation and/or normalization. Kits described herein in the context of library preparation for sequencing and/or quantitation or normalization of libraries for sequencing may be adapted with components described herein and/or for method steps described herein.

In certain aspects, a sample normalization kit (e.g., library quantification kit) may include a DNA standard having spaced inverted repeats and a single primer the hybridized one of the inverted repeats. The single primer may selectively amplify longer products (e.g., having more space between spaced inverted repeats), and is sufficient to drive the PCR reaction in the absence of another primer (e.g., in the presence of master mix and a suitable polymerase and thermocycling conditions).

In certain aspects, a library prep kit may include reagents to add inverted repeats, sample indexes, and optionally sequencing adaptors to sample polynucleotides. The kit may further include and a single primer the hybridized one of the inverted repeats. The single primer may selectively amplify longer products (e.g., having more space between spaced inverted repeats), and is sufficient to drive the PCR reaction in the absence of another primer (e.g., in the presence of master mix and a suitable polymerase and thermocycling conditions).

A kit may further include components for determining pooling of samples based on quantification, such as a workbook (e.g. spreadsheet) that takes qPCR measurement input and outputs instructions for pooling of quantified samples, such as which samples to pool and/or how much (e.g., volume) of particular samples to pool.

Alternative Uses of Suppression PCR

In certain aspects, suppression PCR may be used for applications outside of library quantification.

In some embodiments, primers may comprise sequences (e.g., internal or at their 5' ends) that are identical of one another (e.g., and more than 6, 8 or 12, or 15 nucleotides in length), and may comprise 3' sequences that are different from one another and that hybridize target nucleotide. The identical sequence can introduce spaced inverted repeats during amplification such that short products (e.g., primer dimer) form hairpins and are not efficiently amplified in future cycles, such as during qPCR or dPCR. The temperature of annealing and/or extension may be increased (e.g., by at least 3, 5 or 10 degrees Celsius, starting at a cycle after cycle 1, 2, 3, 5, 10, etc.) such that the 3' sequence no longer hybridizes the original target nor a short amplicon (e.g., primer dimer) that form hairpins.

In certain aspects, the 3' sequences is degenerate (e.g., a randomer of more than 3, 4, 6, or 8 nucleotides). In multiple cycle amplification with randomer primers, amplicons of subsequent amplification cycles can get successively smaller as new randomer primers hybridize new sites, which is undesirable for many applications (including sequencing). However, the formation of hairpin structures in short amplicons produced with inverted repeat introducing primers may promote amplification of long amplicons in future cycles. Further, an additional primer or primers (e.g., having the identical sequence from the first two primers at the 3' end and an adaptor sequence) can amplify long amplicons that do not form hairpins. The additional primer may be in excess of the earlier described primer(s).

Microfluidic Devices

Figure 2B:
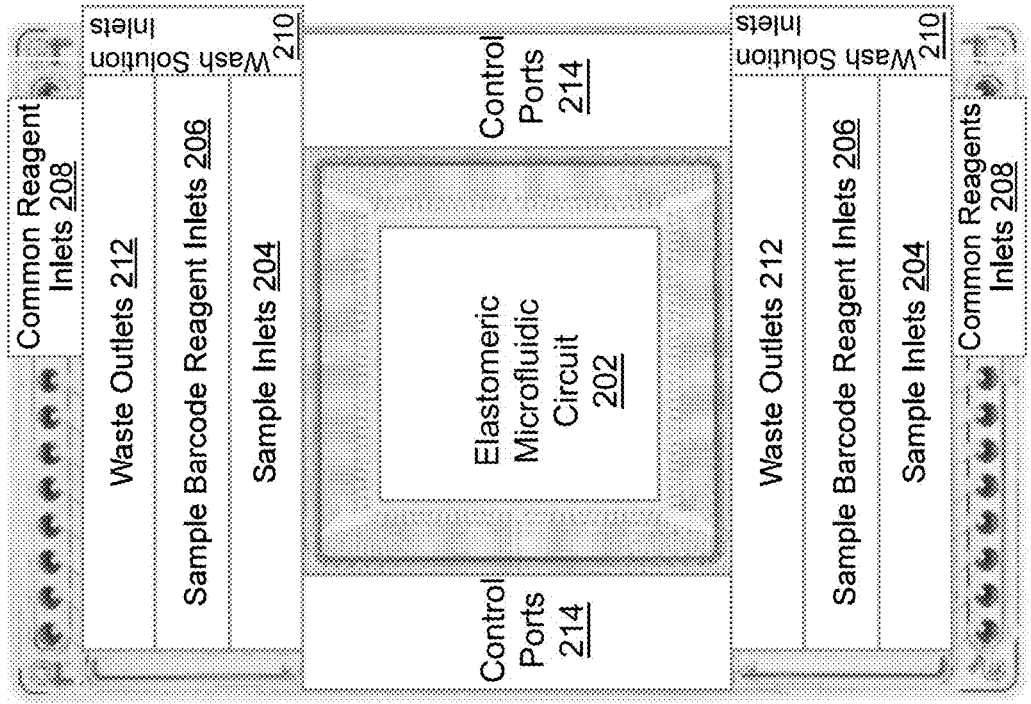
FIGS. 2A and 2B are images of an exemplary elastomeric microfluidic device 200 of the subject application.
Figure 2A:
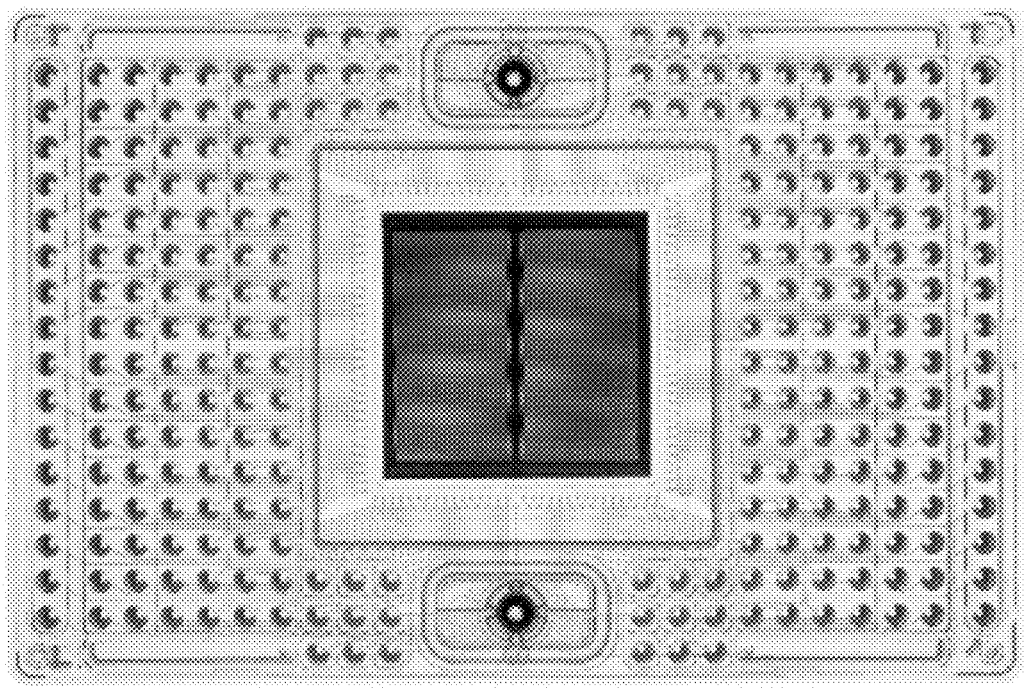
Figure 3:
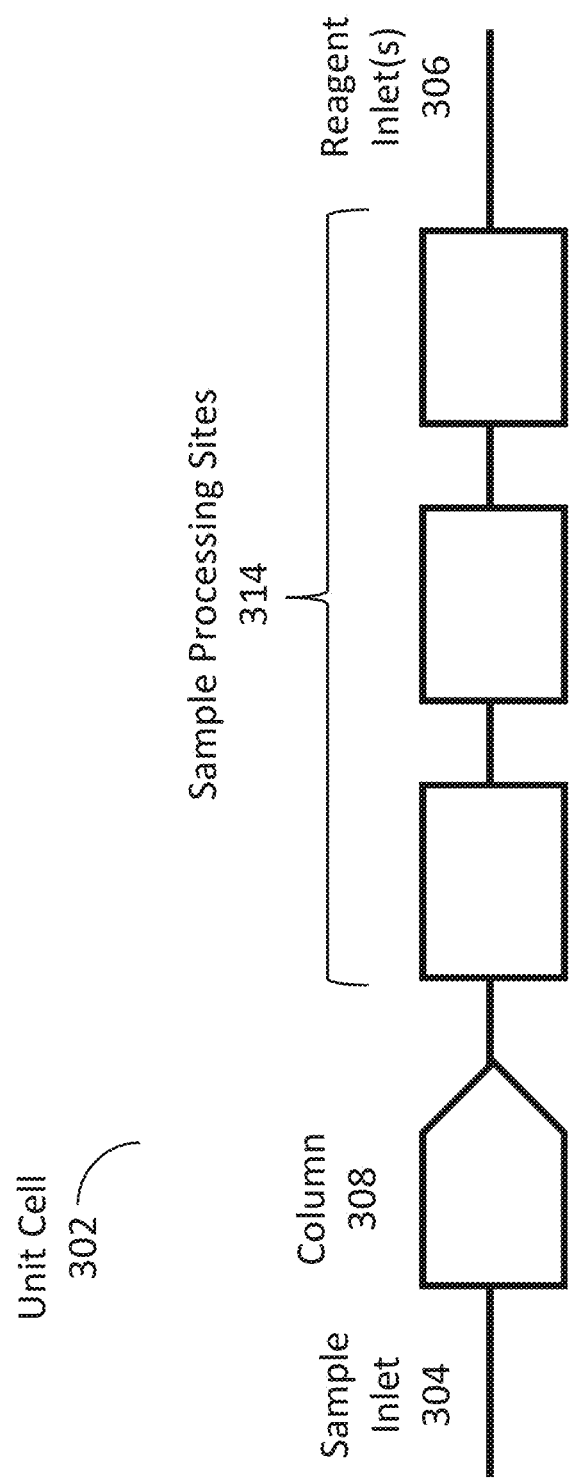
FIG. 3 is an abstraction of the architecture of a unit cell 320, e.g., of a fluidic circuit of FIG. 1 or 2. The unit cell may process a single sample provided by a sample inlet 304, and provide multiple sample processing sites 314 in which the sample is reacted with different reagents provided by one or more reagent inlet(s) 306. The unit cell may include a column 308 for enriching sample in the unit cell and/or additional elements such as waste outlets, valves, pumps, or other components of microfluidic devices described herein.
Figure 4:
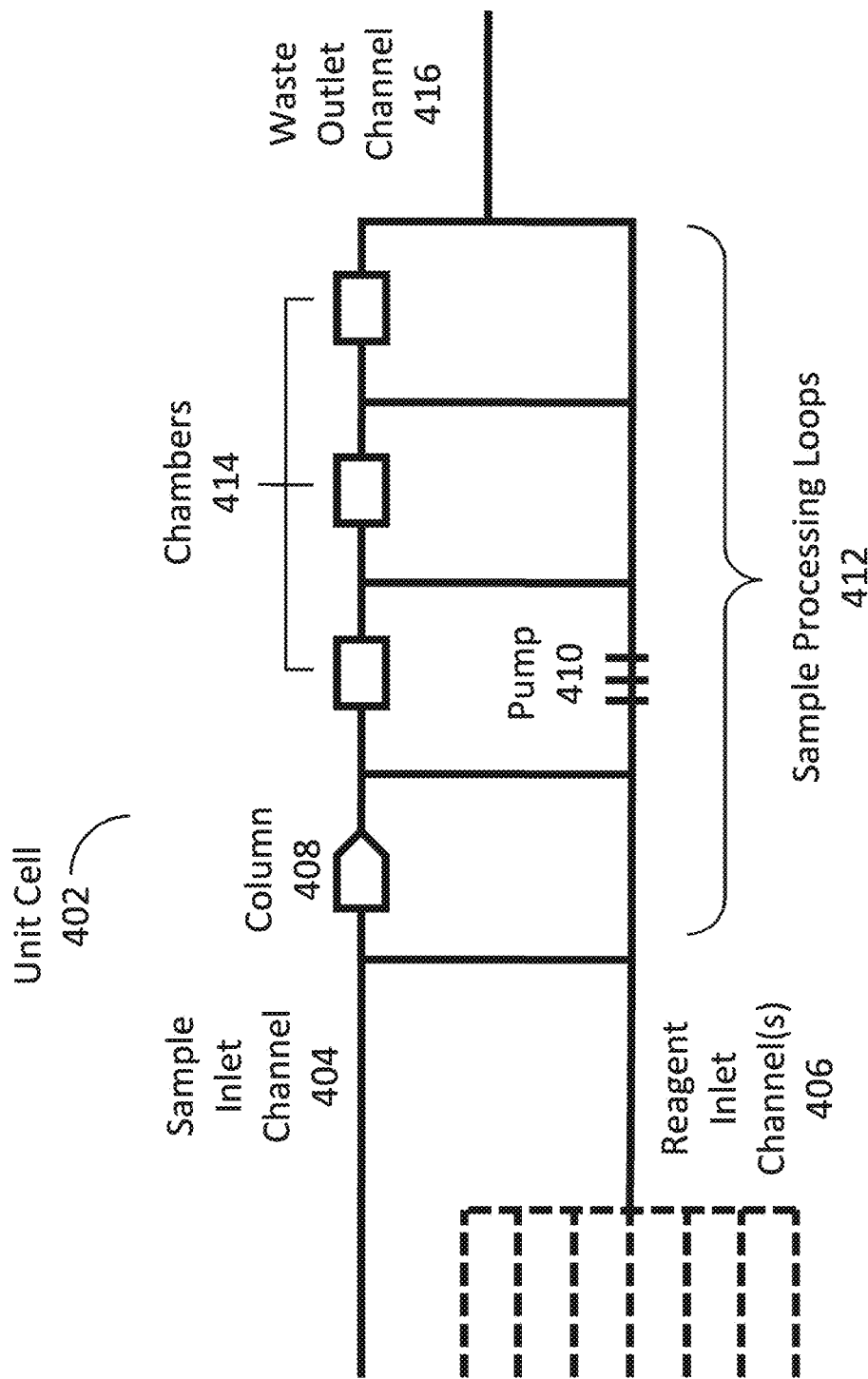
FIG. 4 is a detailed schematic of an exemplary unit cell 402 of FIG. 2. A plurality of reagent inlet channels 406 are shown, which may share a channel joining the unit cell. The plurality of sample processing sites may have chambers 414 and/or sample processing loops 412 for mixing sample and/or reagents between chambers. A waste outlet channel 416 is shown for removing excess or unwanted fluid from the unit cell. Valves (not shown) may be configured along the unit cell and operated to deliver sample and reagents to different locations (e.g., column, chambers, loops) in the unit cell, place sample processing loops or chambers in isolation or in communication with one another, drive mixing between reagents and/or sample at different locations, and direct flow of sample or reagent solution out of the unit cell (e.g., to waste and/or to a harvest outlet). The unit cell may include a sample inlet channel 404, a column 408 for enriching sample in the unit cell, and/or additional elements such as valves, pumps, or other components of microfluidic devices described herein.

Microfluidic devices described herein refer to devices that process fluid volumes (e.g., sample volumes) on the microliter scale (e.g., one ul to hundreds of ul) or less, such as 0.1 nl to 100 ul, 1 nl to 10 ul, 5 nl to 1 ul, or 10 nl to 100 nl. Alternatively, microfluidic devices refer to fluidic devices with channels, chambers or other fluidic architectures with a dimension on the micrometer scale (e.g., one um to hundreds of um) or less, such as 100 nm to 1 mm, or 1 um to 100 um. The architecture of microfluidic devices of the subject application may allow for controlled loading, isolation, mixing and/or harvesting of sample, reagents, and solutions. Microfluidic devices may parallelize sample preparation to the point that sample normalization (quantification and pooling) prior to sequencing is of great benefit. An exemplary microfluidic device is shown in FIGS. 1 and 2, and exemplary microfluidic architecture is shown in FIGS. 3 and 4.

Polynucleotides may be produced in a multi-step reaction in a microfluidic device, such as for sequencing library preparation. The microfluidic device may be, without limitation, an elastomeric microfluidic device or a positive displacement liquid handler. Nucleic acid may be enriched on the microfluidic device using beads, for example, RNA may be enriched by poly-A capture. Nucleic acid may be fragmented, reverse transcribed, and/or sample barcoded by PCR in the microfluidic device. Sample polynucleotides produced in the microfluidic device may include spaced inverted repeats.

Enrichment

Enrichment mechanisms include immobilization of biomolecules, such as sample nucleic acids, on a solid support within the microfluidic device. The solid support may be a fluid permeable matrix, a wall of a channel or chamber, or beads as described further herein.

Bead retention mechanisms may be based at least partially on particle contact with any suitable physical barrier(s) disposed in a microfluidic network. Such particle-barrier contact generally restricts longitudinal particle movement along the direction of fluid flow, producing flow-assisted retention. Flow-assisted particle-barrier contact also may restrict side-to-side/orthogonal (transverse) movement. Suitable physical barriers may be formed by protrusions that extend inward from any portion of a channel or other passage (that is, walls, roof, and/or floor). For example, the protrusions may be fixed and/or movable, including columns, posts, blocks, bumps, walls, and/or partially/completely closed valves, among others. Some physical barriers, such as valves, may be movable or regulatable. Alternatively, or in addition, a physical barrier may be defined by a recess(es) formed in a channel or other passage, or by a fluid-permeable membrane. Other physical barriers may be formed based on the cross-sectional dimensions of passages. For example, size-selective channels may retain particles that are too large to enter the channels. A sieve architecture may provide a plurality of openings through which fluid may flow but beads larger than the hole may be retained.

Chemical retention mechanisms may retain particles based on chemical interactions. The chemical interactions may be covalent and/or noncovalent interactions, including ionic, electrostatic, hydrophobic, van der Waals, and/or metal coordination interactions, among others. Chemical interactions may retain particles selectively and/or nonselectively. Selective and nonselective retention may be based on specific and/or nonspecific chemical interactions between particles and passage surfaces.

Such retention mechanisms may be part of a column that retains beads for enrichment of biomolecules in a unit cell.

Beads

Beads may be manufactured from inorganic materials, or materials that are synthesized chemically, enzymatically and/or biologically. Furthermore, beads may have any suitable porosity and may be formed as a solid or as a gel. Suitable bead compositions may include plastics (e.g., polystyrene), dextrans, glass, ceramics, sol-gels, elastomers, silicon, metals, and/or biopolymers (proteins, nucleic acids, etc.). Beads may have any suitable particle diameter or range of diameters. Accordingly, beads may be a substantially uniform population with a narrow range of diameters, or beads may be a heterogeneous population with a broad range of diameters, or two or more distinct diameters.

Beads may be associated with any suitable materials. The materials may include compounds, polymers, complexes, mixtures, phages, viruses, and/or cells, among others. For example, the beads may be associated with a member of a specific binding pair, such as a receptor, a ligand, a nucleic acid, a member of a compound library, an affinity reagent (such as and antibody, avidin/biotin, or a derivative thereof), and/or so on. For example, beads may be functionalized with streptavidin to bind to biotinylated molecules. In another example, beads are functionalized with (i.e., present on their surface) a chemical group such as carboxy functional groups (e.g., to bind nucleic acid). In another example, beads are functionalized with an oligonucleotide that binds nucleic acid in the sample, such as through hybridization to a poly-A sequence or target specific sequence(s). In certain aspects, beads may be functionalized with an affinity reagent, such as an antibody (e.g., or fragment thereof), aptamer, tetramer (e.g., such as an MHC or MHC-peptide), receptor (e.g., a T-cell receptor), an avidin (e.g., streptavidin) or biotin. For example, beads may be functionalized with antibodies to one or more protein targets, such as peptide/protein biomarkers or viral antigen, as described further herein. In certain aspects, beads may be functionalized with a pathogen or antigen thereof, such as a viral particle or viral antigen as described further herein. In certain aspects, beads may be functionalized with an oligonucleotide, such as a ssDNA that specifically hybridizes to a target nucleotide sequence (e.g., a specific RNA, cDNA, or gDNA sequence). In certain aspects, beads functionalized to bind different target sample biomolecules may be used in admixture for a multiplexed assay.

Beads may be magnetic to allow for ease of enrichment and/or washing in tube. Alternatively, beads may be not be magnetic (such as when they are retained through physical barriers on a microfluidic device).

Microfluidic Devices for Sample Preparation and Detection

Aspects of the methods described herein may be performed on a microfluidic device (or a fluidic device), which are themselves within the scope of the subject application. An exemplary microfluidic device is shown in FIG. 2.

Sample processing may be performed at least in part on a microfluidic device. For example, a plurality of samples may be processed in parallel on a microfluidic device (e.g., in separate unit cells), harvested, and then pooled for sequencing. The device may process at least 2, at least 4, at least 12, at least 24, at least 48, at least 96, or at least 384 different samples. Processing on the microfluidic device may include library preparation, such as formation of polynucleotide reaction products having sequencing adaptors and/or sample indexes. Depending on the application, sample processing on a microfluidic device may include one or more of biomolecule (e.g., nucleic acid) enrichment, washing, elution, fragmentation, reverse transcription (when the biomolecule is RNA), and PCR (e.g., to incorporate sequencing adaptors and/or sample barcodes such as dual indexes). Additional steps, such as cleanup, amplification, quantification for sample normalization, and/or pooling may be performed off the microfluidic device or in a downstream fluidic device.

Microfluidic devices may comprise a network of flow channels and/or may include a microliter or nanoliter scale pipetting apparatus (such as a positive displacement pipetting arm) to perform multistep reactions in a multiwell plate.

In certain aspects, enrichment may be performed on the microfluidic device. For example, the microfluidic device (e.g., a unit cell of the microfluidic device) may include a column for immobilization of target biomolecules on a solid support. In certain aspects, the column may include beads or may be configured to retain beads, and can be described as a specialized chamber. For example, beads in a column may be packed upstream of a sieve, such that the beads may be retained under flow of fluid (e.g., sample, wash solution, reagents, etc.). The beads may be functionalized with a chemical group or biomolecule for binding target biomolecules, as described further herein. Beads may be loaded into the column of the microfluidic device, after which sample (and optionally a wash solution) may be flowed across the beads. Alternatively, beads may be mixed with sample, and optionally washed, prior to injection into the microfluidic device. This alternative may improve enrichment and/or reduce sample loading time at the cost of less automation on the microfluidic device. In either case, the microfluidic device allows for bead-based enrichment to increase the amount of biomolecules processed in a unit cell (while maintaining a low amount of reagent used and allowing for parallel processing of samples in a single microfluidic device).

The microfluidic device may provide one or more sample processing sites (e.g., downstream of a column in a unit cell). For example, the device may provide at least 2, at least 3, at least 4, or at least 5 processing sites in a unit cell. The sample processing sites may be fluidically isolated from one another and/or the column during operation, such as through valves positioned along the unit cell, until a mixing step between one or more processing sites and/or the column is initiated. Mixing may be by interface free mixing or active mixing such as dilation pumping or peristaltic pumping.

The microfluidic device may enable loading of different reagents into different processing sites (e.g., prior to a mixing step). The microfluidic device may have one or more waste channel to remove excess solution, such as solution suspending beads packed into the column. A waste channel, reagent channels, and/or sample channels may share a portion of their length with one another.

Sample channels may be configured to inject sample (e.g., beads) into a first junction of a unit cell (e.g., proximal to a column). Sample may be flowed through the column and out a waste outlet to allow loading of beads and/or to pass sample biomolecules over beads in the column. Different samples may be delivered to different unit cells.

A plurality of reagent channels may be configured to introduce reagents into different sample processing sites (such as chambers of different sample processing site). Such reagents may perform any of the sample processing steps described throughout this application. At least some (e.g., or all) reagent channels may share a portion of their channel length along a shared channel, and the microfluidic device may be operated to flow a given reagent through the shared channel at different times. For example, the microfluidic device may include a multiplexor that may be operated to control which reagent inlet is used to load a processing site of the unit cell. The shared channel may deliver reagent through a second junction of the unit cell. Reagent flowed through the shared channel may be directed to different sample processing sites (e.g., via a network of valves). Alternatively, at least some reagent channels may each deliver a reagent directly to a specific sample processing site (e.g., and not through a shared channel). In certain aspects, reagent loading of multiple unit cells may be performed simultaneously and/or identically. Loading of reagents into sample processing sites may be by blind filling (e.g., where one end of the chamber or channel of the sample processing site is blocked by a closed valve or wall, or by flow of the reagent through the sample processing site and out a waste outlet.

The microfluidic device may deliver solutions to the unit cell, including wash and/or elution solutions that are flowed through the column after loading the sample, and harvest solution that is used to remove prepared sample from the device.

The microfluidic device may have additional channels and junctions for introduction and removal of such solutions. For example, a waste outlet channel may collect excess sample, reagent, and/or solutions. A harvest outlet may collect prepared sample. In certain aspects, a harvest solution may be flowed from a harvest inlet, through the unit cell, and into the sample inlet (which functions as a harvest outlet for each sample. In general, sample, reagents, solution and waste channels may share channel segments and/or junctions of entry to the unit cell, when doing so simplifies architecture and does not interfere with the sample processing reactions or result in contamination.

In one example, samples may be lysed and nucleic acids (e.g., RNA) may be immobilized on beads prior to loading the beads in a column of a microfluidic device for sample preparation. The microfluidic device may be operated to perform reverse transcription, and library preparation (including sample indexing). Library prepped samples may be harvested from the microfluidic device and then pooled. In certain aspects, pooling of the library prepped samples may be based on a sample normalization, such a suppression qPCR as described herein.

As described herein, the microfluidic device may include a plurality of valves. The valves and channels of the microfluidic device may be arranged to load sample into the column, direct different reagents (from different reagent inlets) into separate sample processing sites (e.g., chambers), isolate reaction sites, and mix fluids between reaction sites (e.g., by circulating fluids across sample processing loops).

The microfluidic device may be operated by a system, such as a controller described herein. Such as system may also comprise a thermocycler for driving reactions, such as reverse transcription and/or PCR. In certain aspects, the microfluidic device may be an elastomeric microfluidic device with elastomeric valves as described herein.

Microfluidic devices of the subject application may perform any number of assays, including but not limited to: PCR (such as endpoint PCR, digital PCR (dPCR), or quantitative PCR (qPCR)), immuno-PCR (such as immunoqPCR), proximity assay, Elisa, reverse transcription, premaplification (e.g., targeted, multiplexed targeted, or not-specific preamplification such as whole genome or whole transcriptome amplification), sample encoding/indexing, and so forth. In certain aspects, the method of detection is qPCR (i.e., real-time PCR) in which a reaction is interrogated across a number of thermal cycles such that an abundance of the target can be determined. qPCR provides a a cycle threshold (CT) that relates to the abundance of the target. qPCR methods on array microfluidic devices are described in US patent publication number US20160153026, which is incorporated herein by reference. The cycle threshold in qPCR is discussed at length in US patent publication number US20080129736 which is incorporated herein by reference.

In proximity ligation described in US patent publication number 20050003361, binding moieties are provided on proximity probes that hybridize to a splint template and are ligated. However, the binding moieties are for coupling of each probe to an affinity reagent (e.g., an antibody) and the splint template is a synthetic target (e.g., a synthetic single stranded DNA sequence) that enables ligation of the probes when their affinity reagents are bound in proximity. Proximity assays, such as proximity extension, are also described in the context of microfluidic devices in US patent publication number US20160024557, which is incorporated herein by reference. Proximity assays to detect protein targets may be performed alongside detection of RNA or DNA targets in the same sample as described further herein.

Elastomeric Microfluidic Devices

Suitable microfluidic devices include elastomeric microfluidic devices with elastomeric valves. Such elastomeric valves may be pressurized to deflect an elastomeric membrane into a flow channel of the microfluidic device, thereby controlling fluidic communication. Backpressure of inlets can drive fluids (e.g., samples, reagents, solutions, etc.) through channels that are not blocked off by closed valves.

Early disclosure of elastomeric microfluidic devices can be found in U.S. Pat. No. 7,601,270, disclosure of loop channels and peristaltic pumps can be found in U.S. Pat. No. 7,351,376, disclosure of dead end (blind) filling can be found in U.S. Pat. No. 7,766,055, disclosure of surface functionalization and immobilization can be found in U.S. Pat. No. 7,691,333, disclosure of multiplexor architecture can be found in U.S. Pat. No. 7,691,333, and disclosure in multi-step processing architecture can be found in U.S. Pat. No. 9,429,500, all of which are incorporated by reference herein.

In the context of elastomeric microfluidic devices:

A "flow channel" refers generally to a flow path through which a solution can flow.

The term "valve" unless otherwise indicated refers to a configuration in which a flow channel and a control channel intersect and are separated by an elastomeric membrane that can be deflected into or retracted from the flow channel in response to an actuation force.

An "isolated reaction site" generally refers to a reaction site that is not in fluid communication with other reactions sites present on the device. When used with respect to a blind channel, the isolated reaction site is the region at the end of the blind channel that can be blocked off by a valve associated with the blind channel.

The term "elastomer" and "elastomeric" has its general meaning as used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application.

Systems for Operating Microfluidic Devices

A system coupled to the microfluidic device may include controllers of fluid flow in the microfluidic device, such as a pneumatic controller. Alternatively or in addition, the same may include a thermocyclers for driving reactions such as lysis, nucleic acid purification, reverse transcription, and PCR in reaction sites (e.g., sample processing sites) of the microfluidic device. Disclosure of microfluidic carriers, controllers and thermocycler interfaces can be found in U.S. Pat. No. 7,704,735, which is incorporated herein by reference. For example, the carrier of a microfluidic device of the subject application may be of a similar footprint to a 96 well standard microplate (e.g., within 10% of the length and width of a 127.7 mm by 85.4 mm microplate).

Exemplary Library Preparation and Normalization Workflow

An exemplary RNA sequencing library preparation workflow is described below, aspects of which may be performed by the subject methods, devices and/or kits.

This exemplary method includes the following steps:
i) Preparing and loading RNA and reagents on a fluidic circuit, then oligo d(T) beads.
ii) Library preparation is performed on the Fluidigm 48.Atlas IFC (integrated fluidic circuit)
iii) Harvested barcoded libraries are normalized (quantified by qPCR and pooled)
iv) The pooled library is cleaned up (with Agencourt AMPure XP beads), amplified by PCR using sequencing adaptors (primers that amplify from the P5 and P7 portions of the adaptor sequences), and the pooled samples are quantified by qPCR prior to sequencing.

Library preparation of step ii) can include the below steps:
Poly(a) RNA capture on solid-phase beads
Elute and fragment poly(A) RNA
Reverse-transcribe and template-switch
Sample-barcoding PCR
Harvesting of sample libraries Quantification of barcoded libraries in step iii) can be performed according to the below workflow:
Provide A KAPA Library Quantification Kit (master mix and DNA standard) modified with a qPCR Primer Premix, and library dilution buffer (10 mM Tris-HCl, pH 8.0 with 0.05% Tween 20).
Dilute the Sample Libraries 50-Fold and aliquot 2 ul of individual samples
Run qPCR on aliquots of the samples using the modified library quantification kit
Import qPCR results into a Normalization Workbook
Pool sample libraries according to the Normalization Workbook output Splinted Ligation for Target RNA Detection Small reaction volumes may benefit from advances in sample enrichment workflows. In addition, variability in sample input and quality may lead to variable sequencing depth across pooled samples, such that the sample pool must be over-sequenced to obtain a suitable depth for poor samples, markedly increasing cost. A common solution is to quantify desired library products and normalize the amount of sample libraries added to the pool based on this quantification. Such quantification methods include traditional qPCR and mobility based methods that detect library products based on length. However, artefacts from library preparation workflows can interfere with existing methods of quantification. Improved methods of quantification may result in a multiple fold reduction in sequencing cost.

Aspects of parallel processing herein include methods and kits for splinted ligation based detection of a target nucleic acid, such as a target RNA. Splinted ligation aspects described herein may obviate the need for reverse transcription and optionally pre-amplification before detection (e.g., detection by PCR based detection such as qPCR, or detection by sequencing).

Splinted ligation has been reported by Maroney et al. in "A rapid, quantitative assay for direct detection of microRNAs and other small RNAs using splinted ligation" Rna 13.6 (2007): 930-936. Maroney reported RNA detection in which the target RNA is not the splint template and subsequent detection of the ligation product by gel electrophoresis. Splinted ligation detection by PCR has been reported by Blewett et al. in "A quantitative assay for measuring mRNA decapping by splinted ligation reverse transcription polymerase chain reaction: qSL-RT-PCR" Rna 17.3 (2011): 535-543. However, in the method reported by Blewett, the target RNA was not the splint template and the splinted ligation product required reverse transcription prior to PCR based detection. In proximity ligation described in US patent publication number 20050003361, binding moieties are provided on proximity probes that hybridize to a splint template and are ligated. However, the binding moieties are for coupling of each probe to an affinity reagent (e.g., an antibody) and the splint template is a synthetic target (e.g., a synthetic single stranded DNA sequence) that enables ligation of the probes when their affinity reagents are bound in proximity. Proximity assays, such as proximity extension, are also described in the context of microfluidic devices in US patent publication number US20160024557, which is incorporated herein by reference. Proximity assays to detect protein targets may be performed alongside detection of RNA or DNA targets in the same sample as described further herein.

None of the above publications provide methods where an endogenous nucleic acid target (e.g., an endogenous target RNA such as a genomic viral RNA or a mammalian gene transcript) in the splint template for two synthetic splint ligation probes (e.g., DNA or RNA based), thereby obviating need for reverse transcription. Further, none of the above publications disclose capture (e.g., for enrichment) of splint ligation probes on a solid support (e.g., beads) that specifically binds a binding moiety present on one or both of the probes. Still further, none of the above publications recite one or more splint ligation probes with a sample barcode for selective amplification by a sample barcode primer (e.g., that hybridizes to the sample barcode sequence or reverse complement), allowing for pooling of samples prior to detection by PCR. One or more of these distinct aspects, optionally in combination with a microfluidic device and workflow described herein, may provide unique benefit. Such aspects, and additional aspects, are discussed further herein for any suitable combination in a kit or method.

The subject splinted ligation methods and kits may offer one or more distinct advantages described below. By using the RNA target as the splint template, a reverse transcription enzymatic step may be avoided. Such a step may be inhibited in a lysate, blood, saliva, or other fluid sample. Ligase may not be inhibited, or may be less inhibited, is such a sample. Further, risk of amplicon contamination may be reduced as there is no need for off-IFC reverse transcription and preamplification (e.g., reverse transcription may be unnecessary and preamplification, if needed after the optional enrichment described below, may be performed on the IFC). Capture (e.g., enrichment) of probes comprising a binding moiety as described herein may allow for separation of the hybridization product from inhibitory components of the lysate, blood, saliva or other fluid sample prior to ligation. The hybridization scheme described herein may have a minimal footprint. For example, both probes may together hybridize a sequence of the target RNA that is less than 60 nucleotides, less than 50 nucleotides, less than 40 nucleotides, or less than 30 nucleotides in length. As such, a short or degraded RNA may be detected by this approach, where a traditional PCR of a larger segment or poly-A based enrichment and/or reverse transcription, would not be suitable. Such RNA may have been degraded by fixation (such as in FFPE tissue) or in the bodily fluid sample (such as degradation of viral RNA in saliva). In microfluidic (e.g., IFC) based workflows, capture on the microfluidic device as described herein may provide enrichment of the target RNA, hybridization product, and/or ligation product in the reaction sites of the IFC. Such reaction sites may have volume(s) less than 1 ul, less than 500 nl, less than 200 nl, less than 100 nl, less than 50 nl, or less than 20 nl. As formation of a ligation product requires binding of two probes adjacent to one another, this method provides high specificity. Sample barcoded probes allow sample to be pooled prior to steps such as ligation and/or preamplification to allow uniform sample handling and increase parallel sample processing. Individual samples may be interrogated by sequencing ligation product in pooled samples or by separating the pooled sample into separate reaction volumes and performing sample specific PCR (e.g., qPCR) using one or more sample barcode primers as described herein. For example, pooled sample may be split into different reaction volumes (e.g., reaction sites on an array IFC) and target RNA from individual samples may be detected by using different sample barcode primers to amplify the ligation product from different samples in different reaction sites. Such sample barcoded primers may be input through assay inlets of an array IFC as described herein, and the pooled sample may be input through a sample inlet and optionally captured and/or pre-processed on the microfluidic device upstream of the array. Detection on an array IFC may enable parallel sample processing, automation and uniform sample processing, as well as small reaction volumes which results in lower reagent costs.

Splinted Ligation with Target Nucleic Acid Splint Template

In certain aspects, the target nucleic acid may be an endogenous DNA or RNA. Endogenous target RNA may be viral RNA (e.g., genomic viral RNA) or of a mammalian species, such a gene transcript or non-coding RNA from a human, non-human primate, or rodent subject. Samples could be cell lysates (e.g., from cell culture or from tissue), cell-free nucleic acids (e.g., from a bodily fluid), or purified nucleic acids, e.g., as described further below.

For example, the target RNA may be a genomic viral RNA, such as of a respiratory virus (e.g., syncytial virus, influenza virus, parainfluenza virus, metapneumovirus, rhinovirus, and coronavirus). In such cases, a sample from a subject (e.g., a human) may be taken to determine viral infection. The sample may be saliva, nasal swab, blood, or an extracted component thereof. In certain aspects, the viral RNA may be partially degraded (such as in a saliva sample) and difficult to detect by traditional reverse transcription and PCR amplification.

In another example, the target RNA may be an endogenous mammalian (e.g., rodent, non-human primate, or human) RNA. The mammalian RNA may be a gene transcript or a non-coding RNA, such as ribosomal RNAs (rRNAs), as well as small RNAs such as microRNAs, siRNAs, piRNAs, snoRNAs, snRNAs, exRNAs, scaRNAs, or ncRNAs. In certain aspects, the RNA may be fragmented, such as by FFPE fixation and/or long term storage. As such, viral infection and/or strain, and optionally further viral load, may be detected using splinted ligation methods and/or kits described herein.

While detection of RNA may typically require RNA extraction, reverse transcription and/or preamplification (e.g., of viral cDNA), the subject splinted ligation embodiments described herein may obviate one or more of these steps, thus reducing assay cost and/or increasing parallelization of sample analysis. As such, genotyping or gene expression may be detected using splinted ligation methods and/or kits described herein.

In the subject splinted ligation methods and kits, the target RNA acts as a splint. As a target RNA of interest is usually known (e.g., based on a sequenced, and publically available, viral or mammalian genome or transcriptome), splint ligation probes (simply referred to as "probes" in the context of splint ligation herein) may be designed to specifically hybridize the target RNA adjacent to one another such that a 3'-OH end of a first probe is next to a 5'-PO4 end of the second probe. Such hybridization forms a splint hybridization product (simply referred to as a "hybridization product" in the context of splint ligation herein), and can be described as having a nick between the 3'-OH and 5'-PO4 ends of the first and second probe respectively.

Splint ligation probes may be DNA or RNA based. DNA based probes may allow PCR amplification. Probes may each hybridize to a an adjacent sequence on the target nucleic acid, such as a sequence between 10 and 30 nucleotides long, between 15 and 25 nucleotides long, less than 40 nucleotides, less than 30 nucleotides long, less than 25 nucleotides long, less than 20 nucleotides long, or less than 15 nucleotides long. A probe may have a binding moiety (e.g., attached to the end that is not ligated). Such a probe may have a cleavage site to enable separation from a solid support (e.g., before preamplification and/or detection by sequencing or PCR). Alternatively or in addition, a probe may have a sample barcode for selective amplification of ligation products formed in a specific sample, as described further herein.

Ligation of said probes in the hybridization product may be by a suitable ligase, and forms a splint ligation product (simply referred to as a "ligation product" in the context of splint ligation herein). Such ligation may be by any suitable ligase. For example, if the probes are DNA probes, a ligase such as T4 ligase or PBCV-1 ligase, which has been shown to ligated nicked DNA on DNA-RNA hybrids by Lohman et al. in "Efficient DNA ligation in DNA-RNA hybrid helices by *Chlorella* virus DNA ligase" *Nucleic acids research* 42.3 (2014): 1831-1844.

The target nucleic acid may be DNA or RNA. Further, the splint ligation probes may comprise DNA and/or RNA. As such, the hybridization product may be a DNA-DNA, RNA-RNA, or DNA-RNA hybrid. Ligases suitable for the hybridization product may be chosen by one of skill in the art.

Figure 10A:
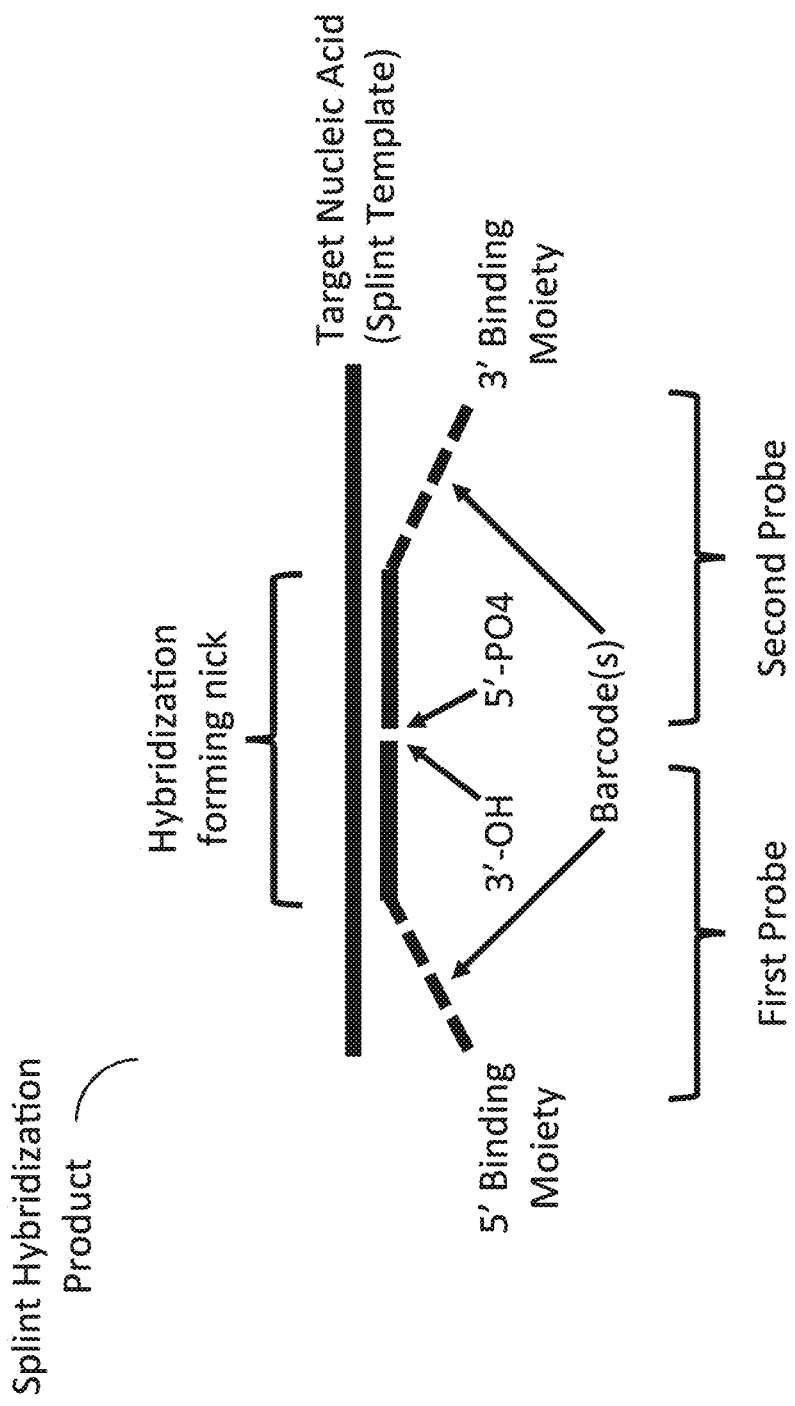
FIGS. 10A and 10B shows an exemplary splint hybridization product and splint ligation product respectively.
Figure 10B:
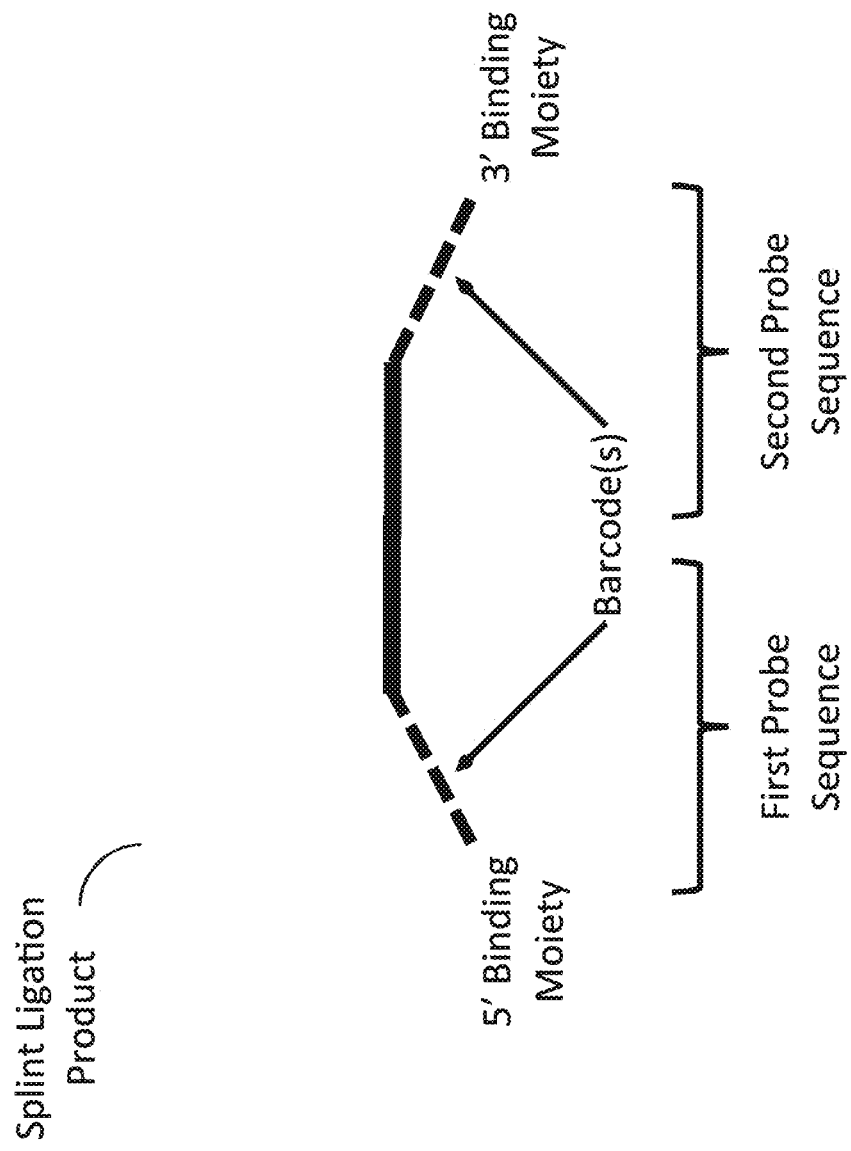

FIGS. 10A and 10B shows an exemplary splint hybridization product and splint ligation product respectively. FIG. 10A shows an exemplary splint hybridization product of the subject application in which the target nucleic acid (e.g., a DNA or RNA, such as an endogenous mammalian or viral RNA) acts as the splint template. Two probes specifically hybridize to adjacent sequences of the target nucleic acid, such that a 3'-OH end of the first probe is adjacent to a 5'-PO4 end of the second probe. One or both of the probes may further have a barcode sequence, such as a sample barcode. One or both of the probes may have a binding moiety (e.g., to allow for capture on a solid support such as beads, such as for enrichment and/or purification). Such capture may be of the hybridization product, followed by ligation of the captured hybridization product. Alternatively, such capture may be of the ligation product formed upon ligation in solution. FIG. 10B shows an exemplary splint ligation product formed from ligation of the two probes at the adjacent region (i.e., nick). The target nucleic acid may still be hybridized to the ligation product, or may be degraded (or allowed to degrade, such as degradation of target RNA by heat, RNAse, or any suitable means). The probes may be DNA or RNA. For example, DNA probes may allow for subsequent PCR of the ligation product.

Figure 11:
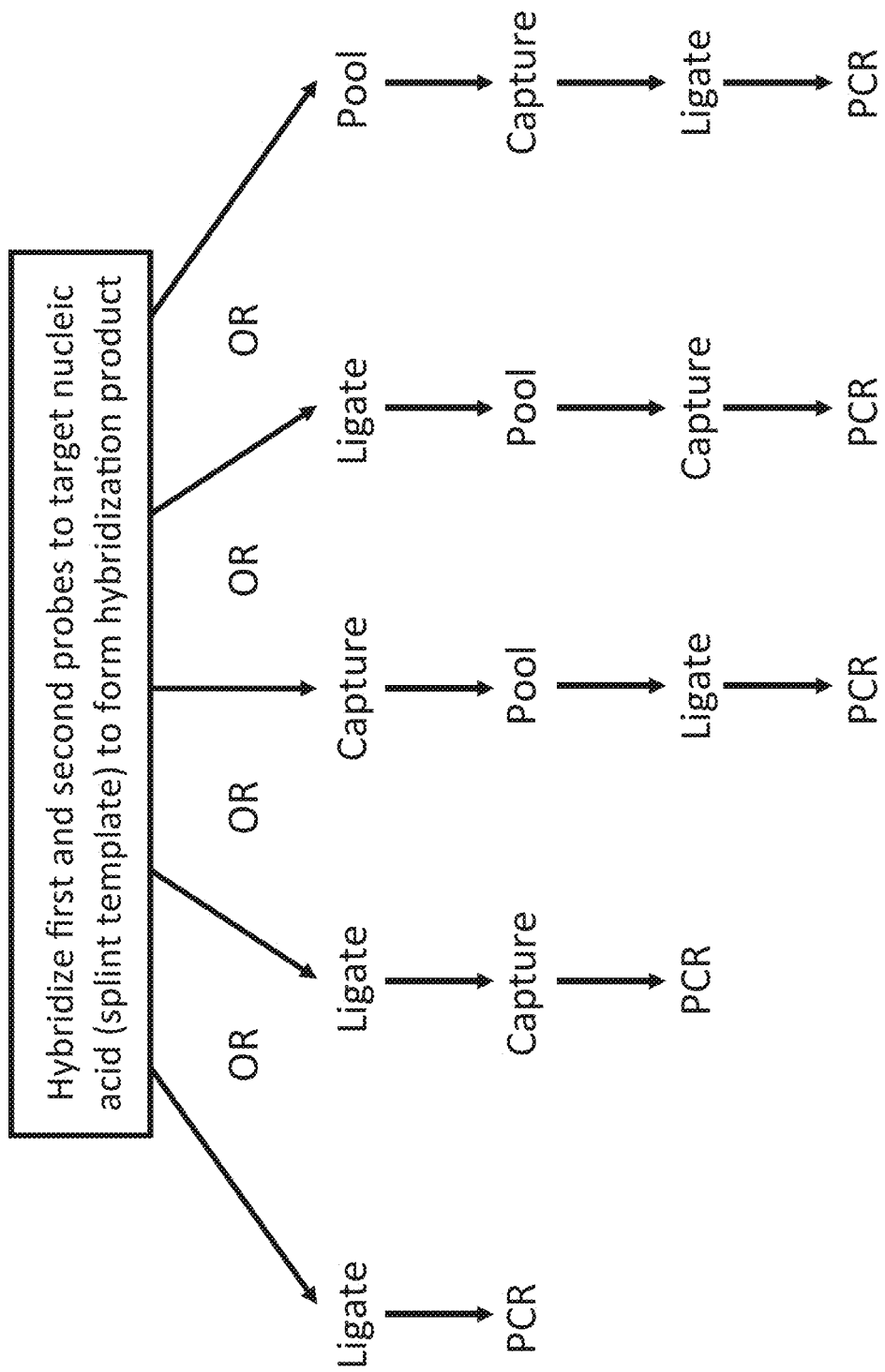
FIG. 11 shows exemplary splinted ligation workflows.

FIG. 11 shows exemplary splinted ligation workflows. In all such methods, a hybridization product is formed by hybridization of two probes to a target nucleic acid (e.g., target RNA) that acts as a splint template. Ligation of the probes in the hybridization product forms a ligation product. Detection of the target nucleic acid may be by sequencing of the ligation product sequence, or by PCR (e.g., qPCR) of the ligation product as shown in FIG. 11. In certain aspects, such as shown in the leftmost workflow, the hybridization product is ligated and then detected by PCR without capture or pooling. In certain aspects, such as shown in the middle-left workflow, hybridization product is ligated and then captured on a solid support (e.g., enriched and/or purified) prior to detection by PCR. Of note, the capture step may be performed before the ligation step, such as when ligation is performed when the hybridization product is still bound to a solid support. In certain aspects, such as shown in the middle, middle-right, and rightmost workflow, at least one probe may have a sample barcode allowing hybridization products or ligation products to be pooled. The pool may be separated (e.g., after steps such as ligation, capture, and/or preamplification) and ligation production from different samples may be detected in different reaction volumes using sample barcode primers. For example, hybridization products may be captured, then pooled, and then ligated prior to detection by PCR as shown in the middle workflow. In another example, hybridization products may be ligated, then pooled, and then captured prior to PCR as shown in the middle-right workflow. In another example, hybridization products may be pooled, then captured, and then ligated prior to PCR as shown in the right workflow. In certain aspects, capture, ligation, preamplification, splitting of a pool, and/or PCR detection may be performed in on a microfluidic device, such as a device comprising a column and/or array IFC. For example, capture of hybridization products or ligation products may be on beads that are then flowed into a sieve architecture on a microfluidic device to form a column, or capture may be by flowing hybridization products or ligation products over beads already loaded in a column of the microfluidic device. Detection may be on an array IFC, such as when ligation products are formed for different targets and/or in different samples, as described further herein.

In certain aspects, ligation and preamplification may be performed in the same reaction step or reaction volume, such as on a microfluidic device or in a tube.

Splinted Ligation Methods and Kits

The subject application includes the following aspects:
1. A method of library normalization comprising:
   a. obtaining aliquots from a plurality of samples, wherein the samples comprise polynucleotides comprising spaced inverted repeats;
   b. performing suppression PCR on the aliquots of step a;
   c. quantifying amplification products from step b;
   d. pooling the plurality of samples to form a library normalized based on the quantification of step c; and wherein the pooled plurality of samples have not undergone the suppression PCR of step b.
2. The method of aspect 1, wherein the plurality of samples comprise at least 8 samples.
3. The method of aspect 1, wherein the samples are library prepped for sequencing.
4. The method of aspect 1, wherein the sample is derived from fixed tissue.
5. The method of aspect 1, wherein suppression PCR is with a primer comprising a sequence identical to at least 8 nucleotides of a spaced inverted repeat.
6. The method of aspect 1 or 5, wherein the sequence identical to the spaced inverted repeat is at the 3' end of the primer.
7. The method of aspect 6, wherein the primer comprises a 5' sequence that is not complementary to the polynucleotide but that increases suppression of short amplicons over long amplicons produced in earlier PCR cycles.
8. The method of aspect 7, wherein the 5' sequence is at least 6 nucleotides long.
9. The method of aspect 1, wherein suppression PCR is with only one primer.
10. The method of aspect 1, wherein the samples are pooled to normalize for read uniformity.
11. The method of aspect 1, wherein the pooled plurality of samples have not undergone suppression PCR
12. The method of aspect 1, wherein the suppression PCR enriches for amplicons with more than 200 nucleotides between inverted repeats at least 25 fold more than amplicons shorter than 50 nucleotides between inverted repeats.
13. The method of aspect 1, wherein suppression PCR is with only one primer.
14. The method of aspect 1, wherein suppression PCR is with two different primers both comprising a 3' sequence identical to at least 8 nucleotides of a spaced inverted repeat.
15. The method of aspect 1, wherein quantification is by qPCR.
16. The method of aspect 1, wherein quantification is based on a dilution series of a library quantification standard 17. The method of aspect 16, wherein the length of the library quantification standards is between 150 and 800 nucleotides.
18. The method of aspect 1 or 15, further comprising melting curve analysis of the amplification products from step b.
19. The method of aspect 1 or 3, wherein the polynucleotides comprise cDNA.
20. The method of aspect 1 or 3, wherein the polynucleotides comprise gDNA.
21. The method of aspect 1 or 3, wherein polynucleotides comprise sample barcodes.
22. The method of aspect 21, wherein the polynucleotides comprise dual indexes.
23. The method of aspect 1, wherein polynucleotides comprises spaced inverted repeats flanking an insert of variable length.
24. The method of aspect 1, wherein the insert is cDNA.
24. The method of aspect 1, wherein the polynucleotides comprise exactly two spaced inverted repeats of length 8 nucleotides or more.
25. The method of aspect 1 or 24, wherein the spaced inverted repeats are within 50 nucleotides of their respective ends.
26. The method of aspect 25, wherein the spaced inverted repeats are terminal.
27. The method of aspect 1, wherein the spacing of the inverted repeats is variable.
28. The method of aspect 1, wherein the polynucleotides comprise a sequencing adaptor comprising a spaced inverted repeat.
29. The method of aspect 1 or 28, wherein the polynucleotides of the sample comprise Illumina p5 and p7 sequencing adaptors.
30. The method of aspect 28, wherein the spaced inverted repeats are at least 8 nucleotides long.

31. The method of aspect 1, wherein at least one sample has an average polynucleotide length of less than half of the average polynucleotide length across the samples.
32. The method of aspect 1, further comprising producing the polynucleotides prior to step a.
33. The method of aspect 32, wherein producing the polynucleotides comprises 3' enrichment.
34. The method of aspect 32, wherein producing the polynucleotides comprises bead based enrichment of the polynucleotides.
35. The method of aspect 32, wherein producing the polynucleotides comprises reverse transcription.
36. The method of aspect 32 or 35, wherein producing the polynucleotides comprises tailing and template switching.
37. The method of aspect 32 or 33, wherein producing the polynucleotides comprises fragmentation.
38. The method of aspect 32, wherein producing the polynucleotides comprises random priming.
39. The method of aspect 32, wherein producing the polynucleotides comprises ligation that adds spaced inverted repeats to the polynucleotide.
40. The method of aspect 32, wherein producing the polynucleotides comprises PCR introduction of sample barcode.
41. The method of aspect 32 or 40, wherein producing the polynucleotides comprises PCR introduction of spaced inverted repeats.
42. The method of aspect 32, wherein the polynucleotides are produced from RNA.
43. The method of aspect 32, wherein the polynucleotides are produced from gDNA.
44. The method of aspect 32, wherein the polynucleotides are produced in a multi-step reaction in a microfluidic device.
45. The method of aspect 44, wherein the microfluidic device is an elastomeric microfluidic device.
46. The method of aspect 44 or 45, wherein nucleic acid is enriched on the microfluidic device using beads.
47. The method of aspect 46, wherein RNA is enriched by poly-A capture.
48. The method of aspect 47, wherein poly(A) RNA is fragmented, reverse transcribed, and resulting cDNA is sample barcoded by PCR in the microfluidic device
49. The method of aspect 44, wherein the polynucleotides are produced in a multi-step reaction performed by a positive displacement liquid handler.
50. The method of aspect 1, further comprising sequencing polynucleotides of the pooled plurality of samples.
51. The method of aspect 50, wherein sequencing is whole genome sequencing, whole transcriptome sequencing, target specific sequencing, or chromatin accessibility sequencing.
52. The method of aspect 50, wherein the library normalization improves read depth uniformity across pooled samples.
53. The method of aspect 50, wherein library normalization results in at least a two-fold reduction in read depth variation as compared to normalization based on qPCR quantitation but not suppression qPCR.
54. The method of aspect 50, wherein library normalization results in at least a two-fold reduction in sequencing cost as compared to normalization based on qPCR quantitation but not suppression qPCR.
55. The method of aspect 50, wherein sequencing cost is the cost needed to achieve adequate read depth of all samples in the pool.
56. The method of aspect 50, wherein adequate read depth is at least 5000 reads.
57. The method of aspect 50, fewer than 5% of the samples are at a read depth less than 50% of the average read depth across samples.
58. The method of aspect 57, wherein no samples are at a read depth less than 50% of the average read depth across samples
59. The method of aspect 50, wherein more than 5% of the samples would be at a read depth of less than 50% of the average read depth across samples, if the library were not normalized.
60. The method of aspect 59, wherein at least some samples would be at a read depth of less than 25% of the average read depth across samples, if the library were not normalized.
61. The method of aspect 60, wherein all samples in the normalized library have more than 5000 genes detected.
62. The method of aspect 61, wherein at least some samples would have fewer than 2500 genes detected if the library were not normalized
63. A kit for library quantification of polynucleotides by suppression qPCR, the kit comprising:
a library quantification standard comprising spaced inverted repeats separated by at least 150 nucleotides; and
a primer comprising a sequence identical to at least 8 nucleotides of one of the inverted repeats.
64. The kit of aspect 63, wherein the primer can, in the presence of master mix and polymerase, amplify the library quantification standard at 1.75 or greater efficiency per cycle, but will amplify sample polynucleotides comprising inverted repeats spaced by 50 nucleotides or less at 1.5 or less efficiency in per cycle.
65. The kit of aspect 64, wherein the primer can, in the presence of master mix and polymerase, amplify polynucleotides comprising inverted repeats spaced 200 or more nucleotides apart at 0.25 or greater cycle efficiency than polynucleotides comprising inverted repeats spaced 50 nucleotides or less.
66. The kit of aspect 63, wherein the library quantification standard comprises sequencing adaptors that comprise the inverted repeats.
67. The kit of aspect 63, wherein the kit further comprise adaptors that introduce spaced inverted repeats.
68. A kit for library preparation and quantification, comprising:
adaptors together providing inverted repeats at least 8 nucleotides in length; and
a primer comprising a sequence identical to at least 8 nucleotides of an inverted repeat.
69. The kit of aspect 68, wherein the primer can, in the presence of master mix and polymerase, amplify sample polynucleotides comprising inverted repeats spaced 200 or more nucleotides apart at 0.25 or greater cycle efficiency than sample polynucleotides comprising inverted repeats spaced 50 nucleotides or less.
70. The kit of aspect 68, wherein the primer can, in the presence of master mix and polymerase, amplify the library quantification standard at 1.8 or greater efficiency per cycle, but will amplify sample polynucleotides comprising inverted repeats spaced by 50 nucleotides or less at 1.5 or less efficiency in per cycle.

71. The kit of aspect 63 or 68, wherein the sequence identical to the spaced inverted repeat is at the 3' end of the primer.
72. The kit of aspect 63 or 68 or 71, wherein the primer comprises a 5' sequence that is not complementary to the polynucleotide but that increases suppression of short amplicons over long amplicons produced in earlier PCR cycles.
73. The kit of aspect 72, wherein the 5' sequence is at least 6 nucleotides long.
74. The kit of aspect 63 or 68, wherein the primer is sufficient for suppression PCR of polynucleotides comprising the spaced inverted repeats.
75. The kit of aspect 63 or 68, further comprising a different primer comprising a sequence identical to at least 8 nucleotides of a spaced inverted repeat but comprising a different 5' sequence from the primer.
76. The kit of aspect 68, wherein the adaptors comprise a sample barcode.
77. The kit of aspect 68 or 76, wherein the adaptors comprise dual indexes.
wherein library prepped polynucleotides produced with the adapters comprise spaced inverted repeats
78. The kit of aspect 68, further comprising beads for enriching nucleic acids on a microfluidic device.
79. The kit of aspect 78, wherein oligonucleotides comprising a 3' poly-T sequence are bound to the beads.
80. The kit of aspect 68, 69 or 70, further comprising a microfluidic device for bead based enrichment of target nucleotide sequences.
81. The kit of aspect 80, wherein the microfluidic device has a series of reaction sites for multi-step sequencing library preparation.
82. The kit of aspect 68 or 80, further comprising reagents for reverse transcription.
83. The kit of aspect 63 or 68, further comprising a passive reference dye
84. The kit of aspect 63 or 68, further comprising a PCR master mix for performing the qPCR.
85. A kit for performing any one of method aspects 1 to 62. 86. A method comprising library normalization based on suppression qPCR.
87. A method comprising suppression qPCR.
88. A method comprising sequencing a library normalized by suppression qPCR.
89. A pool of samples normalized based on suppression qPCR of any one of aspects 1 to 62.
90. A method of processing a splint hybridization product, comprising:
a) hybridizing a first probe and a second probe to a target nucleic acid to form a hybridization product, wherein a 3'-OH end of the first probe is adjacent to a 5'-PO4 end of the second probe, and wherein at least one of the first probe and the second probe comprises a binding moiety;
b) capturing the hybridization product by specifically binding the binding moiety to a solid support.
91. The method of aspect 1, wherein the target nucleic acid is a target RNA.
92. The method of aspect 2, wherein the target RNA is a genomic viral RNA.
93. The method of aspect 3, wherein the target RNA is a mammalian gene transcript.
94. The method of any one of aspects 90 to 93, wherein the solid support comprises beads.
95. The method of any one of aspects 90 to 94, wherein the solid support is on a column of a microfluidic device.
96. The method of any one of aspects 90 to 95, further comprising ligating the hybridization product after capturing the hybridization product.
97. The method aspect 96, further comprising separating the ligation product from the solid support.
98. The method of any one of aspects 90 to 95, wherein at least one of the first probe and the second probe comprises a sample barcode.
99. The method of aspect 96 or 97, wherein at least one of the first probe and the second probe comprises a sample barcode.
100. The method of aspect 99, further comprising combining hybridization products from different samples to form a pool of samples, before or after step b) of capturing.
101. The method of aspect 100, further comprising detecting target nucleic acid of different samples by separating the pool of samples into separate reaction volumes, and further comprising PCR amplification of the ligation product of different samples in different reaction volumes using sample barcode primers.
102. The method of aspect 101, wherein the PCR amplification is on an array IFC.
103. The method of any one of aspects 90 to 99, further comprising detecting the target nucleic acid by PCR amplification of the ligation product.
104. The method of aspect 102 or 103, wherein the PCR amplification is quantitative PCR.
105. The method of aspect 102 or 103, wherein the PCR amplification is endpoint PCR.
106. A method of detecting a splint ligation product, comprising:
a) hybridizing a first probe and a second probe to a target nucleic acid to form a hybridization product, wherein a 3'-OH end of the first probe is adjacent to a 5'-PO4 end of the second probe;
b) ligating the first probe and second probes to form a ligation product;
c) detecting the presence of the ligation product.
107. The method of aspects 106, further comprising capturing the hybridization product or the ligation product on a solid support.
108. The method of aspect 107, wherein the hybridization product is captured on the solid support prior to step b) of ligating.
109. The method of aspect 107, wherein the ligation product is captured on the solid support.
110. The method of any of aspects 107 to 109, wherein the solid support comprises beads.
111. The method of aspect 110, wherein the beads are on a microfluidic device, or wherein the beads are loaded onto a microfluidic device after said capturing.
112. The method of aspect 111, further comprising PCR amplification of the ligation product in the microfluidic device.
113. The method of any of aspects 107 to 112, wherein the first probe comprises a binding moiety on its 5' end and/or the second probe comprises a binding moiety on its 3' end.
114. The method of aspect 113, wherein the binding moiety is biotin or a derivative thereof and the solid support comprises avidin or streptavidin.
115. The method of aspect 114, further comprising separating the ligation product from the solid support.

116. The method of aspect 115, wherein separation of the ligation product from the solid support is on a microfluidic device, and wherein the solid support is beads in a column on the microfluidic device.
117. The method of any one of aspects 106 to 116, wherein step c) of detecting is by PCR amplification.
118. The method of aspect 117, wherein the PCR amplification is endpoint PCR.
119. The method of aspect 117, wherein the PCR amplification is quantitative PCR.
120. The method of any one of aspects 117 to 120, wherein the PCR amplification is on an array IFC.
121. The method of any one of aspects 1 to 116, wherein at least one of the first probe and the second probe comprises a sample barcode.
122. The method of aspect 121, further comprising pooling hybridization products or ligation products from different samples.
123. The method of aspect 122, further comprising pre-amplifying the pooled ligation products by PCR.
124. The method of aspect 122 or 123, further comprising separating the pool into a plurality of reaction sites and detecting ligation products of different samples in different reaction sites, and wherein step c) of detecting comprises using sample barcode primers for PCR amplification.
125. The method of aspect 124, wherein step c) of detection comprises qPCR using a first primer that hybridizes to the sample barcode and a second primer that hybridizes target specific sequence or barcode of the ligation product, and wherein a plurality of ligation products from different target RNAs and different samples are detected in separate reaction sites
126. The method of aspect 124 or 125, wherein the PCR amplification is endpoint PCR.
127. The method of aspect 124 or 125, wherein the PCR amplification is quantitative PCR.
128. The method of aspect 122, wherein step c) of detecting is by sequencing of ligation products in the pooled samples.
129. The method of any one of aspects 106 to 128, wherein the target nucleic acid is a target RNA.
130. The method of aspect 129, wherein the target RNA is a viral RNA.
131. The method of aspect 129, wherein the target RNA is a mammalian gene transcript.
132. The method of any one of aspects 106 to 131, wherein a plurality of different target nucleic acids are each hybridized by a unique pair of two probes in step a) prior to hybridization of each pair of probes to form different ligation products in step b).
133. The method of aspect 132, further comprising detecting ligation products from different target nucleic acids by qPCR in different reaction sites.
134. The method of aspect 133, wherein the different reaction sites are on an array integrated fluidic circuit.
135. The method of aspect 134, further comprising separately detecting ligation products from different samples using different sample barcode primers in different reaction sites.
136. The method of any one of aspects 106 to 135, further comprising capturing hybridization products or ligation products on a solid support in a microfluidic device.
137. The method of aspect 136, further comprising amplifying the ligation product of different samples and/or target RNAs in separate reaction sites in an array of the microfluidic device.
138. The method of any one of aspects 106 to 137, wherein at least one of the first and second probes are DNA probes.
139. The method of any one of aspects 106 to 138, wherein the target nucleic acid is RNA and wherein the method does not include reverse transcription of the target RNA.
140. A splint ligation detection kit, comprising:
    a first probe and a second probe that each hybridize to a target nuclic acid to form a hybridization product, wherein a 3'-OH end of the first probe is adjacent to a 5'-PO4 end of the second probe,
    wherein the first probe comprises a binding moiety on its 5' end and/or the second probe comprises a binding moiety on its 3' end.
141. The kit of aspect 140, wherein the target nucleic acid is target RNA.
142. The kit of aspect 141, wherein the target RNA is a viral RNA.
143. The kit of aspect 143, wherein the target RNA is a mammalian gene transcript.
144. The kit of any one of aspects 140 to 143, wherein the binding moiety is biotin or a derivative thereof.
145. The kit of any one of aspects 140 to 144, further comprising a solid support that specifically binds the binding moiety.
146. The kit of any one of aspects 140 to 145, further comprising a ligase.
147. The kit of any one of aspects 140 to 146, further comprising a reagent for separating a captured hybridization product or ligation product from the solid support.
148. The kit of any one of aspects 140 to 147, further comprising a plurality of primers that specifically amplify a ligation product under PCR conditions 149. The kit of aspect 148, wherein at least some of the primers are sample barcode primers.
150. The kit of aspect 149, wherein the kit comprises a plurality of separated probes that each comprise a different sample barcode.
151. The kit of any one of aspects 140 to 150, wherein the kit comprises a plurality of probe pairs that each hybridize to different target RNAs, optionally wherein different probe pairs are in mixture.
152. The kit of aspect 151, further comprising target specific primers that specifically amplify ligation product formed from different target RNA's, optionally wherein the target specific primers are in mixture.
153. The kit of any one of aspects 140 to 152, further comprising a microfluidic device comprising a column for bead based enrichment of the hybridization product or a ligation product formed from the hybridization product.
154. The kit of aspect 153, wherein the microfluidic device comprises a series of reaction sites for multi-step sample processing of ligation product.
155. The kit of aspect 153 or 154, wherein the microfluidic device further comprises an array of reaction sites downstream of the series of reaction sites, wherein each reaction site in the array is configured to mix a different processed sample with reagents from a different assay inlet.
156. The kit of any one of aspects 140 to 152, further comprising an array IFC.

Capture Based Enrichment

Aspects include capture of splint hybridization products or splint ligation products on a solid support. The solid support may include beads, a column on a microfluidic device (e.g., packed with beads), a matrix, or a planar array. Beads may be any suitable material, e.g., as described elsewhere herein.

The solid support (e.g., beads) may be functionalized to specifically bind a binding moiety of a probe (e.g., incorporated into a hybridization product or ligation product by one or both probes). In certain aspects, the binding may be by affinity or by covalent binding. For example, the probe may comprise biotin or a derivative thereof, and a bead may comprise avidin or streptavidin (or visa versa). In certain aspects the binding may be covalent, such as through thiol reactive chemistry, amine reactive chemistry, or click chemistry (e.g., between TCO and tetrazing, or DBCO and azide). As such, the binding moiety may be an affinity reagent or analyte, or a covalent binding moiety. Alternatively, a probe may be attached to the bead prior to hybridizing to the target nucleic acid to enable capture of a hybridization product on the bead. Alternatively, a probe may comprise an anchor sequence that hybridizes to an oligonucleotide provided by the solid support (e.g., the bead).

A probe may have a binding moiety (e.g., attached to the end that is not ligated). Such a probe may have a cleavage site to enable separation from a solid support (e.g., before preamplification and/or detection by sequencing or PCR).

Bead based capture of hybridization products or ligation products may be performed "in tube" (i.e., off a microfluidic device such as in individual tubes or in microwell plates). After such capture, beads may be flowed into a microfluidic column for additional processing on the microfluidic device. In certain aspects, beads may be loaded into a column on a microfluidic device, and hybridization product or ligation product may be flowed through the column to enrich for the product. The microfluidic device may comprise a column and downstream sample processing site(s) such as discussed elsewhere herein and shown in FIG. 3 or 4. Ligation may occur in tube or, when captured hybridization product is in a microfluidic device, may be performed in the microfluidic device.

Aspects may include providing bead bound to hybridization product or ligation product, as described above. Such product may be separated from bead prior to addition processing (e.g., prior to ligation in the case of a hybridization product, prior to preamplifciation, and/or prior to PCR amplification for detection). Separation may be mediated by chemical or enzymatic cleavage, such as cleavage of dU on the probe by UDG (also referred to as UNG) and/or cleavage by an endonuclease such as APE1. Such a probe may comprise DNA (e.g., other than the dU sequence proximal to a binding moiety). Alternatively or in addition, separation may be mediated by heat. Alternatively, separation may be by displacement, such as displacement by free biotin of a desthiobiotin binding moiety bound to avidin or streptavidin on the bead (or visa versa). Alternatively or in addition, probes and/or beads may comprise linker (e.g., a PEG linker) to space the hybridization product or ligation product from the surface of the bead.

As described further herein, samples may be sample barcoded and pooled before or after capture. The above capture methods and reagents may be used for capture for applications outside of splinted ligation, such as applications described elsewhere herein.

Barcoded Splint Ligation Probes and Pooling

In certain aspects, one or more splint ligation probes may comprise a barcode, such as a sample barcode. Such a probe is shown in the hybridization product of FIG. 10A, and may optionally comprise a binding moiety and/or additional components described herein.

The sample barcode may be between 5 and 30 nucleotides, such as between 10 and 25 nucleotides, in length. The sample barcode(s) may be incorporated into the ligation product such that it is flanking the site of hybridization to the target nucleic acid. Barcoded samples (e.g., barcoded hybridization products or ligation products) may be pooled prior to certain steps, such as ligation, capture, preamplification, and/or detection (e.g., by sequencing or PCR, such as qPCR). Detection by PCR may involve separating pooled sample (e.g., that has been captured, ligated and/or preamplified after pooling) into separate reaction volumes, and separately detecting ligation product from different samples using sample barcode primers in different reaction volumes. Sample barcode primers may hybridize to the sample barcode or its reverse complement. In certain aspects, separation may be into reaction sites of an IFC array, and different sample barcode primers may be flowed into the array through different assay inlets. Assay specific primers that bind an assay barcode or target nucleic acid sequence (or its complement) may be used, e.g., in combination with sample barcode primers to detect a different combination of a target and sample in separate reaction sites. Array IFCs and sample barcoding for detection by PCR is described in US publication number US20100120038, and is incorporated by reference in its entirety. Pooled sample may be prepared in tube and flowed into the array directly from sample inlets, or may be flowed from a unit cell comprising a column and/or processing sites such as that shown in FIG. 3 or 4.

Sample barcoding and/or pooling may be combined with other aspects, such as capture, described herein.

Microfluidic Automation and Parallel Processing

Figure 12:
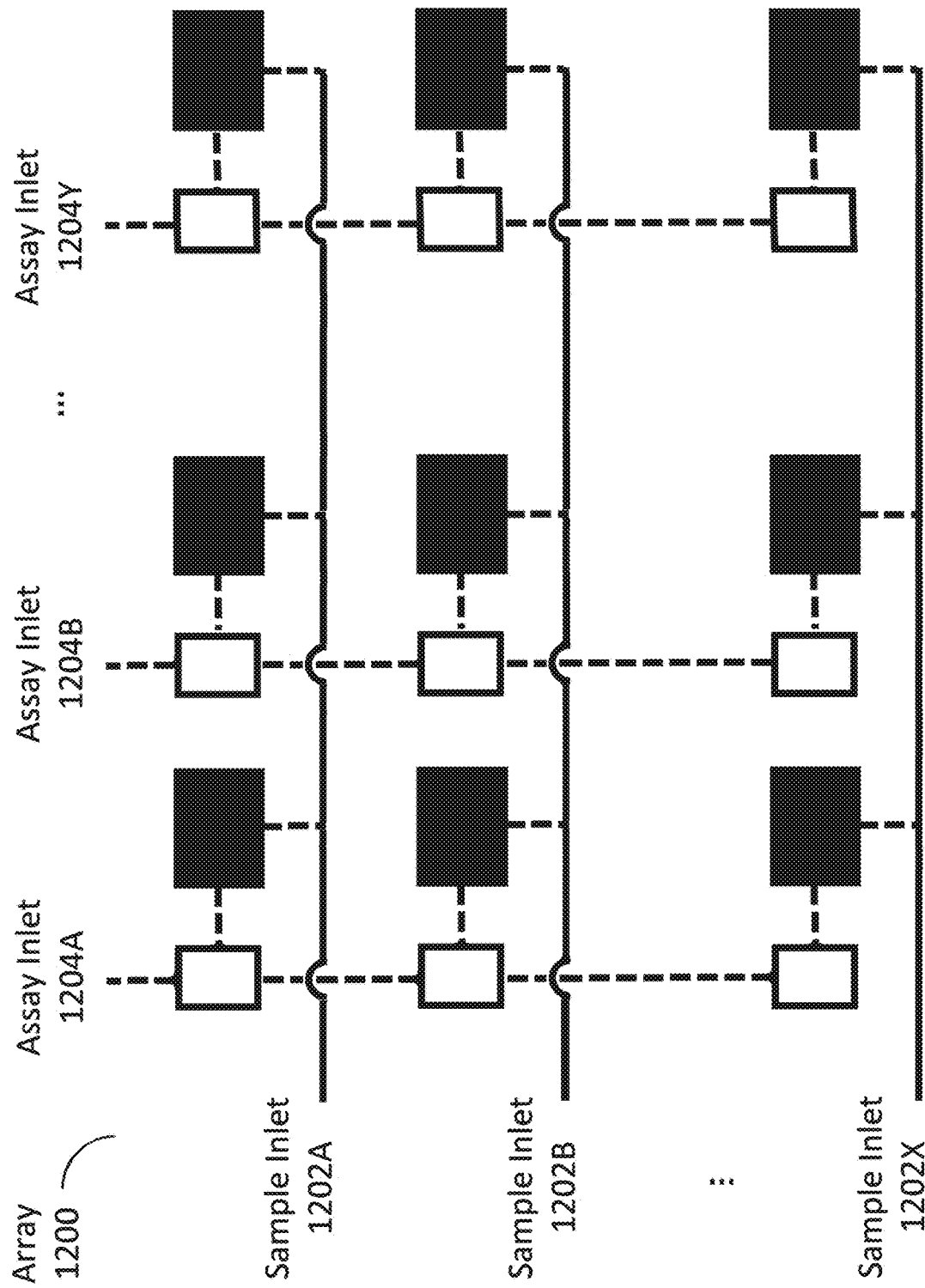
FIG. 12 is a schematic of an array integrated fluidic circuit (IFC).

FIG. 12 is a schematic of an array integrated fluidic circuit (IFC). As shown, a plurality of sample inlets 1202A-X provide sample to sample chambers (black boxes). A plurality of assay inlets 1204A-Y provide assay reagents (e.g., primers and optionally additional PCR components such as polymerase, dNTPs and/or cofactors) to assay chambers (white boxes). Sample inlets to the array may be directly from wells loaded from a user, or may be downstream of a column and/or sample preprocessing sites as described herein and shown in FIG. 3 or 4. In certain aspects, assay inlets may provide different target specific primers.

Such an array may be integrated (in fluidic communication) with unit cells for sample capture and/or processing, such as the unit cells shown in FIG. 3 or 4. Alternatively, sample obtained from a microfluidic device shown in FIG. 3 or 4, or prepared in tube off any microfluidic device, may be harvested and input to a separate array IFC.

The array IFC may have multiple layers such that sample and assay flow channels can pass over one another. The array IFC may be elastomeric (e.g., comprise an elastomer such as PDMS), and may further have elastomeric valves controlled through pressure applied to control channels (not shown) to deflect a membrane into a flow channel. Valves may be positioned along the dashed flow channels so as to contain sample and/or assay in their respective chambers (e.g., preventing backwards contamination after mixing). Valves may be positioned between pairs of sample an assay chambers to control mixing (e.g., by interface free diffusion). Detailed descriptions of suitable array architecture may be found in US patent publications US20100120038 and US20140193896, both of which are incorporated herein by reference in their entirety.

In certain aspects, assay inlets may provide primers to amplify splint ligation products formed as described herein.

Alternatively or in addition, assay inlets may provide sample barcode primers that bind sample barcode sequences (or their reverse complement) on ligation products from a specific sample in a pool of samples. Such sample barcodes may be incorporated by splint ligation probes, and samples may be pooled before being provided to the array through a sample inlet. For example, if 8 samples are pooled for each of 48 different sample inlets, and 8 different assay inlets each amplify ligation product from a different sample, then 48×8 (i.e., 386) different samples may be assayed in the array. As such, assay inlets may increase the number of targets and/or samples detected. As such, an array device may comprise at least 12, at least 24, at least 48, or at least 96 separate sample inlets. In addition, at least 4, at least 8, at least 12, or at least 24 different sample barcodes may be flowed through different assay inlets. As such, more samples may be assayed than there are sample inlets. For example, at least 386 different samples may be assayed in the array. The array footprint may be less than 100 square centimetres, such as less than 20 square centimetres, or less than 10 square centimetres. In certain aspects, different target specific primers are also flowed into different assay inlets, such that different reaction sites detect different targets from different samples.

Detection of Ligation Products

Detection of splint ligation products may be by sequencing (e.g., of sample barcode and pooled samples), or by PCR amplification (e.g., endpoint PCR or quantitative PCR). Methods of library preparation for sequencing are known, and may be performed on a microfluidic device as described herein. Alternatively, PCR products may be quantified to determine the amount of a sample (e.g., sample library) to add to a pool of samples. Quantification may be performed during PCR, such as in a quantitative PCR or "qPCR". In qPCR, abundance of double stranded DNA (dsDNA) is measured over multiple cycles using a dye indicator (such as an dsDNA intercalating dye) and the linear phase of amplification curve is used to calculate a starting amount of the target that was amplified. Other forms of quantitation may include end point detection (e.g., measuring amount of amplified target after a set number of runs, such as by a dye or a target specific probe) or digital PCR.

PCR of ligation product, in tube or on an array IFC, may therefore allow detection and optionally quantitation of the target nucleic acid. As described above, one or more probes may have a sample barcode, such that the ligation product has a sample barcode on one or both sides. PCR amplification may then be with one or more sample barcode specific primers, such as to selectively amplify ligation product from a specific sample in a pool of samples as described herein. Alternatively or in addition, at least some primers may be target specific to allow for detection of a ligation product from a specific target nucleic acid.

Splinted Ligation Kits

In certain aspects, a kit for parallel sample process may include reagent for splint ligation methods described herein. Such a kit may have two splint ligation probes described in any embodiments herein, and may optionally further comprise ligase for forming ligation products, primers for amplifying ligation products, and/or additional reagents. Splinted ligation kits may further include one or more microfluidic devices described herein.

Microfluidic Automation and Parallel Processing

A system for controlling fluid flow in the microfluidic device, thermal control, and/or imaging the microfluidic device is described in US patent publication number US20080088952, which is incorporated herein by reference in its entirety. For example, the system may perform one or more steps of:

i) flowing a plurality of samples into reaction chambers of the microfluidic device;

ii) amplifying template nucleic acids from the plurality of samples; and iii) detecting amplification reactions.

The system may include one or more of:

an automated pressure source for applying a pressure to actuate valves in an elastomeric microfluidic device and to introduce samples into a plurality of reaction chambers of the elastomeric microfluidic device, wherein the elastomeric microfluidic device includes a carrier accessible to the automated pressure source;

a thermal platen configured to mate with a portion of the carrier of the elastomeric microfluidic device; and an optical imaging system comprising a light source, an optical lens system, and a detector array camera.

For example, the automated pressure source, the thermal platen, and the optical imagining system are part of a single platform.

The system may isolate at least some of the plurality of the reaction chambers from one another. The microfluidic device may be any device described herein, and the system may perform any method described herein.

In certain aspects, an array microfluidic device (e.g., array IFC) may be used, such as for detection of splint ligation products (i.e., their targets) as described herein. In certain aspects, an array IFC may be integrated (in fluidic communication) with a unit cell comprising a column and/or processing sites as described herein.

FIG. 12 is a schematic of an array integrated fluidic circuit (IFC). As shown, a plurality of sample inlets 1202A-X provide sample to sample chambers (black boxes). A plurality of assay inlets 1204A-Y provide assay reagents (e.g., primers and optionally additional PCR components such as polymerase, dNTPs and/or cofactors) to assay chambers (white boxes). Sample inlets to the array may be directly from wells loaded from a user, or may be downstream of a column and/or sample preprocessing sites as described herein and shown in FIG. 3 or 4. In certain aspects, assay inlets may provide different target specific primers.

Integrated Workflows and Microfluidic Devices

As described above, an integrated microfluidic device may therefore include, an array of reaction sites and a plurality of sample processing unit cells comprising a plurality of sample processing sites, wherein the unit cell is in fluidic communication with a plurality of different reagent inlets, and wherein sample inlets to the array are downstream of the plurality of sample processing sites of the plurality of unit cells.

The plurality of reagent inlets may share a common channel to each unit cell. The microfluidic device may include a multiplexor configured to control which reagent inlet is used to load a processing site of the unit cell.

The plurality of sample processing sites may include a plurality of loops and/or chambers. Each unit cell further includes one or more of a sample inlet channel, a waste outlet channel, additional reagent inlets, and/or additional columns.

Figure 17:
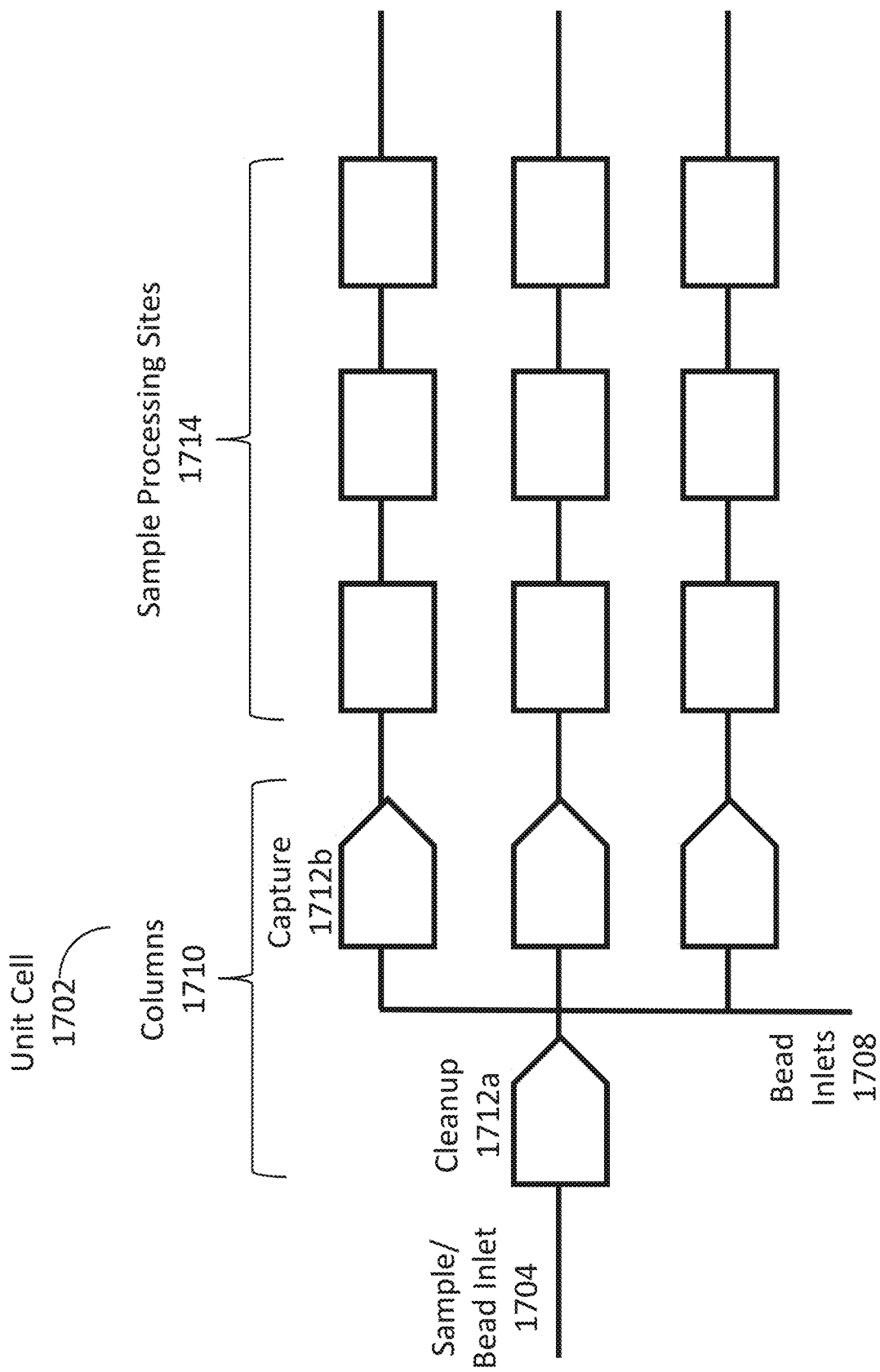
FIG. 17 is a schematic similar to that of FIG. 3 and showing an exemplary unit cell with a plurality of columns.

Each unit cells may include a plurality of valves configured to control the unit cell. The plurality of valves may be configured to deliver sample and reagents to different locations in the unit cell. The plurality of valves may be configured to place sample processing locations in isolation or in communication with one another. The plurality of valves may be configured to drive mixing at different locations. The plurality of valves are configured to direct flow of sample or reagents solution out of the unit cell For example, the unit cell includes a peristaltic pump (e.g., defined by a set of valves in series).

Wherein individual unit cells further includes at least one column configured to retain beads. The column may include a sieve architecture providing a plurality of openings through which fluid may flow but beads larger than the hole may be retained. In certain aspects, the unit cell includes at least two columns, such as columns arranged in series and/or in parallel. For example, the unit cell may include a first column (e.g., for cleanup, such as serum cleanup) fed by a sample/bead inlet channel, and may further include a plurality of columns in parallel (e.g., each fed by a bead inlet and communicating with a plurality of downstream sample processing sites), such as is shown in FIG. 17. A unit cell with multiple columns may be used for enrichment of different target biomolecules, as described further herein.

Individual reaction sites of the array of reaction sites may each include an assay chamber and a sample chamber. Sample inlet channels may provide sample to the sample chambers and assay inlets provide assay reagents to the assay chambers, for example as shown in FIG. 12.

The microfluidic device may include multiple layers such that sample inlet flow channels and assay inlet flow channels pass over one another. The microfluidic device is an elastomeric microfluidic device, for example, may include PDMS (polydimethylsiloxane). Elastomeric valves of the device may be defined by the intersection of a flow channel and a control channel which are separated by an elastomeric membrane that can be deflected into or retracted from the flow channel in response to an actuation force.

The microfluidic device includes at least 12 unit cells, at least 24 unit cells, at least 48 unit cells, or at least 96 unit cells. The an array of the microfluidic device may further include at least 3 times, at least 8 times, at least 16 times, or at least 24 times the number of reactions sites compared to unit cells. For example, each unit cell may feed into at least 3, at least 8 k at least 16, or at least 24 different reaction sites. The different reaction sites may each be fed by a different reagent inlet.

Wherein the unit cell includes a cell capture site (e.g., in place of a column) as described further herein.

In certain aspects, the array downstream of a unit cell may be a digital array, i.e., an array that provides serial dilution to allow quantitation of a single target by digital PCR.

In certain aspects, an integrated microfluidic device may include: an array of reaction sites; and a plurality of sample processing unit cells comprising a plurality of sample processing sites, wherein the unit cell is in fluidic communication with a plurality of different reagent inlets; wherein sample inlets to the array are downstream of the plurality of sample processing sites of the plurality of unit cells. Such a microfluidic device is depicted in FIG. 17 and may or may not include an array of reaction sites downstream of the unit cells.

FIG. 17 is a schematic similar to that of FIG. 3 and showing an exemplary unit cell with a plurality of columns 1710 for retaining beads, specifically a cleanup column 1710a for depleting undesired components of a sample, and a plurality of capture columns 1710b for capturing different target molecules. Beads and sample may be flowed into the cleanup column 1710a through a first inlet 1704. Different capture beads may be loaded into different capture columns 1710b through one or more bead inlets 1708.

In certain aspects, assay inlets may provide primers to amplify splint ligation products formed as described herein. Alternatively or in addition, assay inlets may provide sample barcode primers that bind sample barcode sequences (or their reverse complement) on ligation products from a specific sample in a pool of samples. Such sample barcodes may be incorporated by splint ligation probes, and samples may be pooled before being provided to the array through a sample inlet. For example, if 8 samples are pooled for each of 48 different sample inlets, and 8 different assay inlets each amplify ligation product from a different sample, then 48×8 (i.e., 386) different samples may be assayed in the array. As such, assay inlets may increase the number of targets and/or samples detected.

For example, a method may include loading beads into a column of a unit cell and capturing sample (i.e., biomolecules of a sample such as proteins, antibodies, RNA, viral particles, etc.) on the bead (e.g., before or after loading the beads into the column). As discussed herein, the bead may include (e.g., present on its surface) one or more of a protein (e.g., an antibody, such as an antibody to a target serum protein or viral antigen) and oligonucleotide (e.g., that hybridizes to target RNA, such as a viral RNA). Additional steps may include washing beads, such that a wash buffer flows over the beads in the column and into a waste outlet. Optionally a reporter, such as an oligonucleotide-conjugated antibody that binds to target biomolecules or an oligonucleotide probe that hybridizes to target biomolecules may be flowed over the beads. Additional steps may include eluting from the beads, such as by flowing an elution buffer over the beads in the column and optionally further cycling the elution buffer across the beads such as by passing the buffer around a loop using a peristaltic pump. Of note, mixing across sample processing sites in any step may be driven by a peristaltic pump. In certain aspects, elution may include degrading the attachment of a biomolecule to the bead, such as by a restriction enzyme, RNAse, or by a uracil DNA glycosylase (UDG) as described further herein. Eluted biomolecules may be mixed with a preamplification master mix (e.g., that provides for whole genome amplification, whole transcriptome amplification, or multiplexed targeted preamplification). Prior to, or in the same step as preamplification, a sample prep step such as reverse transcription, proximity assay (such as proximity extension or ligation), or preparation of genomic DNA. In certain aspects, one or more enzymes (e.g., proteases) may be inhibited or degraded prior to the preamplification or a later detection step. In certain aspects, preamplification is not performed. Processed sample may then be passed into an array of reactions sites of the same microfluidic device, for example, though a sample inlet from the unit cell into a plurality of sample chambers of different reaction sites as shown in FIG. 12. Different targets of a sample may be detected across different reaction sites, for example, by PCR (e.g., qPCR) of products produced during sample preparation.

The array IFC may have multiple layers such that sample and assay flow channels can pass over one another. The array IFC may be elastomeric (e.g., include an elastomer such as PDMS), and may further have elastomeric valves controlled through pressure applied to control channels (not shown) to deflect a membrane into a flow channel. Valves may be positioned along the dashed flow channels so as to contain sample and/or assay in their respective chambers (e.g., preventing backwards contamination after mixing). Valves may be positioned between pairs of sample an assay chambers to control mixing (e.g., by interface free diffusion). Detailed descriptions of suitable array architecture may be found in US patent publications US20100120038 and US20140193896, both of which are incorporated herein by reference in their entirety.

In certain aspects, such as for splinted ligation applications, a subject microfluidic workflow may include on or more of the following steps.
1. Load beads into the column of a unit cell from a shared inlet
2. Capture sample (e.g., from independent inlets)
3. Wash beads (e.g., from shared inlet)
4. Elute into a first chamber (e.g., from a shared inlet)
5. Load Preamp Mastermix into a second chamber (e.g., from shared inlet)
6. Load Amplicon from preamp into sample chambers
7. Load assay mix (PCR mix, primers, and/or probes) into assay chambers
8. Mix a fraction (i.e., at least a fraction of the contents of) of sample chamber with assay mix in assay chamber For example, a method of performing an assay on a microfluidic device may include each of:
loading beads into a column of a unit cell from a shared inlet;
capturing sample biomolecules of interest on the beads;
washing the beads;
eluting captured biomolecules into a first chamber;
loading preamp mastermix into a second chamber;
performing a preamplification reaction;
loading amplicon from preamplification reaction into sample chambers;
loading an assay mix into assay chambers; and
mixing at least a fraction of the contents of the sample chamber and assay chamber.

The microfluidic device may be an integrated microfluidic an microfluidic device as described above.

The step of capturing (capturing sample biomolecules on the beads) may be before or after the step of loading the beads onto the column. Washing the beads may include flowing a wash buffer solution over the beads in the column, or may include mixing the beads with a wash buffer solution and separating the beads from the solution (e.g., wherein the beads are magnetic beads) before loading the beads on the column. In certain aspects, beads that bind to different target biomolecules of a sample may be combined before loading into the column, allowing for multiplexed sample processing and optionally downstream detection of different targets in each sample in an array of the microfluidic device.

As such, the subject methods and microfluidic devices may enable targeted sample enrichment by: solid-phase bead-based capture of predefined nucleic acid sequences or other targets in columns of unit cells; integrated washing, elution, and preamp in sample processing sites of unit cells; and detection of specific targets (e.g. by qPCR) across a plurality of reaction sites for each sample.

Capture and/or Detection of Target Nucleotide Sequences

The assay mix may include at least one of PCR mix, primers, and a probe. The preamp master mix may include reverse transcriptase and a polymerase, such as when the target is an RNA such as a viral RNA. Reverse transcription and preamplification may be performed in the same step.

The preamp mastermix may include primer pairs to a plurality of different target nucleotide sequences. The presence of each target nucleotide sequence may be detected by PCR (such as by qPCR) after the step of mixing. The plurality of different target nucleotide sequences may be viral RNA sequences.

The method may further include detecting the presence of the biomolecules of interest after the step of mixing, such as by PCR (e.g., end point or qPCR).

Figure 15B:
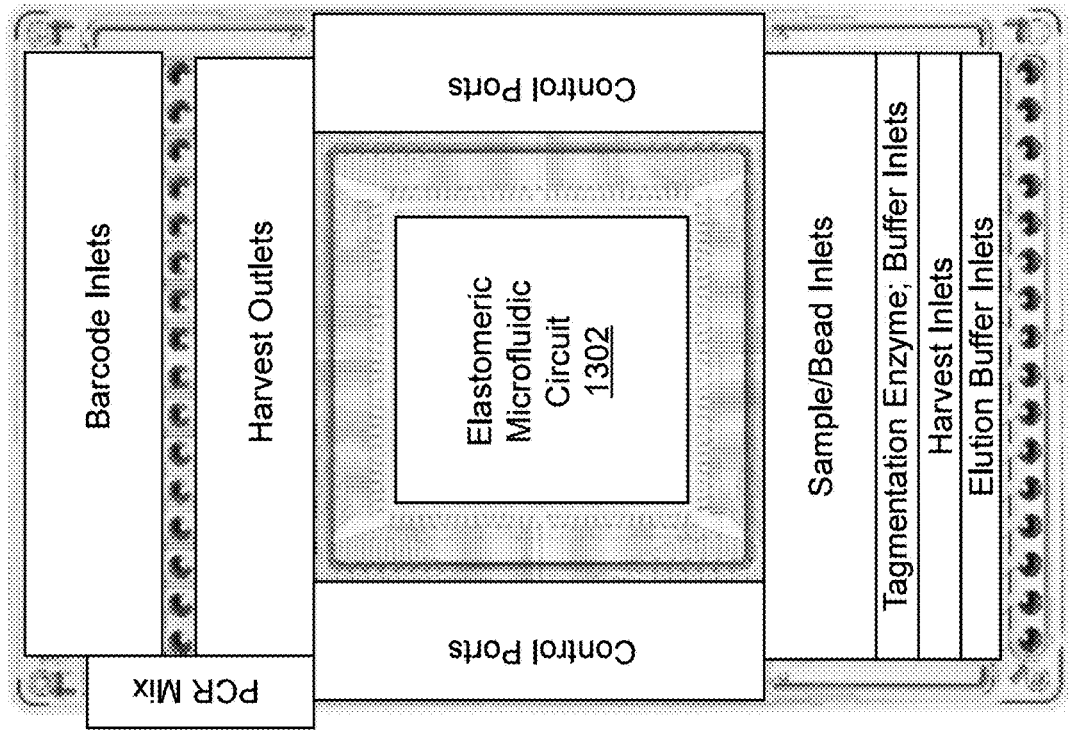
FIG. 15B is a schematic showing an exemplary loading scheme for DNA sequencing preparation.
Figure 15A:
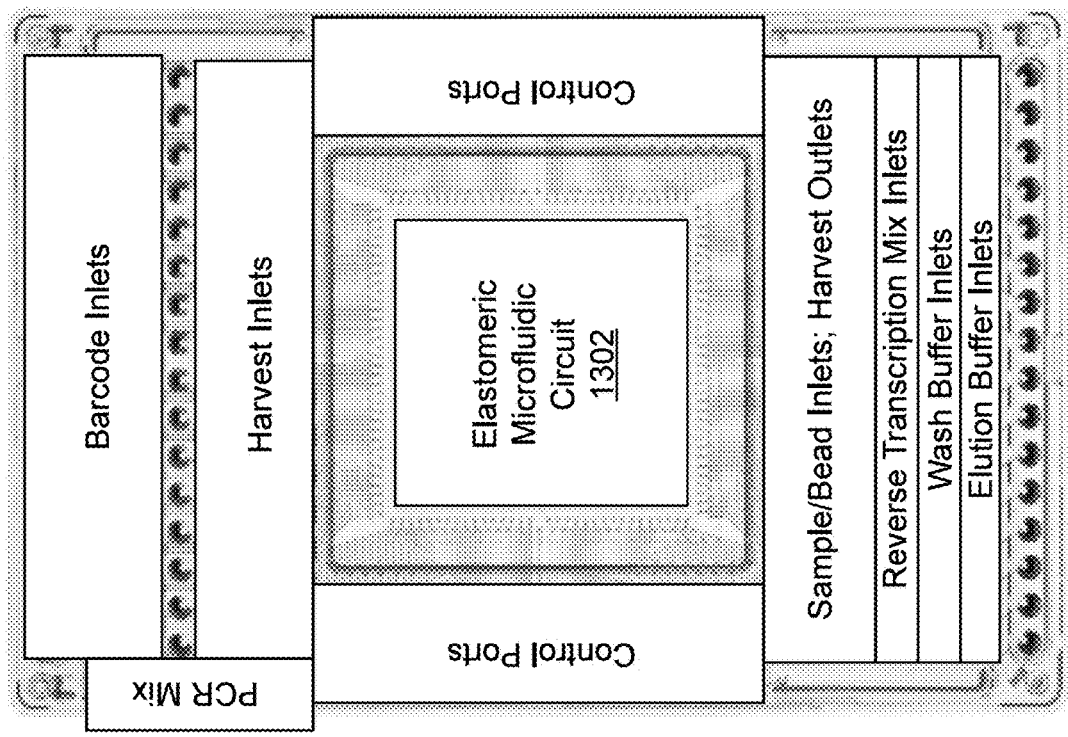
FIG. 15A is a schematic showing an exemplary loading scheme for RNA sequencing preparation.

Alternatively or in addition, detection may be by sequencing. For example, the method may further include amplifying after the step of mixing, and pooling the amplified product from different samples prior to sequencing. Preamplified sample may quantified by qPCR and normalized for pooling prior to the step of sequencing. The method may further include a bead cleanup step before and after preamplification, e.g., using the same or different column of the unit cell. The method may further comprising sample indexing after the step of mixing and before pooling. FIG. 15 is a schematic showing exemplary loading schemes for RNA sequencing preparation (A) and DNA sequencing preparation (B).

The beads may specifically bind target viral particles (e.g., viral antigen), viral RNA, mammalian mRNA, genomic DNA, protein (e.g., antibodies), or any other target biomolecule of interest. For example, herein the beads include and affinity reagent such as an antibody (e.g., presented on the surface of the bead) that binds to a viral antigen or mammalian protein, such as a prostate specific antigen or other cancer biomarker. Other suitable affinity reagents include an avidin or biotin, an aptamer, a tetramer such as an MHC or peptide-MHC, a receptor such as a TCR, and so forth. In certain aspects the beads may include a nucleic acid, such as an ssDNA that specifically binds a target nucleotide sequence as described further herein.

Figure 16B:
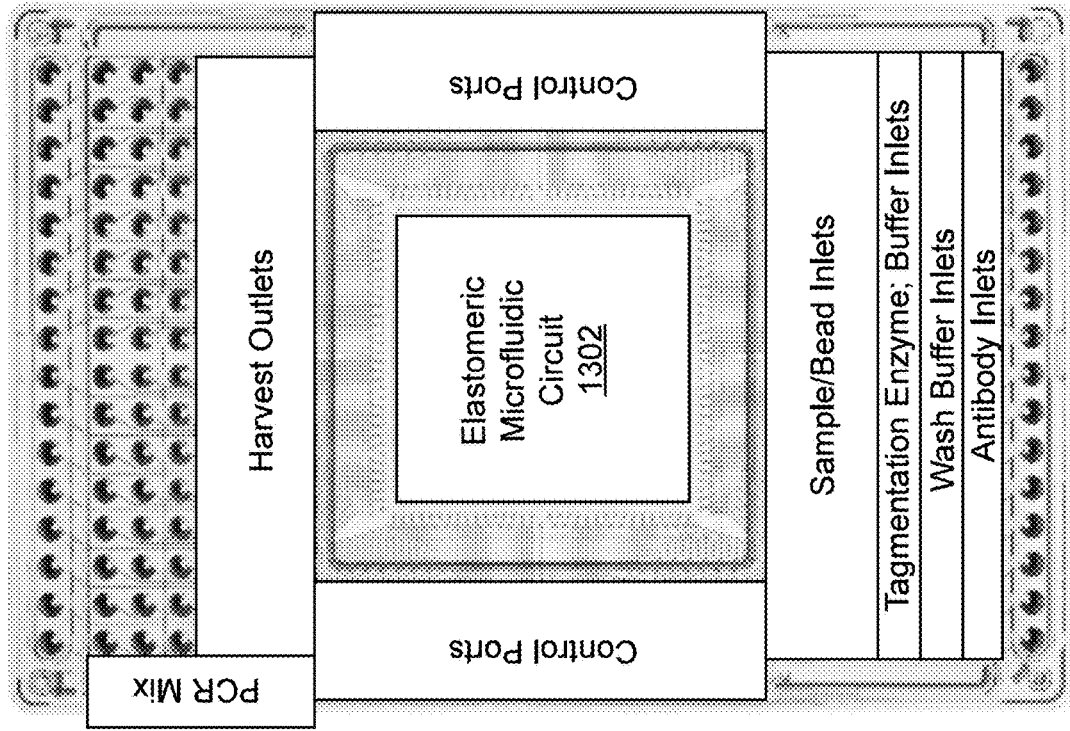
FIG. 16B is a schematic showing an exemplary loading scheme for sample preparation for detection of a protein (such as a cancer marker, viral antigen, or antibody to a viral antigen).
Figure 16A:
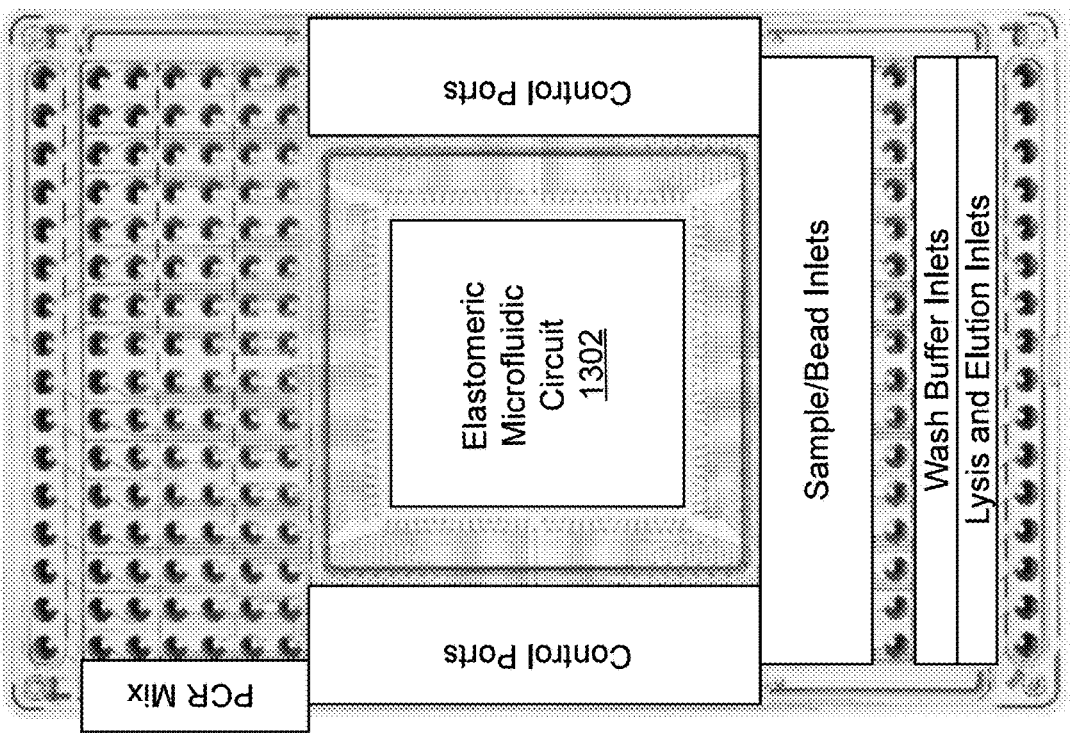
FIG. 16A is a schematic showing an exemplary loading scheme for oligonucleotide detection on chip (such as detection of a viral RNA).

FIG. 16A provides a schematic showing exemplary loading scheme for oligonucleotide detection on chip (such as for detection of a viral RNA). Of note, an array may be downstream of the sample processing unit cell such that one or more target viral RNA sequences can be detected by qPCR as described herein.

In certain aspects, the biomolecules of interest include one or more target nucleotide sequences. For example, the bead is functionalized with single stranded DNA sequences that specifically hybridize the one or more target nucleotide sequences. The one or more target nucleotide sequences may be a viral polynucleotide sequence, an RNA sequence, or a viral RNA sequence. For example, the viral RNA sequence may be an SARS-CoV-2 viral RNA sequence, e.g., wherein the one or more target nucleotide sequences include at least two of N1, N2, and N3 SARS-CoV-2 sequences, and the method may include detecting the at least two of N1, N2, and N3 SARS-CoV-2 sequences in separate reaction sites. Alternatively or in addition, the viral RNA sequence may be an influenza RNA sequence, e.g., wherein the one or more target nucleotide sequences include at least an H3N2 Influenza RNA sequence and an H1N1 Influenza RNA sequence in separate reaction sites, and the method may include detecting at least the H3N2 Influenza RNA sequence and the H1N1 Influenza RNA sequence in separate reaction sites. As discussed elsewhere herein, the reaction site includes a sample chamber and an assay chamber.

In certain aspects, a unit cell may include multiple columns each loaded with beads that capture a different biomolecule of interest (e.g., a different target protein or nucleotide sequence).

Figure 29:
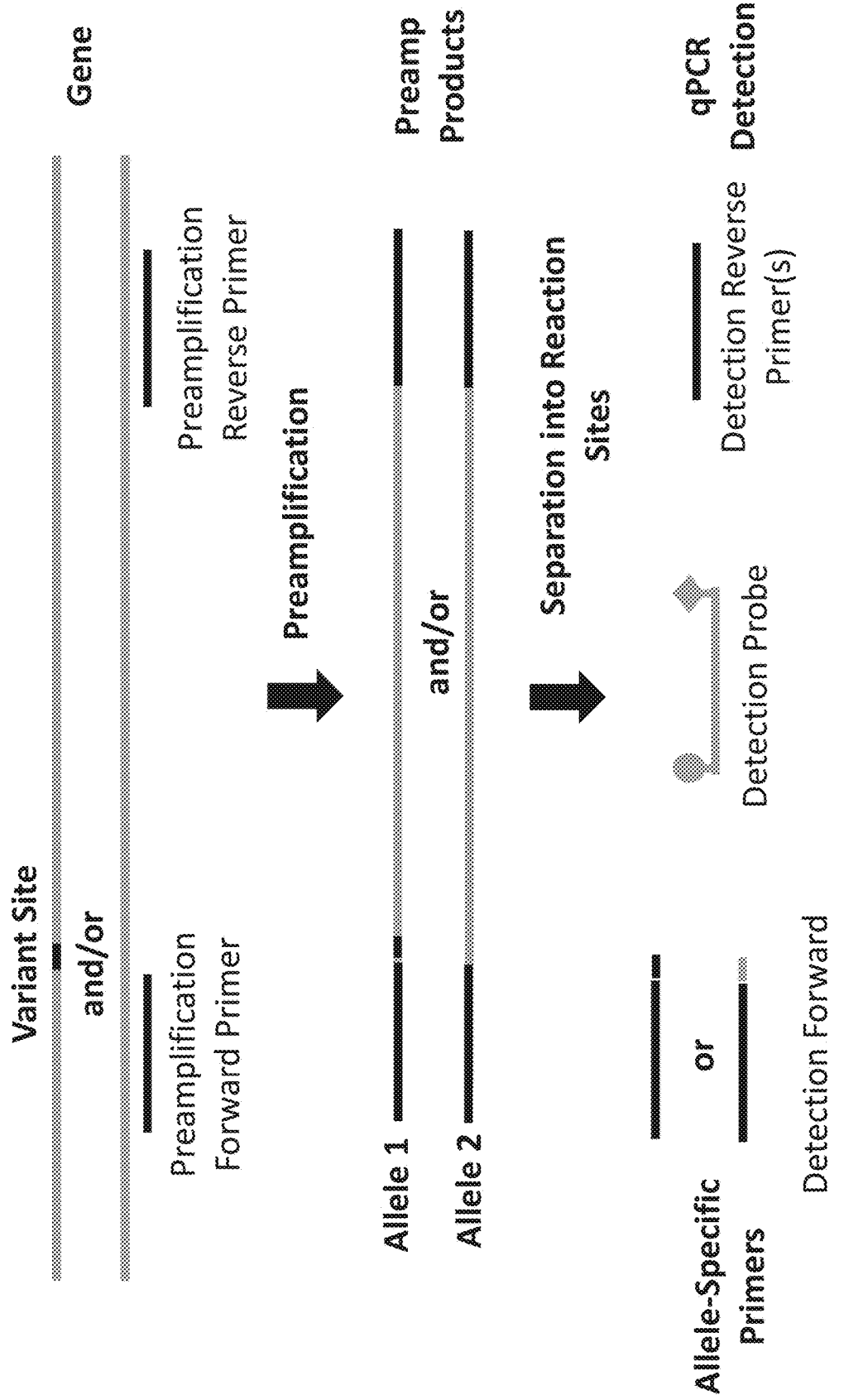
FIG. 29 shows a multi-step process for detecting specific alleles of a gene in a sample.

As discussed further herein, aspects include methods of detecting at least one allele of a gene; For example, preamplification may include amplification of at least a first allele and a second allele of a gene (i.e., if present in the sample), such as with the same preamplification primer pair (e.g., as shown in FIG. 29). In certain aspects, bead based capture of the gene and/or preamplification of at least a first and second allele may be performed on the unit cell of a microfluidic device as described herein. Preamplified sample may then be split into a plurality of reaction sites, and different alleles detected in different reaction sites. For example, a first assay mix loaded into a first set of assay chambers may include an allele-specific primer pair that specifically amplifies a first allele sequence, wherein a second assay mix loaded into a second set of assay chambers may include an allele-specific primer pair that specifically amplifies a second allele sequence.

An allele-specific primer pair has at least on primer (optionally two primers) of the pair (i.e., at least one allele-specific primer) that specifically hybridizes and extends along the target allele. For example, the 3' end of an allele-specific primer may be complementary to a single nucleotide polymorphism (SNP) that distinguishes the allele. Alternatively, a portion of the allele-specific primer (e.g., at the 3' end) may be complementary to an insertion sequence that distinguishes the allele, or may be lacking a deletion sequence that distinguishes the allele and instead be complementary to a sequence following the deletion sequence. As such, one or more allele-specific primers (e.g., of different allele-specific primer pairs) may be specific for a SNP, an insertion or a deletion variant site. An insertion or deletion sequence may be a single nucleotide in length, or more than 2, more than 5, or more than 10 nucleotides in length. In certain aspects, at least one allele is a "wildtype" allele and another allele is a "mutant" allele that has a SNP or indel (insertion or deletion) mutation compared to the wildtype allele.

Figure 30:
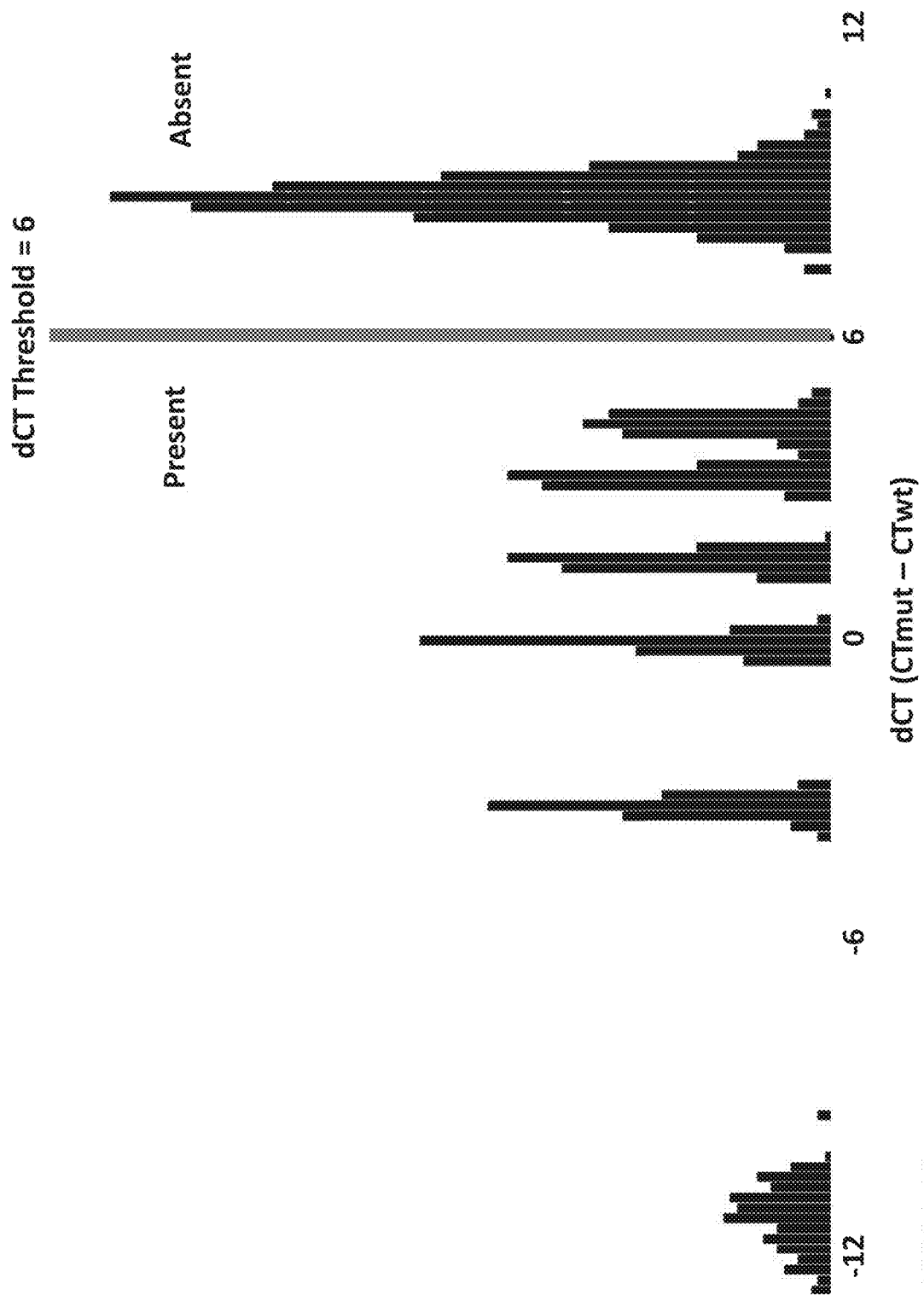
FIG. 30 shows exemplary use of a dCT threshold to identify presence of an allele.

The method may further include detection of the first and second allele sequence in the same sample by qPCR detection of the first and second allele sequences in separate reaction volumes, such as by identifying the presence of the first or second allele sequence in a sample by comparing a CT value of a qPCR of the first variant sequence to a CT value of a qPCR of the second variant sequence (e.g., as shown in FIG. 30).

Aspects include identifying the presence of at least 4 different alleles by the subject methods. At least 4 different alleles may be preamplified, such as by the same preamplification primer pair. One of the at least 4 different alleles may include a SNP variant site compared to a "wildtype" allele of the at least 4 different alleles, and optionally further, another of the at least 4 alleles may include an indel variant site compared to the "wildtype" allele of the at least 4 different alleles. A wildtype allele may be identified based on its prevalence (or historic prevalence in a population), or based on its role in the subject methods and kits (i.e., the CT of other alleles ("mutants") are compared to the CT of the wildtype allele to identify the presence of the mutant alleles). In certain aspects, a plurality of samples (e.g., at least 12, at least 24, at least 48, or at least 96 samples) are processed in parallel on the same microfluidic device, and the presence of the at least 4 different alleles is identified for each sample.

In certain aspects, the alleles are of a viral gene, such as SARS-CoV-2 spike S1 sequence.

Capture and/or Detection of Sample Proteins

Sample proteins, such as cancer markers or antibodies to a pathogen, may be captured, processed, and/or detected as described further herein.

FIG. 16B provides a schematic showing exemplary loading scheme for sample preparation for detection of a protein (such as a cancer marker, viral antigen, or antibody to a viral antigen). Of note, an array may be downstream of the sample processing unit cell such that one or more target proteins can be detected by (e.g., by immune-qPCR as described herein, in which case harvest solution may not be needed). In cases where sequencing is not the method of detection, tagmentation buffer may not be needed.

In certain aspects where the beads include an antibody that binds to a viral particle, The method may further include detecting viral RNA as described further herein, or the method may further include detecting the viral particle (e.g., by an immuno-PCR as described further herein). For example, oligonucleotide conjugated antibody may be bound to the viral particle, and the oligonucleotide amplified by PCR (e.g., detected by qPCR).

Microfluidic detection of rare species can often require expensive, contamination-prone sample preparation in order to provide competitive assay sensitivity compared to similar tube- or microwell plate-based assays. As an alternative to these sample preparation steps, solid-phase sample enrichment integrated within the microfluidic device has proven sufficient for some workflows (e.g. for mRNA and bacterial genome sequencing). Using similar methods, solid phase capture can be used to enrich for the presence of viral particles. As described herein, viral particles can be captured using beads (the solid phase) that have been conjugated with biomolecules, which specifically target corresponding biomolecules of the viral particles of interest. For example, antigen-antibody or receptor-ligand interactions. The beads can then be used to concentrate the population of viral content into a very small volume that can be used for nano- to microliter scale automated detection by qPCR all within a single device that completes the sample-to-answer (e.g., in less than 3 hours).

In certain aspects where the beads include a viral antigen (e.g., whole virus or portion thereof, such as SARS-CoV-2 spike S1 and/or S2), the presence sample antibodies that bind to the viral antigen may be detected. For example, antibodies from serum, plasma, whole blood, saliva, or a nasal swab may be passed over such beads in a column. An oligonucleotide conjugated antibody may then be bound to the sample antibodies, and the oligonucleotide may then be detected (e.g., by qPCR such as in an immuno-PCR workflow, or by sequencing). In certain aspects, the method may include detecting different antibody types, such as IgG and IgM (e.g., by immuno-PCR of a secondary antibodies that specifically bind an antibody type). In certain aspects, separate columns of a unit cell each include beads presenting a different viral antigen, e.g., wherein each different viral antigen is from a different strain (e.g., a different mutation of the SARS-CoV-2 spike S1 and/or S2 protein domains). The method may further include using a first column for cleanup, such as a serum based cleanup to produce a purified serum sample (as described further herein). The method may further include splitting the purified sample between separate columns that each include beads presenting a different viral antigen. Such different antibody types and/or antibodies to different viral antigen may be detected in the unit cell (e.g., using different color probes) or may be detected in different reaction sites downstream of the unit cell. Detection may be by PCR, such as qPCR, using primers specific for oligonucleotide conjugated to a specific secondary antibody.

Beads may be loaded into the column of a unit cell from an inlet shared with the sample (e.g., beads can be loaded before sample, or they can be loaded in admixture such as with sample biomolecules already captured on the beads). The sample biomolecules of interest may include proteins. The biomolecules of interest may be captured by flowing sample over the beads loaded into the column, or the biomolecules of interest may be captured by mixing the beads with a sample before loading the beads into the column. The sample proteins may be captured on the beads by antibodies bound to the beads. The method may further include binding antibodies to the sample proteins captured on the beads, wherein the antibodies are conjugated to oligonucleotides. In certain aspects, sample may be blood (e.g., serum, plasma, or whole blood), saliva or a nasal swab. When the sample is serum, the method may further include a serum cleanup step in a first column of the unit cell. If the sample proteins are antibodies, the beads may present an antigen such as a viral antigen. For example, the viral antigen may be a SARS-CoV-2 antigen such as a SARS-CoV-2 spike S1 and/or S2 protein domain or peptide thereof. In another example, the viral antigen is an influenza antigen. In certain aspects a unit cell includes a plurality of columns that are each loaded with beads presenting a different viral antigen. For example, the different viral antigens include variants of the same virus, such as different SARS-CoV-2 spike S1 and/or S2 domain mutants or peptides thereof. The method may further include detecting the antibodies by immuno-PCR. The method may include separately detecting at least IgG and IgM antibodies specific for a viral antigen.

The method may include detecting the presence of the proteins in a plurality of reaction sites of the microfluidic device, such as by immuno-PCR or a proximity assay. For example, the method may include hybridizing an ssDNA complement to the oligonucleotide of an oligonucleotide conjugated antibody, and may further include cleaving (degrading) the oligonucleotide. For example, the oligonucleotides conjugated to the antibodies include uracil, and wherein degrading is with Uracil DNA-glycosylase (UDG).

In certain aspects a plurality of different proteins are detected for each of a plurality of different samples. A step of detecting may include PCR, such as qPCR, in the unit cell, or in an array of reaction sites downstream of the unit cell. In certain aspects, the sample proteins are cancer biomarkers such as prostate specific antigens (e.g., PSA, free PSA p2PSA, and/or other isoforms of PSA) and the beads include antibodies to the cancer biomarkers. In other aspects, the sample proteins are antibodies (e.g., to a viral antigen) and the beads include the antigen specifically bound by the antibodies.

Methods may further include performing a bead based cleanup, such as a serum cleanup to produce a purified serum sample off the microfluidic device. As such, the unit cell includes at least two columns, wherein one of the at least two columns is used for the cleanup prior to further sample processing. In certain aspects, a serum based cleanup depletes at least one of IgG and albumin by binding to beads. For example, beads with antibody specific for human serum albumin and/or protein G for capturing IgG, such as PureProteome beads, may be used.

In certain aspects, separate columns of a unit cell are used to enrich for a separate biomolecule of interest from the same sample. For example, a first column may be used for cleanup (e.g., serum based cleanup to produce a purified serum sample), and a method may further include splitting the purified sample between separate columns that each enrich a different biomolecule of interest, which may then be detected through PCR (e.g., qPCR) in sample processing sites or reaction sites downstream of the column. Alternatively, processed sample may be harvested and run on a separate microfluidic device comprising an array of reaction sites. The workflow may be performed for immuno-PCR, proximity assays, or reverse transcribed RNA targets.

A serological method of the subject application may include detecting antibodies to a pathogen, such as a to a virus. In one example, the antibodies may be to SARS-CoV2, such as an S1 or S2 domain of the SARS-CoV-2 spike protein. As such, a sample for the subject methods may be prepared by:
Block 100-200K SARS-CoV2 antigen-beads per sample with Blocking buffer (1% BSA, PBS)
Incubate for 1 h at RT with agitation (1500 rpm).
Wash with Washing Solution (1×PBS, 0.1% BSA, 0.01% Tween 20)
Use a tube/plate magnetic separator or by centrifugation to separate the beads from the solutions
Dilute each bead pellet to reach a concentration of 2-4× $10^6$ Bead/mL
Aliquot the beads in each tube or well
Incubate with Target Antibody (for spiked-in samples) OR with TEST SAMPLE
Add Target Antibody dilutions (anti-RBD from Bethyl or anti-Spike S1 from Sino) OR the TEST SAMPLES
Incubate 2 hours at RT ©1500 rpm
Wash with Washing Solution, separate the beads from the solution with Tube/Plate Magnetic Separator or by centrifugation
Beads may then be loaded and sample process in a microfluidic device as described herein As described elsewhere herein, FIG. 17 is a schematic similar to that of FIG. 3 and showing an exemplary unit cell with a plurality of columns 1710 for retaining beads, specifically a cleanup column 1710a for depleting undesired components of a sample, and a plurality of capture columns 1710b for capturing different target molecules. Beads and sample may be flowed into the cleanup column 1710a through a first inlet 1704. Different capture beads may be loaded into different capture columns 1710b through one or more bead inlets 1708.

Figure 18:
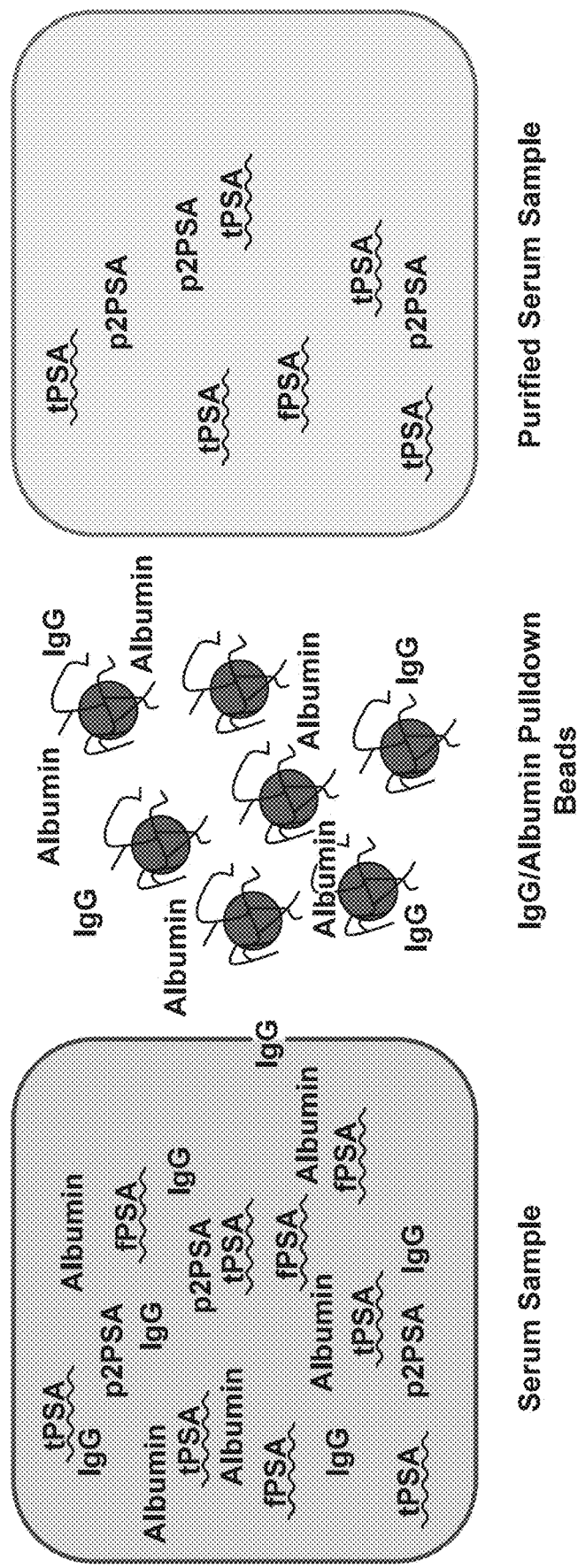
FIG. 18 shows an exemplary cleanup step.

FIG. 18 shows an exemplary cleanup step which may be performed in the cleanup column 1710a of FIG. 17. Specifically, FIG. 18 shows depletion of IgG and Albumin from serum.

Figure 19:
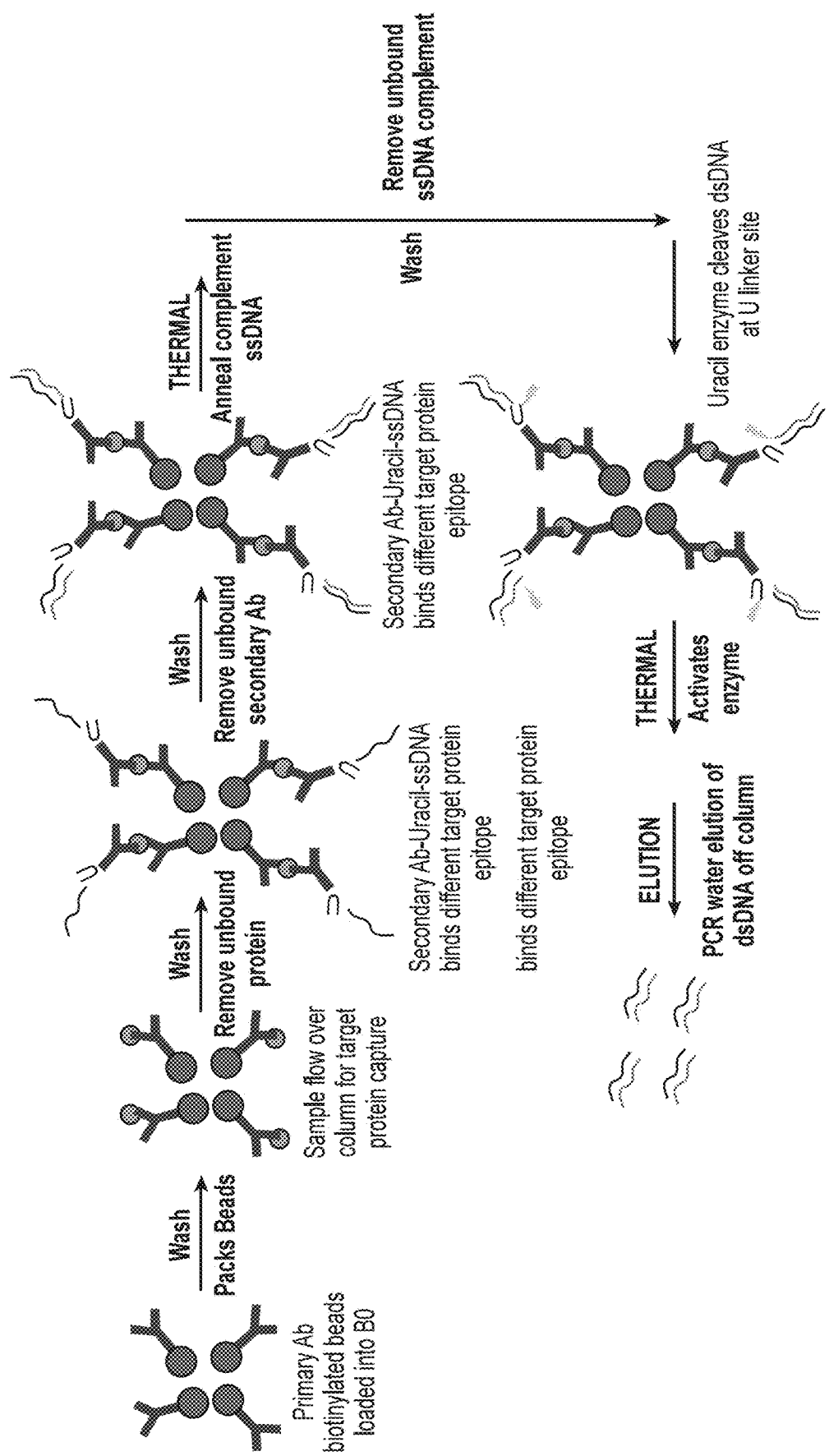
FIG. 19 shows an exemplary capture, sample preparation and PCR amplification.

FIG. 19 shows an exemplary capture, sample preparation and PCR amplification performed in one of the capture columns 1710b and series of processing sites 1714 of FIG. 17. Specifically, FIG. 19 shows capture of a target sample protein by beads presenting an antibody to the target protein, washing of the beads, binding and washing of an oligonucleotide conjugated antibody to the protein captured by the beads. FIG. 19 further shows annealing of a complementary oligonucleotide, elution of the oligonucleotides (through cleavage by UDG of one or more uracils of the oligonucleotide conjugated to the antibody). PCR of the eluted oligonucleotides can allow for direct detection such as by qPCR as described herein, or amplified product can be sequenced (e.g., sample indexed in the microfluidic device, pooled and sequenced). In general, immuno-PCR or a proximity assay may be used to detect target sample proteins.

A biomarker detection method of the subject application may, for example, include automated detection of specific biomarkers such as PSAs (prostate specific antigens, e.g., total PSA, free PSA and pro-2-PSA). These biomarkers are used in an FDA approved index, the Prostate Health Index (PHI) formula, to measure the risk of/potentially identify prostate cancer from serum samples. immunoqPCR can be adapted to provide quantitative output for these specific biomarkers in the microfluidic workflows described herein, using antibodies that specifically detect each of these target biomarkers, coupled with antibody-DNA tags; DNA tags can be separated out and quantified using PCR. For example, such a workflow may use the microfluidic device shown in FIG. 3 or FIG. 17, optionally integrated with the array such as that shown in FIG. 12. A such, a serum sample input may be followed by on-chip serum clean up, target capture and PCR. On-chip serum clean up may reduce the need for sample handling prior to loading the IFC, as sample clean up is carried out in an automated manner, on-chip. The cleaned serum sample may be split to detect the presence of the 3 PSA biomarkers. One sample input per unit, on the IFC, provides 3 different PSA outputs for each specific PSA PHI biomarker, in an automated manner. A set of PCR dilution outputs can be detected for each of these 3 different PSA outputs, individually and quantitatively, to be used in the PHI calculation (e.g., the calculation may be presented to a user by software running the microfluidic workflow and collecting the PCR dilution outputs).

As described further herein, an antibody sandwich assay type format may include a target capture antibody (e.g., on beads of the subject application) and a universal secondary antibody (e.g., that binds the PSA). In immune-PCR, antibody may be conjugated to either a single or double stranded DNA, and PCR can be performed whilst the DNA is still attached to the antibody or after it is cleaved off. For example, target capture antibody may be biotinylated and bound to a streptavidin bead, sample is flowed over the bead and PSA biomarker(s) are bound to the bead, secondary antibody tagged with a single strand oligonucleotide sequence is bound to the PSA biomarker(s), a complement to the single strand oligonucleotide sequence is bound to the tag on the secondary antibody to produce a double stranded DNA tag, the double strand DNA tag is separated from the antibody, and a PCR (e.g., qPCR) on the double stranded DNA is performed.

As such, a subject method may include one or more of a modified immunoqPCR for detection and quantitation, conjugated Bead-Ab capture of PHI target protein panel, a single microfluidic device for an integrated workflow, a multiplexed bead capture setup, a medium throughput with each sample input produces an automated multi-biomarker panel output, and/or serial stages of bead capture on the microfluidic device. While the above example is for PSA biomarkers, is would be understood than any suitable biomarkers may be analyzed by this method.

Bead Based Purification

One or more rounds of bead cleanup (bead based purification of sample biomolecules) may be performed in any of the methods described herein. Bead based purification (or "cleanup") generally refers to the enrichment or removal of a class of biomolecules, such a common protein (e.g., IgG, albumin, etc.) or an oligonucleotide (e.g. RNA and/or DNA). Aspects include at least two rounds of bead-based purification (e.g., of oligonucleotides). For example, a subject method may include performing a round of bead-based purification of oligonucleotides (e.g., sample oligonucleotides) before an amplification reaction, and another round of bead-based purification (e.g., of amplified product) after the amplification reaction. The amplification reaction may be any reaction described herein, for example, may be a preamplification reaction for sequencing preparation.

A round of bead-based purification may include capturing polynucleotides on beads, washing of the beads with a capture buffer, washing the beads with an alcohol, and allowing the alcohol to evaporate through one or more PDMS layers of the elastomeric device. In certain aspects, the alcohol is ethanol. In certain aspects, the beads extract RNA, DNA or both.

Figure 13:
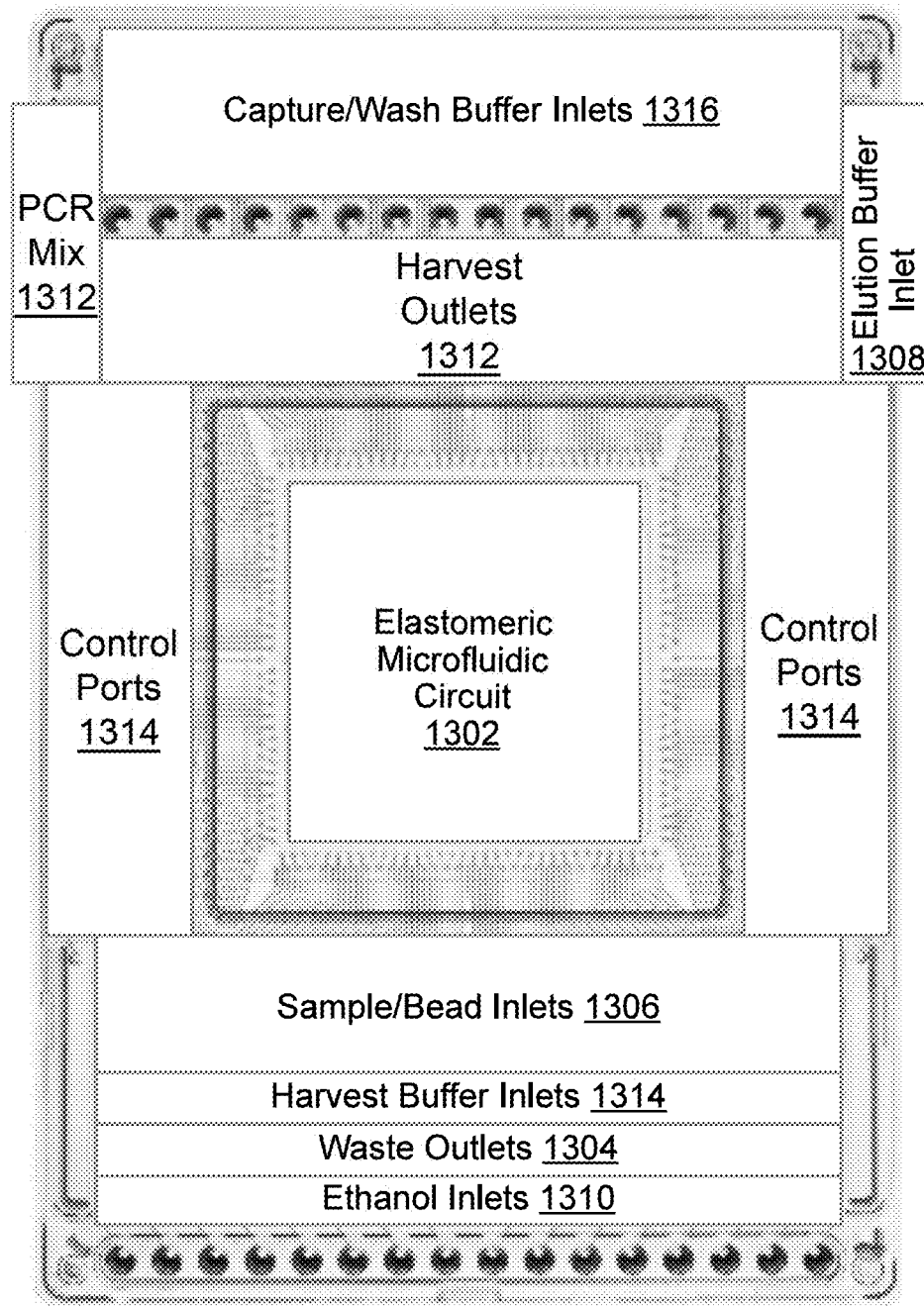
FIG. 13 is an image of an exemplary elastomeric microfluidic device and exemplary loading scheme of the subject application.

FIG. 13 is an image of an exemplary elastomeric microfluidic device and exemplary loading scheme of the subject application, similar in some respects to that of FIG. 2, but overlaid with markings showing waste outlets 1304, sample and bead inlets 1306, elution buffer inlets 1308, ethanol inlets 1310, PCR mix inlet 1312, harvest outlets 1312, harvest buffer inlets 1314, and capture buffer (also used as wash buffer) inlets 1316. Such a loading scheme may be used for bead cleanup, such as for multiple rounds of bead cleanup (such as before and after an amplification reaction).

Figure 14:
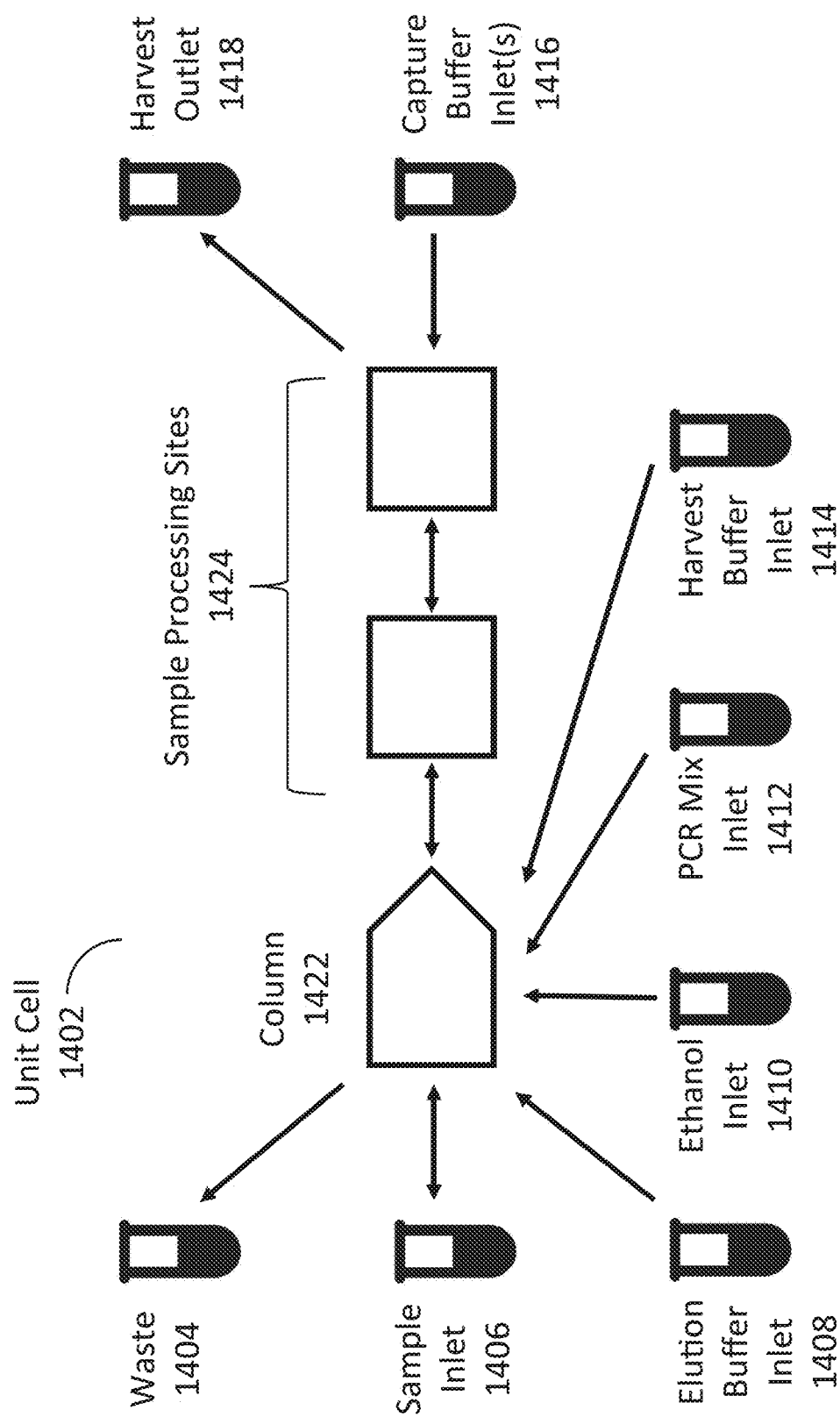
FIG. 14 is schematic similar to that of FIG. 3 and showing directions of flow from inlets, outlets and within the unit cell such as in a loading scheme of FIG. 13.

FIG. 14 is schematic similar to that of FIG. 3 and showing directions of flow from inlets, outlets and within the unit cell such as in a loading scheme of FIG. 13. Individual steps are described further herein.

A bead cleanup method may include on or more of the following steps:
1. Capture beads that have been pre-loaded with sample (e.g., by flowing sample through the column and flowing unbound sample to a waste outlet).
2. Wash beads with capture buffer.
3. Wash beads with ethanol.
4. Dry beads (e.g., under heat).
5. Elute into a processing site (e.g., by flowing elution buffer from an inlet through the capture site and into a first sample processing site).
6. Optionally resuspend sample and beads into sample inlet using capture buffer and repeat steps 1 through 5 in another round of cleanup.
7. Add amplification mix into a second sample processing site, and mix with the sample in the first sample processing site.
8. Amplify the sample (e.g., PCR amplification).
9. Resuspend sample and beads into sample inlet using capture buffer.
10. Repeat steps 1 through 5 in a post-amplification bead cleanup.
11. Optionally resuspend sample and beads into sample inlet using capture buffer and repeat steps 1 through 5 in another round of cleanup.
12. Flow harvest buffer through the column (e.g., through the entire unit cell) and into a harvest outlet.

The harvested amplified sample may be at a purity sufficient for library preparation and sequencing. In certain aspects, the amplification step includes sample indexing and/or qPCR for normalization prior to pooling harvested samples.

Cell Capture, Processing and Detection

In certain aspects, an array IFC may be integrated with a unit cell comprising a plurality of sample processing sites (e.g., chambers and/or loops), wherein the unit cell further includes a cell capture site (e.g., in place of a column in any such embodiments described herein). The cell capture site may include one or more bypass channels. For example, the unit cell may include architecture and be used as described in US patent publication 20130296196, which is incorporated herein by reference. Some single cell processing may include specific target amplification, whole genome amplification, whole transcriptome amplification, real-time PCR preparation, copy number variation, preamplification, and/or mRNA sequencing preparation. In certain aspects, a single cell may be captured (isolated), lysed, and then protein and/or RNA of the cell may be detected, for example as described in US patent publication number US20150132743, which is incorporated herein by reference. In the context of the subject application, a cell captured in a unit cell comprising a cell capture site may then be lysed, and optionally subjected to one or more additional reactions such as reverse transcription, proximity assay for detecting protein targets (e.g., proximity extension or ligations), and/or preamplification (e.g., whole genome amplification, targeted multiplexed preamplification of gDNA, cDNA or proximity extension products, etc.) prior to flowing the processed sample into an array of reaction sites of the same microfluidic device, where different RNA, DNA and/or protein targets may each be detected in separate reaction sites.

The cell capture site may selectively capture cells based on size. For example, cells 5 microns or less in diameter are captured with less than 5% (e.g., less than 1%) of the efficiency that cells larger than 10 microns are captured. The cell capture site may selectively capture cells based on affinity binding, such as binding of an antibody immobilized in the capture site to a cell expressing the corresponding antigen on its surface (e.g., so as to enrich for a particular cell type, such as an immune cell type such as T-cells or B-cells or subsets thereof). Individual unit cells may be in fluidic communication with sample inlet channels of the array architecture comprising a plurality of reaction sites, such as is shown in FIG. 12. In certain aspects, the captured cell may be lysed in a first step. Cell lysis may be followed by any of the reactions described herein in the context of a unit cell and/or an array of reaction sites. For example, after lysis, RNA from the cell may be reverse transcribed and preamplified, or genomic DNA may be processed and preamplified. Preamplification may be may be targeted, such as through a multiplexed reaction with at least 4 different primer pairs that each amplify a different target nucleotide sequences. The processed cell lysate (e.g., preamplified cell lysate) may be flowed into a sample inlet of an array of reaction sites, and a different target nucleotide sequence may be detected in different reaction sites using different primer pairs and/or different target specific probes.

For example, a single cell workflow may include flowing the plurality of cells through the microfluidic device such that individual cells from the plurality of cells are capture at individual capture sites in different unit cells of the microfluidic device; lysing the plurality of captured individual cells at the individual capture sites of the microfluidic device; performing reverse transcription, within the microfluidic device, on the plurality of individual lysed cells to produce reverse transcription products associated with each respective individual cell; optionally performing a multiplexed preamplification of cDNA produced by reverse transcriptions; splitting the contents of a unit cell across multiple reactions sites in an array of the microfluidic device; performing PCR, such as qPCR, within the microfluidic device to detect different targets (e.g., different reverse transcription products) in different reaction sites.

Alternatively or in addition, a single cell workflow may include flowing the plurality of cells through the microfluidic device such that individual cells from the plurality of cells are capture at individual capture sites in different unit cells of the microfluidic device; lysing the plurality of captured individual cells at the individual capture sites of the microfluidic device; incubating the cell lysate with two or more proximity extension probes in a binding reaction at an incubation temperature from about 15° C. to about 50° C. for a length of time from about 5 minutes to about 6 hours under conditions where the proximity extension probes bind to the target analyte, if present, in the cell lysate; incubating the binding reaction with an extension mix that includes a polymerase, wherein hybridized oligonucleotide components of the proximity extension probe are extended by the polymerase to produce extension products; splitting the contents of a unit cell across multiple reactions sites in an array of the microfluidic device; performing PCR, such as qPCR, within the microfluidic device to detect different targets (e.g., different proximity extension products) in different reaction sites.

Kits for an Integrated Workflow

The subject application also includes kits for performing any of the above methods. For example, a kit may include a microfluidic device of any one of embodiments and/or may include one or more reagents for performing the methods of any one of the above methods. Such reagents may be selected from one or more of an RNAse inhibitor, reverse transcriptase, polymerase, a preamplification mix (e.g., comprising a plurality of primer pairs that specifically amplify different target nucleotide sequences), beads that specifically capture sample biomolecules of interest as described herein, primers, probes, oligonucleotide-conjugated antibodies, enzymes of cleaving oligonucleotide from the antibodies they are conjugated to, or any other suitable reagent for performing the methods of the subject application.

Sample Barcoding Methods

Sample barcoding (i.e., sample tagging, or encoding) may increase sample throughput but the leftover primers (e.g., from sample with little or no target) may create crosstalk, leading to a false positive and/or higher background. Discussed herein are methods and kits for reducing such crosstalk.

Figure 20:
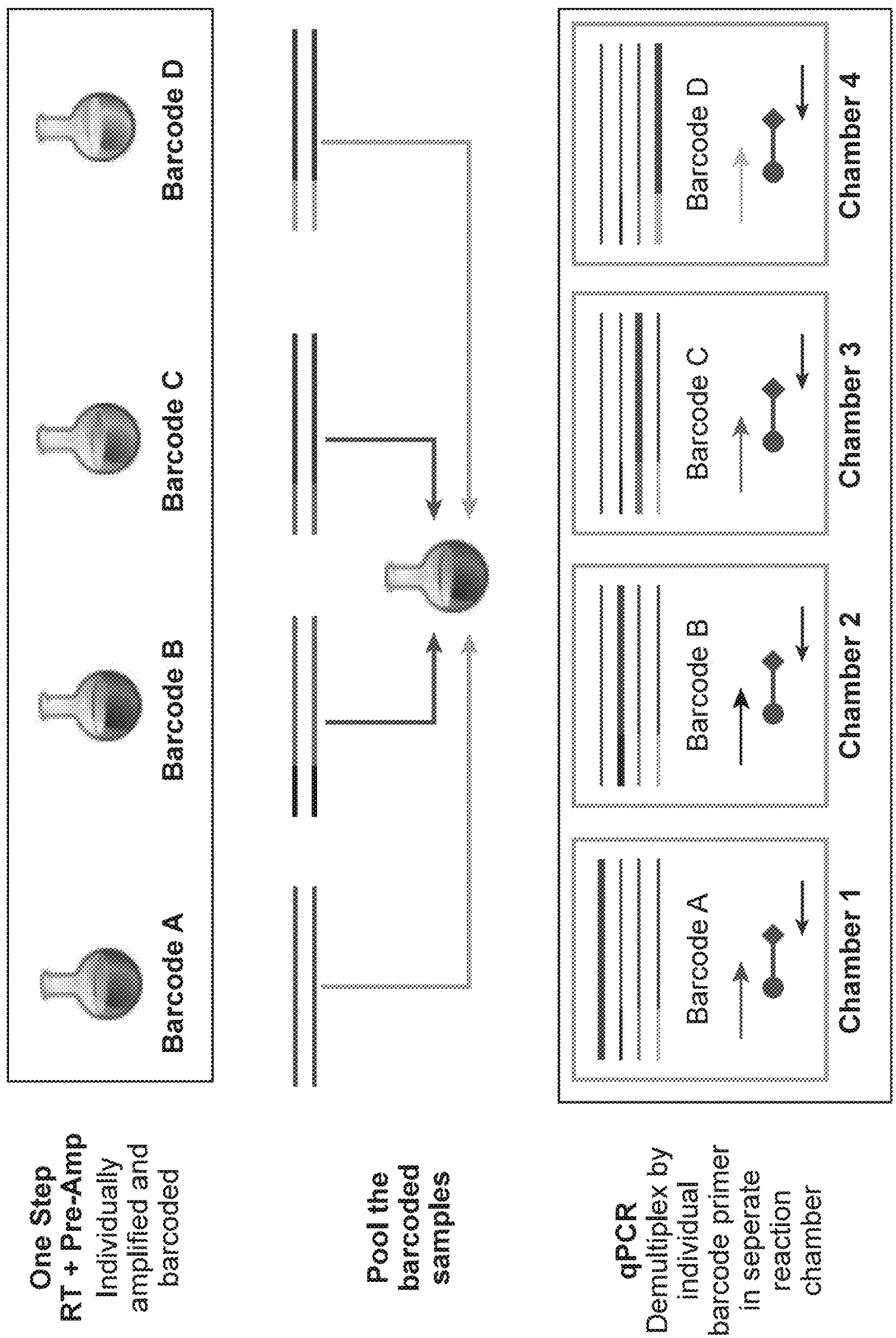
FIG. 20 shows a multiplex sample barcoding workflow of the subject application.

FIG. 20 shows a multiplex sample barcoding workflow of the subject application. Specifically, target nucleotide sequences from different samples can be reverse transcribed (if RNA) and preamplified in a reaction that incorporates a sample tag (i.e., sample barcode sequence). Preamplified mixture from different samples can be pooled and loaded onto a single inlet of a microfluidic device, then split into different chambers (different reaction sites) where target nucleotide sequences with different sample tags are selectively amplified. Such a workflow increased the number of samples that can be loaded onto a microfluidic device for a given number of sample inlets. The specific detection of each sample tagged target nucleotide sequence prevents the need to retest all samples individually if at least one is positive for a target nucleotide sequence. Each reaction site has the mixture of preamplified samples, a target specific probe (e.g., that fluoresces upon binding to the target), a sample barcode primer that selectively amplifies the reaction product of a specific sample, and a reverse primer (e.g., that is target specific, or that is specific for a target barcode incorporated during the preamplification reaction, such if when multiple targets are detected for a sample).

Figure 21:
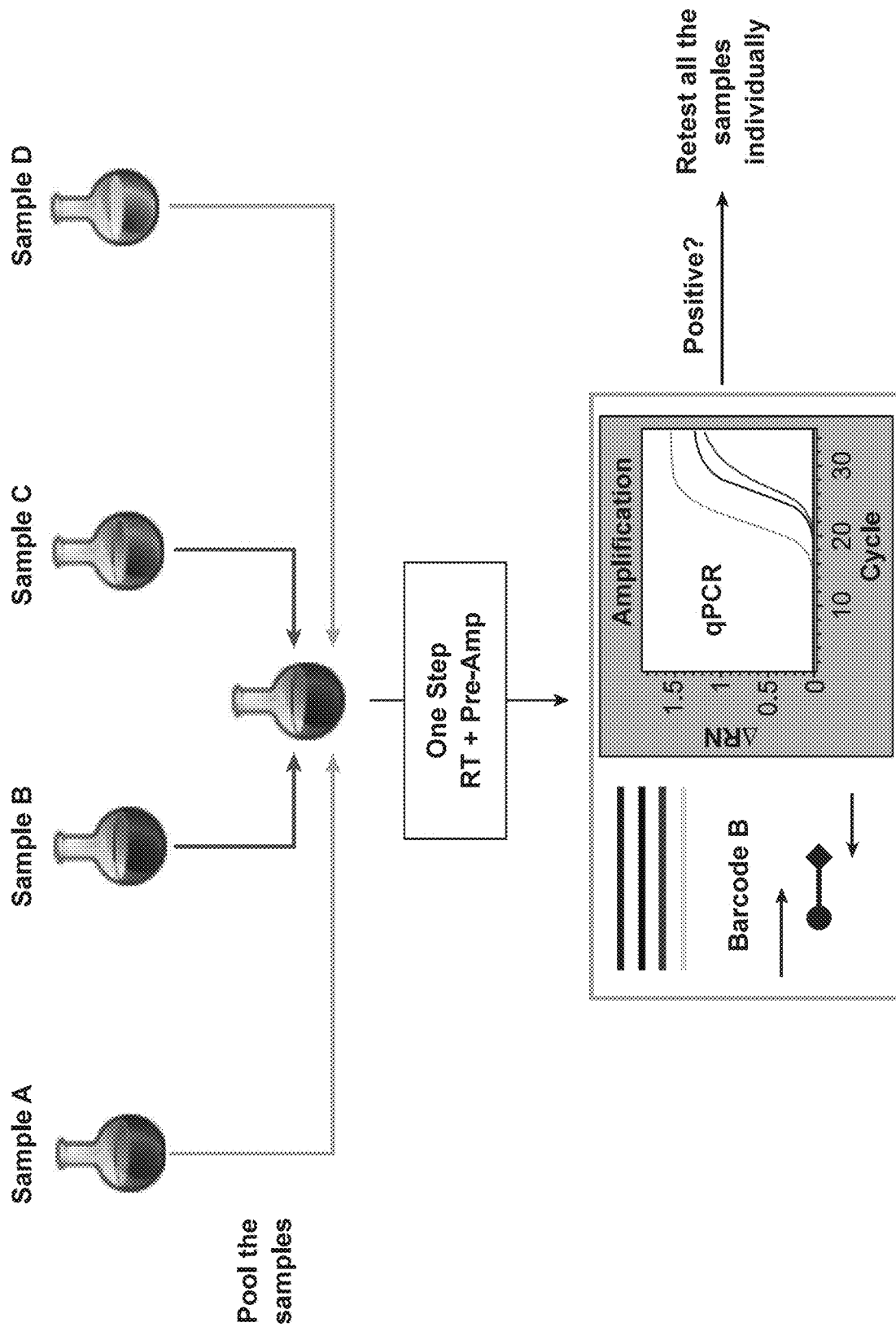
FIG. 21 shows a simple Dorfman pooling method.

FIG. 21 shows a simple Dorfman pooling method in which samples are not barcoded and are not split into separate reaction sites after mixing. Retesting individual samples if the pool of samples is positive for a target nucleotide sequence requires additional steps and reagents.

Figure 22B:
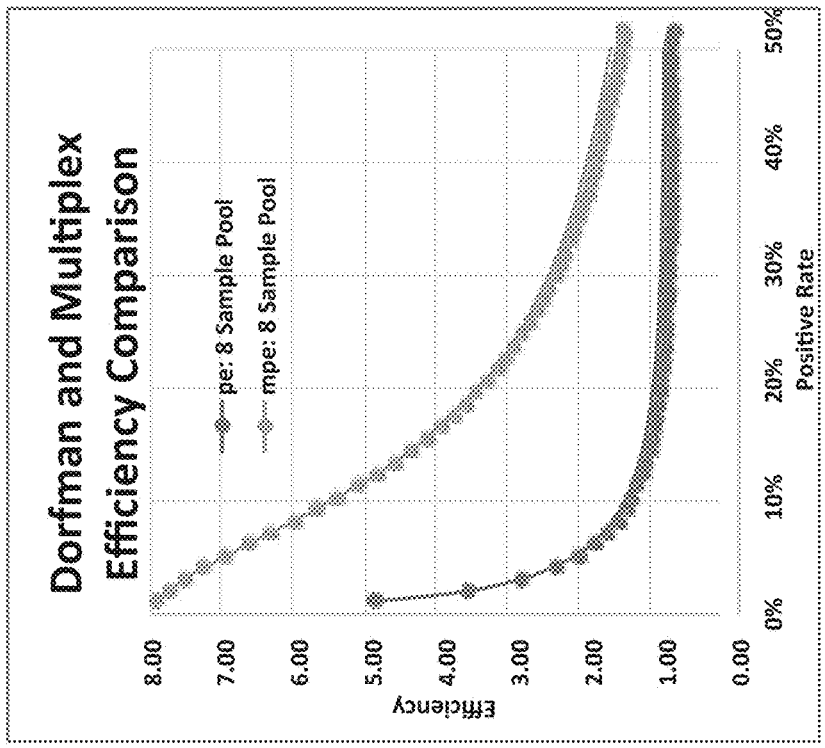
FIG. 22B shows the efficiency when 8 samples are mixed.
Figure 22A:
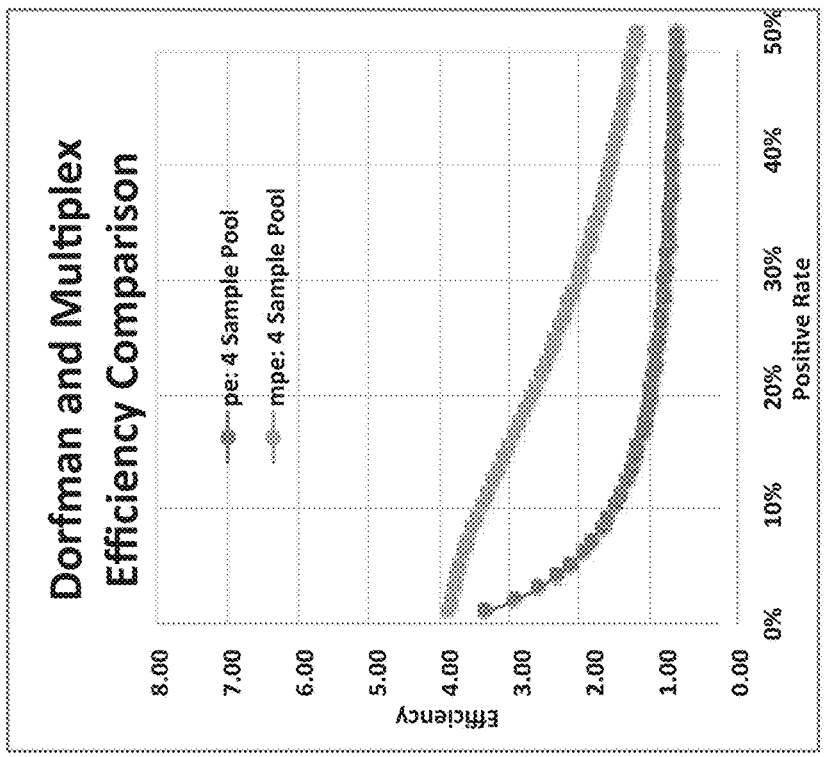
FIG. 22A shows the efficiency of the multiplex sample barcoding (mpe) and Dorfman pooling (pe) methods when 4 samples are mixed.

FIG. 22 shows the efficiency of the multiplex sample barcoding (mpe) and Dorfman pooling (pe) methods when 4 samples are mixed (A) or 8 samples are mixed (B). An increase in efficiency can allow for a reduction in sample handling, in reagents, and in space used on the microfluidic device.

Figure 23:
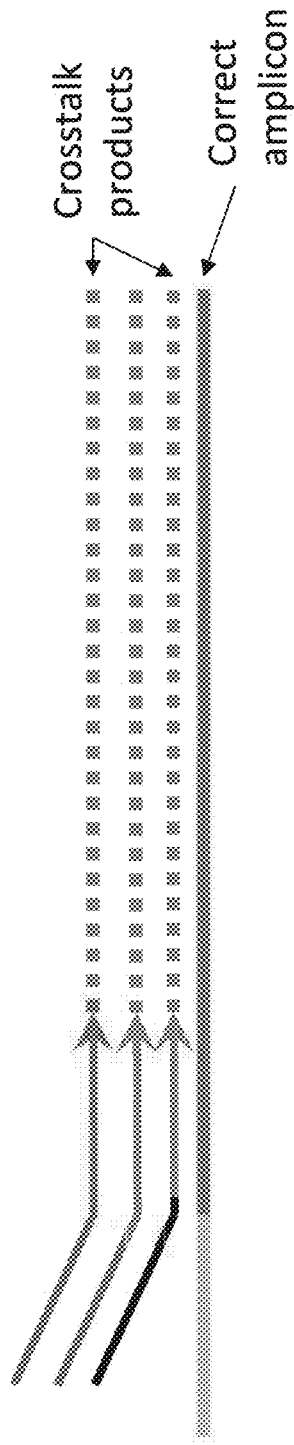
FIG. 23 shows crosstalk that can occur when using the multiplexed sample barcoding approach of FIG. 20.

FIG. 23 shows the mechanism by which crosstalk can occur when using the multiplexed sample barcoding approach of FIG. 20. Specifically, leftover tagged target specific primers may react with tagged target nucleotide sequences from another sample after the samples are mixed, leading to background.

Figure 24:
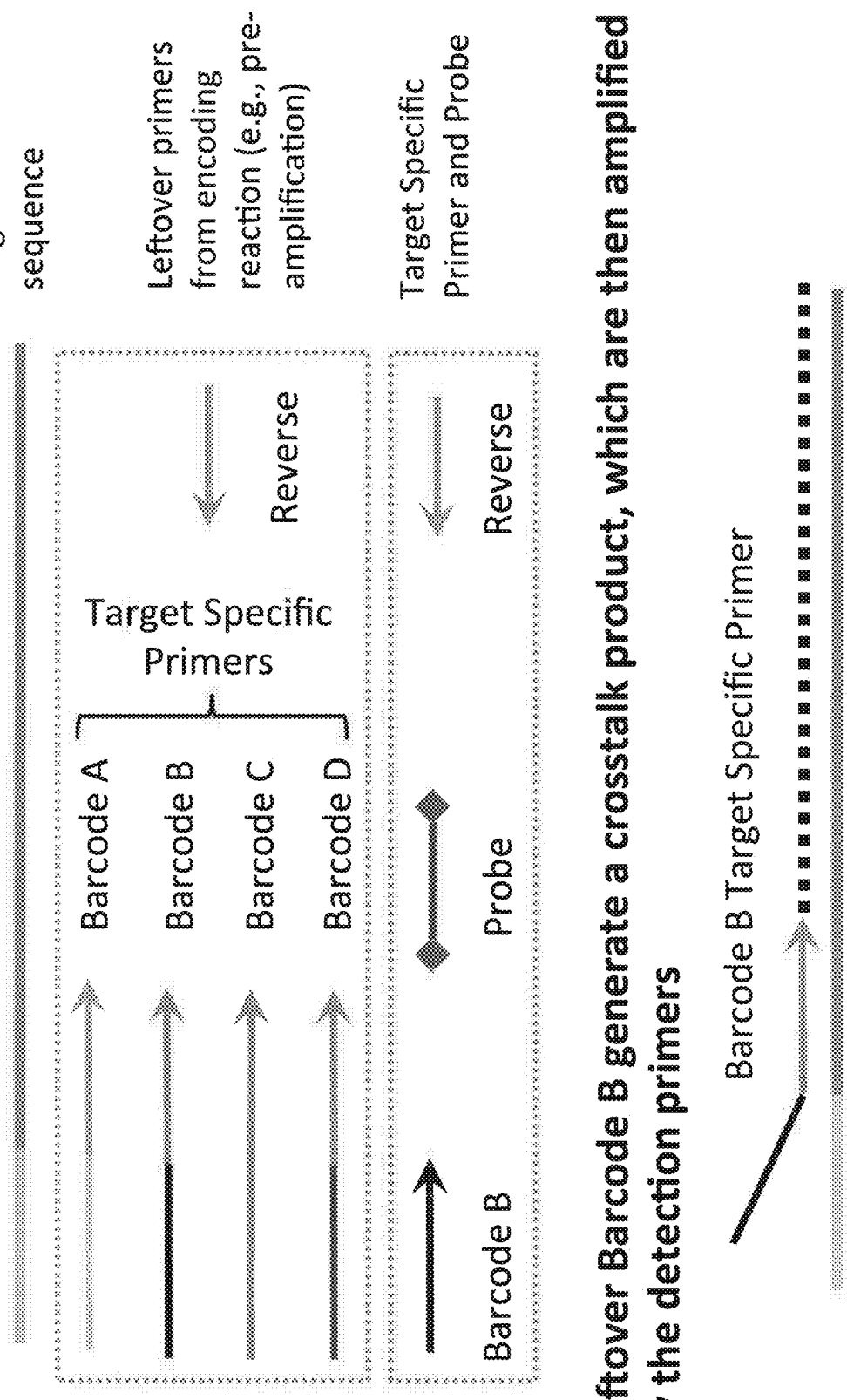
FIG. 24 provides a reaction scheme in which leftover primer from a negative sample (i.e., sample B that does not have a target nucleotide sequence) may react with the preamplified target nucleotide sequence from a positive sample (sample A).

FIG. 24 provides a reaction scheme in which leftover primer from a negative sample (i.e., sample B that does not have a target nucleotide sequence) may react with the preamplified target nucleotide sequence from a positive sample (sample A) after the samples are mixed together, leading to background (e.g., leading to a lower cycle threshold (CT) in a reaction site for detecting the target in sample B). The probe does not compete with the leftover primer.

Figure 25:
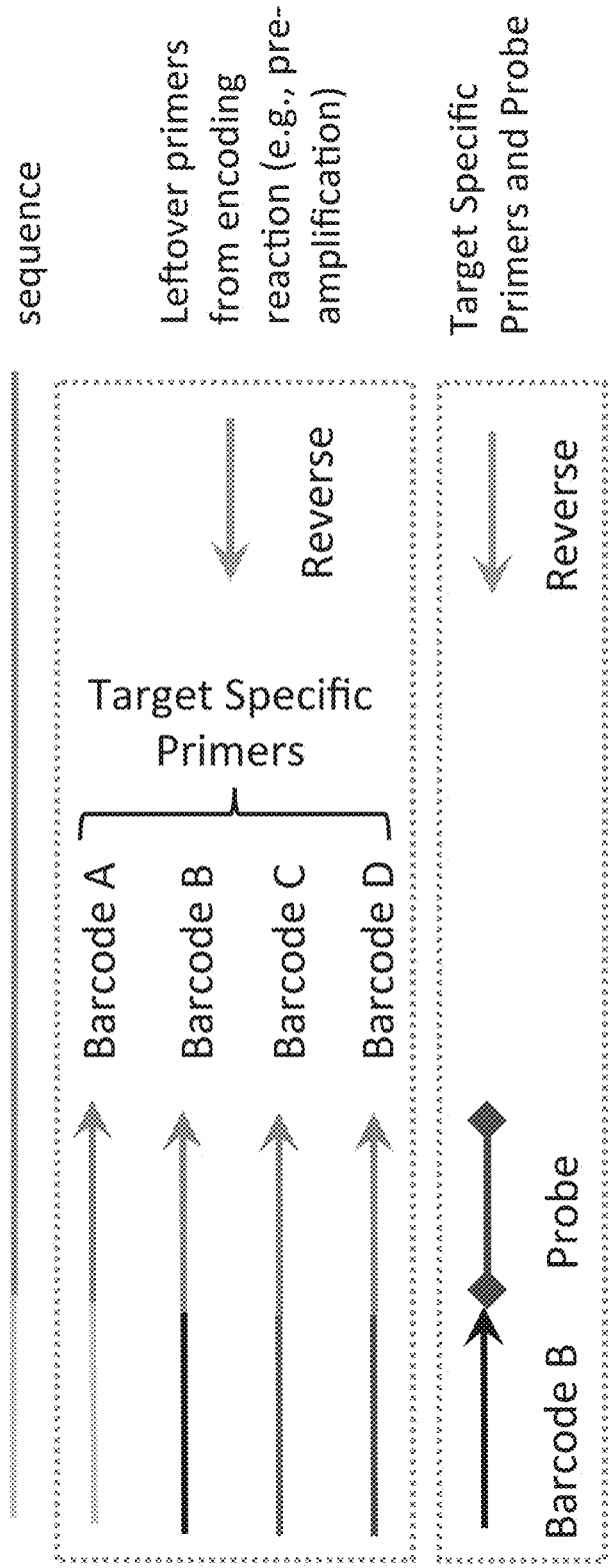
FIG. 25 provides a reaction scheme in which target specific probe competes with leftover primer.
Figure 25:
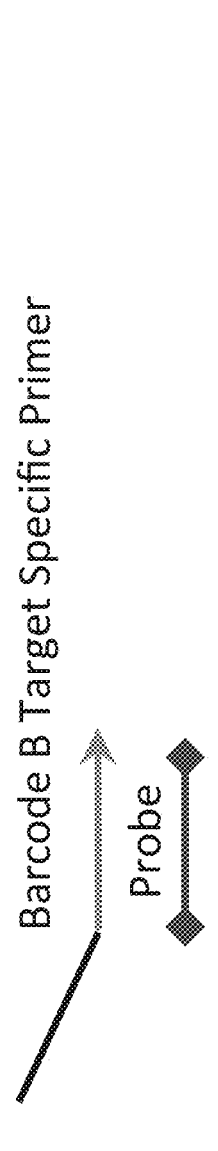

FIG. 25 provides a reaction scheme in which target specific probe competes with leftover primer (i.e., with barcoded target specific primer, also referred to herein as tagged target specific primer) for binding to the preamplified target nucleotide sequence reduces crosstalk.

Figure 26:
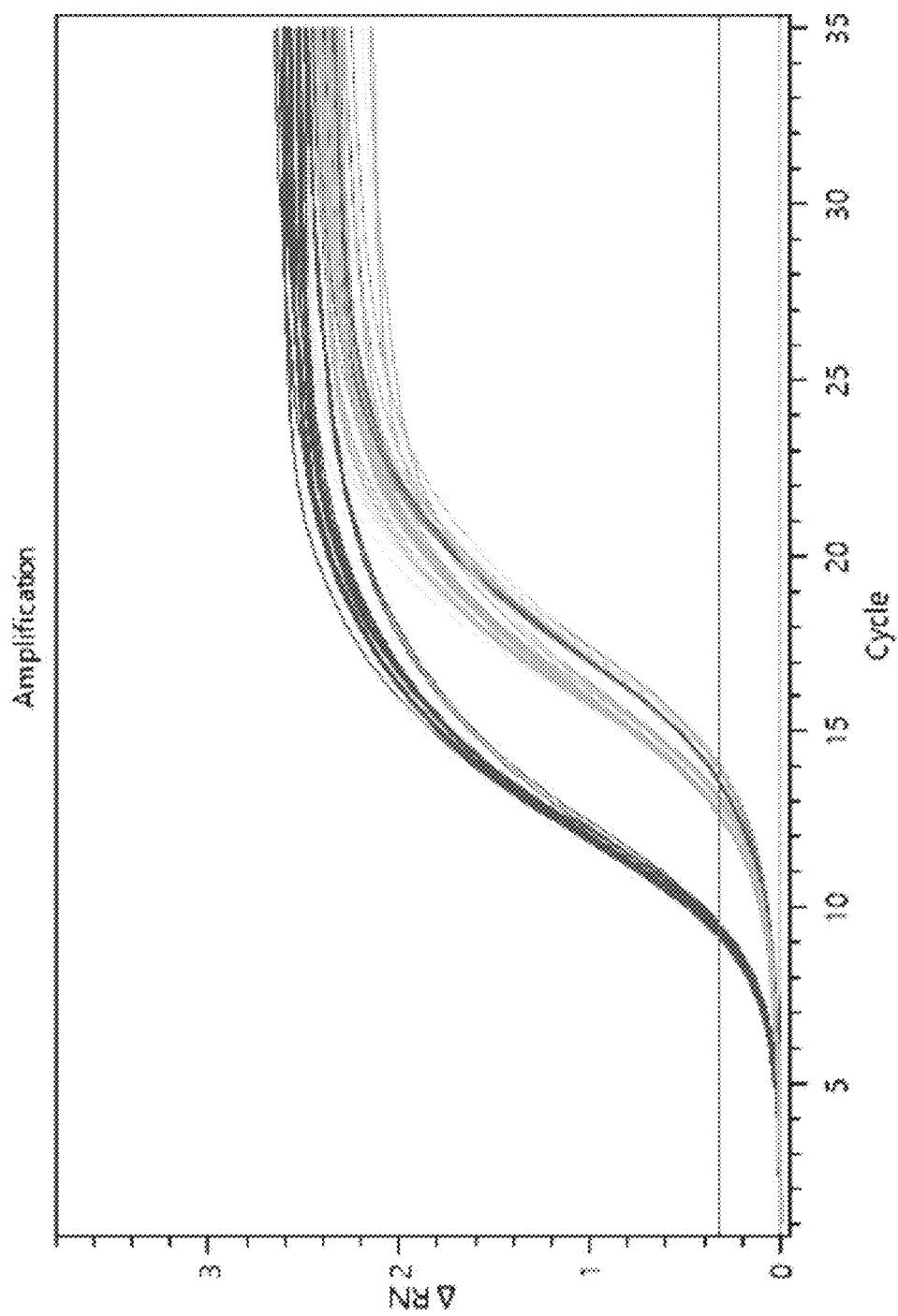
FIG. 26 shows qPCR curves under the scheme of FIG. 24.

FIG. 26 shows qPCR curves for a set of four samples in triplicate in which the first sample (black line) is positive and the other samples are negative for a target nucleotide sequence.

FIG. 26 shows qPCR curves for a set of four samples in triplicate in which the first sample (black line) is positive and the other samples are negative for a target nucleotide sequence, under the scheme of FIG. 24.

Figure 27:
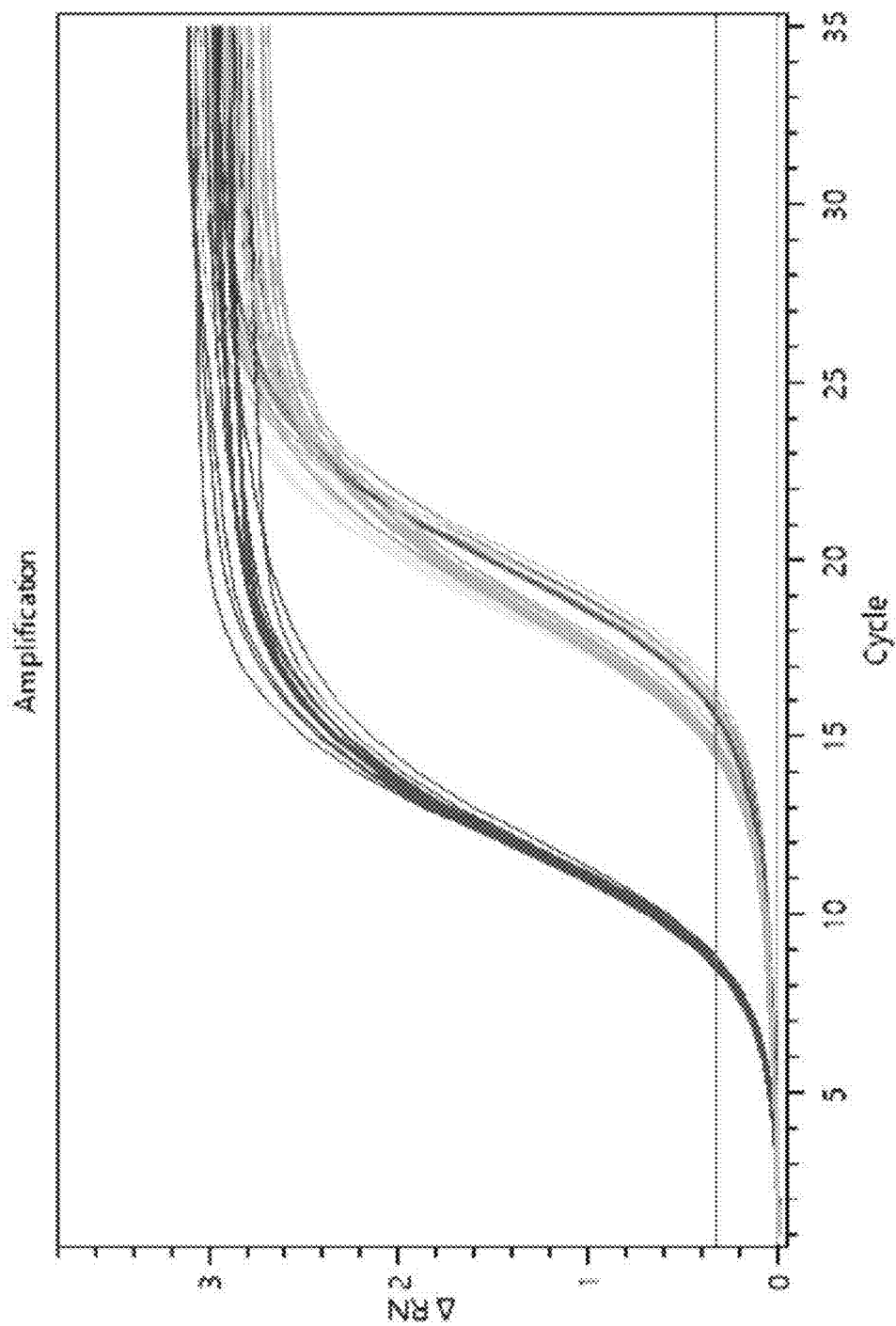
FIG. 27 shows qPCR curves under the scheme of FIG. 25, demonstrating a CT increase of 2 for negative samples compared to FIG. 26.

FIG. 27 shows qPCR curves for a set of four samples in triplicate in which the first sample (black line) is positive and the other samples are negative for a target nucleotide sequence, under the scheme of FIG. 25, demonstrating a CT increase of 2 for negative samples compared to FIG. 26.

In certain aspects, an assay method for detecting at least one target nucleic acid in a plurality of samples includes:
a) reverse transcribing and preamplifying a target nucleotide sequence in each of S separate samples to produce a tagged target nucleotide sequence from each sample, wherein at least one of the S samples includes the target nucleotide sequence,
wherein the tagged target nucleotide sequence includes a sample tag and a target nucleotide sequence,
wherein preamplifying is with a tagged target-specific primer that includes a sample tag and a target-specific sequence, and
wherein the target-specific sequence hybridizes to a portion of the target nucleotide sequence;
b) mixing the tagged target nucleotide sequences of each of the S samples to produce a mixture of tagged target nucleotide sequences;
c) splitting the mixture into a plurality of reaction sites;
d) adding different primer pairs to each reaction sites;
e) amplifying the tagged target nucleotide sequence from a different sample in each reaction site,
wherein each different primer pair includes a primer that hybridizes to a different sample tag; and/or
f) detecting the presence of the of the amplified tagged target nucleic acid by qPCR with a fluorescent target-specific probe that includes at least a portion of the target-specific sequence but does not include a sample tag;
wherein step e of amplifying is in the presence of the target-specific probe.

More generally, an assay method for detecting at least one target nucleic acid in a plurality of samples may include:
a) separately subjecting each of S samples to an encoding reaction that produces a tagged target nucleotide sequence using at least one tagged target-specific primer, wherein at least one of the S samples includes the target nucleotide sequence (i.e., that hybridizes to a strand of the target nucleotide sequence) and wherein the tagged target nucleotide sequence includes a sample tag and a target nucleotide sequence;
b) mixing the tagged target nucleotide sequences of each of the S samples to produce a mixture of tagged target nucleotide sequences;
c) splitting the mixture into a plurality of reaction sites;
d) adding different primer pairs to different reaction sites, wherein each different primer pair includes a primer that hybridizes to a different sample tag to amplify a tagged target nucleotide sequence from a specific sample;
e) amplifying the tagged target nucleotide sequence from the at least one of the S samples in the presence of a target-specific probe, wherein the target-specific probe includes a sequence identical to at least a portion of a target-specific sequence of the target-specific primer but does not include a sample tag; and/or
f) detecting the presence of the tagged target nucleotide.

The target-specific probe may include sequence identical to at least 6 nucleotides (e.g., at least 12 nucleotides long, or at least 18 nucleotides long, such as between 6 and 30 nucleotides long) of the target-specific sequence of the target-specific primer. Alternatively or in addition, the tagged target nucleotide sequence may include a sample tag that is at least 4 nucleotides long, (e.g., at least 6 nucleotides long, at least 12 nucleotides, or at least 18 nucleotides long, such as between 6 and 30 nucleotides long). Alternatively or in addition, the target-specific sequence is at least 6 nucleotides long (e.g., at least 12 nucleotides long, or at least 18 nucleotides long, such as between 6 and 30 nucleotides long). Alternatively or in addition, the target nucleotide sequence may be at least 50 nucleotides long (e.g., at least 100 nucleotides long, at least 150 nucleotides long, such as at or between 50 and 300 nucleotides long).

In certain aspects, step a) includes reaction with a tagged primer that includes the sample tag but does not include the target nucleotide sequence, for example, wherein the tagged primer is at a higher concentration than the tagged target-specific primer.

A target-specific primer that does not include the tag and is the reverse complement to a portion of the target nucleotide sequence may be used (e.g., to reverse transcribe and/or amplify the tagged target nucleotide sequence). Step a) may further includes reverse transcribing the target nucleotide sequence using the target-specific primer.

In certain aspects the the tagged target-specific primer includes uracil, such as when the method further includes adding a uracil N-glycosylase (UDG) to the mixture of tagged target nucleotide sequences to degrade leftover tagged target specific primer.

In certain aspects, at least one of the S samples includes the target nucleotide sequence and at least one of the S samples does not include the target nucleotide sequence A method may further include reverse transcribing the tagged target nucleotide sequence, using a target-specific primer, prior to step a). Alternatively, step a) may include preamplifying the tagged target nucleotide sequence (e.g., in the same reaction).

In certain aspects, step e) may be performed at least in duplicate. In certain aspects, at least one of the S samples does not include the target nucleotide sequence. Step f) of detection may be by PCR, such as endpoint PCR or qPCR. When detection is by qPCR, the target-specific probe (e.g., its completion with the tagged target specific primer) may increase the CT by at least 1, at least 2, at least 4, or at least 6 in a reaction site where the primer pair is specific for a sample that does not include the target nucleotide sequence. For example, the presence of the target-specific probe increases the dCT between a reaction site where the primer pair is specific for a sample that does not include the target nucleotide sequence and a different reaction site where the primer pair is specific for a sample that does not include the target nucleotide sequence by at least a dCT of 1, 2, 4 or 6, such as a 20% increase in dCT or a 40% increase in the dCT. In certain aspects, the target specific probe may reduce binding of leftover tagged target specific primer to tagged target nucleotide sequence by at least 25%, at least 50%, or at least 75%. In certain aspects the probe may be in at least 5 times, at least 10 times, or at least 20 times in excess of leftover tagged target specific probe in the mixture.

In certain aspects, step f) of detecting includes detecting a signal from the target-specific probe. For example, the probe may include a fluorophore and optionally further a quencher, e.g., such that the fluorophore is quenched when the probe is not hybridized to the target nucleotide sequence and such that the probe fluoresces upon hybridization.

Any of the method steps may be performed on a microfluidic device of the subject application. In certain aspects, least steps e) and f) are performed on an array microfluidic device including an array of reaction sites. For example, at least steps c) through f) are performed on an array microfluidic device including an array of reaction sites. In another example, all of steps steps a) through f) are performed on an integrated microfluidic device including sample processing unit cells and an array of reaction sites. Such an integrated microfluidic device may be of any embodiment described herein. For example, individual reaction sites of the array of reaction sites of the device may include a unique combination of a sample inlet and a reagent inlet. In certain aspects, step c) includes flowing the mixture of step b) into a sample inlet of the array microfluidic device. In certain aspects, the number of inlets to a microfluidic device may be restricted based on physical limitations such as the substrate of the device or, the pressure needed to drive fluid through small channels, and/or alignment of wells in a carrier of the device with inlet channels in the microfluidic device. As such, dense arrays (e.g., including more than 200 reaction sites across a square centimetre) may not have enough inlets to direct a different sample to each reaction site. As such, sample barcoding of the subject application can provide the ability to pool sample barcoded samples, flow them through the same channel, and detect the presence of a target with a different sample barcode in different reaction sites.

In certain aspects, target-specific probe does not include a label (e.g., it is a competition probe that does not provide any fluorescent signal). In such aspects, step f) of detecting is with a labelled target specific probe that does not compete with the tagged target-specific primer for binding to the target specific nucleotide sequence. For example, step f) of detecting is with an intercalating dye such as SYBR Green.

In certain aspects the number of samples S is at least 2, at least 4, at least 8, or at least 16, such as at or between 4 and 8.

Method of sample barcoding may further include flowing the mixture of tagged target nucleotide sequences from step c through a single channel that splits into the plurality of reaction sites of step d. For example, the single channel may be a sample inlet to a plurality of reaction sties, e.g., each reaction site including a sample chamber and a assay chamber as described herein. The plurality of reaction sites are separate locations of an array microfluidic device, and the method may further include fluidically isolating the reaction sites from one another prior to step e of detecting the tagged target nucleic acids.

In certain aspects T different target nucleotide sequences in the same sample are tagged with the same sample tag but are detected in separate reaction sties. The tagged target nucleotide sequence may include a unique combination of a sample tag and a target-specific tag. For example, step a) may further include a target specific reverse primer that includes the target-specific tag but does not include the sample tag. A reaction site may amplify a specific target from a specific sample using a primer to the sample tag and a primer to the target-specific tag. A reaction site may amplify a specific target from a specific sample using a primer (e.g., reverse primer) to the sample tag and a primer to the target nucleotide sequence. Optionally further, each target is detected with a target-specific probe. Step e) of amplifying may include loading each reaction site with a primer pair specific for a particular combination of a sample tag and a target specific tag, e.g., such that wherein each of the SxT combinations are amplified in a separate reaction site. In certain aspects, T may be at least 3, at least 4, or at least 6. In certain aspects, the target nucleotide sequence is a viral nucleotide sequence, such as a viral RNA sequence (e.g., an influenza or SARS-CoV-2 viral RNA sequence). For example, the T different target nucleotide sequences include an H3N2 Influenza RNA sequence and a H1N1 Influenza RNA sequence. Alternatively or in addition the T different target nucleotide sequences include at least two of an N1, N2, and N3 and SARS-CoV-2 sequence.

As described herein, the sample may be any biological sample such as a blood sample (e.g., serum, plasma or whole blood), saliva, a nasal swab, or derived from solid tissue.

Sample Barcoding for Sequencing and/or PCR Detection

Crosstalk may also occur when sample indexing (barcoding) prior to mixing and sequencing, in particular when there are amplification steps after mixing indexed samples. An assay method for detecting at least one target nucleic acid in a plurality of samples may include:
  a) separately subjecting each of S samples to an encoding reaction that produces a tagged target nucleotide sequence using at least one tagged target-specific primer, wherein at least one of the S samples includes the target nucleotide sequence and wherein the tagged target nucleotide sequence includes a sample tag and a target nucleotide sequence;
  b) mixing the tagged target nucleotide sequences of each of the S samples to produce a mixture of tagged target nucleotide sequences;
  c) amplifying the tagged target nucleotide sequence from the at least one of the S samples in the presence of a target-specific probe, wherein the target-specific probe includes a sequence identical to at least a portion of a target-specific sequence of the target-specific primer but does not include a sample tag; and/or
  d) detecting the presence of the tagged target nucleotide.

In certain aspects step d) of detecting is by sequencing the amplified tagged target nucleotide sequences. Step a) of encoding may include incorporating a sequencing adaptor sequence into the tagged target nucleotide sequence. Step a) may be performed on a microfluidic device including sample processing unit cells, and tagged target nucleotide sequence may be collected from the microfluidic device before step b) of mixing. Alternatively or in addition, step d) of detecting includes PCR (e.g., qPCR).

Kits for Sample Barcoding

The subject application also includes kits for performing any of the above methods. For example, a kit may include a microfluidic device of any one of embodiments and/or may include one or more reagents for performing the methods of any one of the above methods. Such reagents may be selected from one or more of an RNAse inhibitor, reverse transcriptase, polymerase, a preamplification mix (e.g., including a plurality of primer pairs that specifically amplify different target nucleotide sequences), beads that specifically capture sample biomolecules of interest as described herein, primers, probes, oligonucleotide-conjugated antibodies, enzymes of cleaving oligonucleotide from the antibodies they are conjugated to, or any other suitable reagent for performing the methods of the subject application.

A kit for detecting at least one target nucleic acid in a plurality of samples may include:
   a tagged target-specific primer for each of S samples, wherein each tagged target-specific primer includes a sample tag and a target-specific sequence, and
   a target-specific probe that includes at least a portion of the target-specific sequence; wherein each of the tagged target-specific primers and the probe are in separate partitions.

The kit may further include one or more of a strand displacing polymerase (e.g., that displaces the probe when during an amplification reaction), a reverse transcriptase, and RNAse inhibitor, or any buffers, master mixes or other components the for subject methods.

In certain aspects, the tagged target-specific primer is in mixture with a target specific reverse primer that and does not include a sample tag. The reverse primer may include a target specific tag. The reverse primer would hybridize the revere complement of the target nucleotide sequence strand that the tagged target-specific primer hybridizes to. In certain applications, the reverse primer hybridizes to an mRNA target-specific sequence to enable reverse transcription.

The kit may further include a set of S different primers that each hybridize to a different sample tag, wherein each of the S different primers is in a separate partition. At least some of the S different primers may be in admixture with a target specific reverse primer. The kit may further include a target specific reverse primer, e.g., wherein the target specific reverse primer does not include a sample tag.

The probe and/or primers of the kit may be of any of the aspects described for the methods herein. The kit may further include a microfluidic device of any aspects of the subject application. The microfluidic device is and elastomeric device. The microfluidic device may be an array device including a plurality of reaction sites, e.g., wherein individual reaction sites include a unique combination of a sample inlet and a reagent inlet. In certain aspects the microfluidic device further includes sample processing unit cells, for example, when a plurality of samples bound to beads are mixed and an encoding reaction and/or preamplification of encoded products is performed on the microfluidic device (e.g., by splint ligation workflow described herein).

3 Primer Sample Barcoding

Another approach to reducing crosstalk in sample barcoding is a three primer approach described herein.

Figure 28:
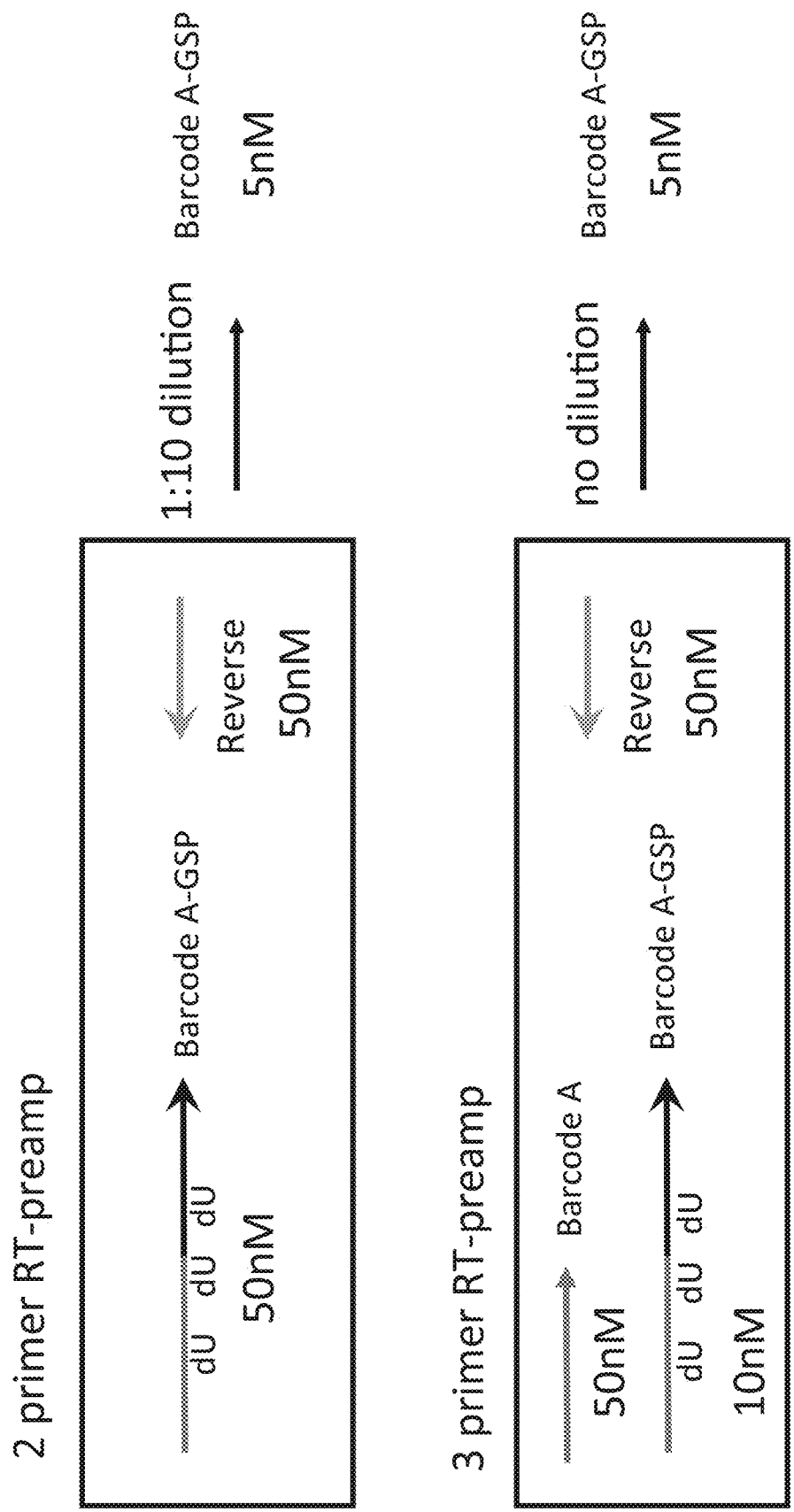
FIG. 28 shows another approach to reducing cross talk.

FIG. 28 shows another approach to reducing cross talk, in which UDG is used to degrade leftover primer (top) and the probe (GSP) does not compete with leftover primer. Alternatively or in addition, the concentration of the tagged target specific primer can be below the concentration of a tag primer that is not target specific, such that the tagged primer takes. The tagged primer would not be expected to create crosstalk after mixing, as it is not target specific.

In certain aspects, an assay method for detecting at least one target nucleic acid in a plurality of samples may include:
   a) separately subjecting each of S samples to an encoding reaction that produces a tagged target nucleotide sequence using at least one tagged target-specific primer, wherein at least one of the S samples includes the target nucleotide sequence;
   b) mixing the tagged target nucleotide sequences of each of the S samples to produce a mixture of tagged target nucleotide sequences;
   c) splitting the mixture into a plurality of reaction sites;
   d) adding different primer pairs to different reaction sites, wherein each different primer pair includes a primer that hybridizes to a different sample tag;
   e) amplifying the tagged target nucleotide sequence from a different sample in each reaction site; and/or
   f) detecting the presence of the tagged target nucleotide; wherein step a) includes reaction with a tagged primer that includes the sample-specific tag but does not include the target nucleotide sequence.

The tagged primer may be at a higher concentration (e.g., at least 5 times higher, at least 10 times higher, or at least 20 times higher) than the tagged target-specific primer. The method may include a target-specific primer that does not include the tag and is the reverse complement to a portion of the target nucleotide sequence. Step a) may further include reverse transcribing the target nucleotide sequence using the target-specific primer. The tagged target-specific primer may include uracil, e.g., when the method further includes adding a uracil DNA-glycosylase (UDG) to the mixture of tagged target nucleotide sequences to cleave (i.e., degrade) the tagged target-specific primer.

A kit for detecting at least one target nucleic acid in a plurality of samples, may therefore include:
   a tagged target-specific primer for each of S samples, wherein each tagged target-specific primer includes a sample-specific tag and a target-specific sequence, and
   a tagged primer that includes the sample-specific tag but does not include the target nucleotide sequence.

Allele Detection

Alleles of a gene, such as of a viral gene, are often detected by sequencing or by genotyping PCR (end point PCR). Discussed herein are methods and kits for qPCR (i.e., real time PCR) detection of alleles, such as by for identification of the presence of one or more alleles by comparison of CT values between different allele qPCR reactions. In the subject methods and kits, the presence of at least 1, at least 2, at least 3, at least 4, or at least 6 alleles may be identified. The gene sequence may be preamplified, such as by a preamplification primer pair that amplifies all of the alleles (i.e., a pair of primers that specifically hybridize sequences of the gene conserved across the alleles), prior to splitting into a plurality of reaction sites (e.g., wells, droplets, chambers, etc.) for separate qPCR detection by allele-specific primer pairs. In certain aspects, the same probe (e.g., that specifically hybridizes a gene sequence conserved across the alleles, such as a gene sequence positioned between the gene sequences hybridized by the allele-specific primer pairs) may be used to detect the qPCR product of different alleles in the different reaction sites. For example, steps of preamplification, splitting, and qPCR may be performed as shown in FIG. 29, and optionally further, a step of identifying the presence of an allele may be performed base on a dCT threshold as shown in FIG. 30.

The allele detection methods and kits described herein may use any microfluidic device described further herein, or by any tube or multi-well plate based workflow (i.e., such that no steps are performed on a microfluidic device described herein). For example, a preamplification may be performed in a tube or multi-well plate format and preamplified sample loaded on an array of a microfluidic device for the step of qPCR detection. In another example, preamplification (and optionally bead-based capture of gene) may be performed on a unit cell of a microfluidic device which is integrated with an array of reaction sites for the step of qPCR detection. In cases where the sample includes an RNA sequence of the gene, reverse transcription may be performed to produce a cDNA sequence of the gene prior to preamplification of the cDNA sequence. For example, reverse transcriptase and polymerase may be in the same preamplification mixture such that reverse transcription occurs in the same reaction volume as the preamplification.

An allele-specific primer pair has at least on primer (optionally two primers) of the pair (i.e., at least one allele-specific primer) that specifically hybridizes and extends along the target allele. For example, the 3' end of an allele-specific primer may be complementary to a single nucleotide polymorphism (SNP) that distinguishes the allele. Alternatively, a portion of the allele-specific primer (e.g., at the 3' end) may be complementary to an insertion sequence that distinguishes the allele, or may be lacking a deletion sequence that distinguishes the allele and instead be complementary to a sequence following the deletion sequence. As such, one or more allele-specific primers (e.g., of different allele-specific primer pairs) may be specific for a SNP, an insertion or a deletion variant site. An insertion or deletion sequence may be a single nucleotide in length, or more than 2, more than 5, or more than 10 nucleotides in length. In certain aspects, at least one allele is a "wildtype" allele and another allele is a "mutant" allele that has a SNP or indel (insertion or deletion) mutation compared to the wildtype allele. In general, a primer may be at least 12, at least 15, or at least 20 nucleotides in length. A primer may include non-target sequences (e.g., such as an adaptor or sample barcode), but the target specific sequence of the primer may be at least 12, at least 15, or at least 20 nucleotides in length.

The method may include heat treating the sample or otherwise treating the sample to make viral RNA available for reverse transcription), for example, after capturing viral particles on beads or before capturing viral RNA on beads as described herein.

The method may include identifying the presence of at least 4 different alleles (e.g., in which the at least 4 different alleles were all preamplified, such as by the same preamplification primer pair). One of the at least 4 different alleles may include a SNP variant site compared to a "wildtype" allele of the at least 4 different alleles, and optionally further, another of the at least 4 alleles may include an indel variant site compared to the "wildtype" allele of the at least 4 different alleles. In certain aspects, a plurality of samples (e.g., at least 12, at least 24, at least 48, or at least 96 samples) are processed in parallel on the same microfluidic device, and the presence of the at least 4 different alleles is identified for each sample.

A wildtype allele may be identified based on its prevelance (or historic prevelance in a population), or based on its role in the subject methods and kits (i.e., the CT of other alleles ("mutants") are compared to the CT of the wildtype allele to identify the presence of the mutant alleles).

In general, the use of the same preamplification primer pair and/or at least one primer of the allele-specific primer pairs may allow for direct comparison of the CT across different allele-specific qPCR reactions to identify the presence of an allele in the sample. For example, a "mutant" allele may be non-specifically amplified by a "wildtype" specific primer pair at lower efficiency than amplification by a "mutant" specific primer pair in a separate reaction site. Because the preamplification primers are designed to amplify both mutant and wildtype alleles of the gene, and/or because one of the primers of both the mutant and wildtype specific primer pairs may be conserved, a direct comparison of CT may be useful for reliably identifying the presence of the mutant allele. As such, the dCT of the mutant compared to the wildtype (dCT=CTmut−CTwt) would be lower the more of the mutant allele is present in the sample compared to the wildtype allele.

In certain aspects, a method of detecting the presence of at least one of a plurality of alleles of a gene in a sample may include one or more steps of: preamplifying a gene by PCR to obtain a preamplified sample such that a plurality of alleles of the gene would be amplified by the same preamplification primer pair; separating a sample (e.g., the preamplified sample) into a plurality of reaction sites; and/or detecting a cycle threshold (CT) of each of the plurality of alleles in a separate reaction site of the plurality of reaction sites, wherein detection is by qPCR and wherein each allele is specifically amplified with a different allele-specific primer pair. A different allele-specific primer pairs may differ in at least one primer that selectively amplifies (extends, in the presence of polymerase) a specific allele (or subset of alleles) of the plurality of alleles. An allele-specific primer may have a 3' sequence (e.g., one or more nucleotides) complementary to a variant site (e.g., SNP or indel) of an allele. Two allele-specific primers may together be used to amplify an allele characterized by two variant sites, or a single allele-specific primer may be used to amplify an allele characterized by a single variant site and the second primer of the allele-specific primer pair may be conserve across one or more other allele-specific primer pairs.

In certain aspects, the method may include detecting the presence of at least 3 alleles, at least 4 alleles, at least 5 alleles, or at least 6 alleles, such as between 2 and 6 alleles or between 4 and 6 alleles. The method may further include detecting the presence of the alleles across at least 12 samples, such as across at least 24 samples, at least 48 samples, or at least 96 samples. For example, an integrated microfluidic device as disclosed herein may have at least 96 sample inlets (each in fluidic communication with a unit cell for sample processing as described herein), and at least 12 assay inlets (each allowing introduction of a different assay mix as described herein, although multiple assay inlets may be used for the same assay mix to allow for replicate reactions). In certain aspects, the integrated microfluidic device has 124 sample inlets and 24 assay inlets.

In certain aspects, a plurality of different genes may be preamplified in the same reaction mixture and a plurality of alleles of each the different genes detected by qPCR after splitting the preamplification mixture into a plurality of different reactions sites. The presence of the alleles of the different genes may then be identified as described further herein.

In certain aspects, at least one of step of preamplifying, splitting and detecting is performed on a microfluidic device, such as an elastomeric microfluidic device. The microfluidic device may include an array of reaction sites, e.g., such that individual reaction sites of the array of reaction sites may include an assay chamber and a sample chamber. Sample inlets may provide sample to the sample chambers and assay inlets may provide assay reagents to the assay chambers. For example, allele-specific primers (or an allele-specific primer pair including at least one allele-specific primer), may be loaded into the assay inlets. Probe may be loaded into the assay inlets, or with a preamplification mix.

In certain aspects, each step of preamplifying, splitting and detecting is performed on a microfluidic device, such as an integrated microfluidic device described herein. For example, the microfluidic device may be an integrated microfluidic device including: an array of reaction sites; and a plurality of sample processing unit cells including a plurality of sample processing sites. Individual unit cells may be in fluidic communication with a plurality of different reagent inlets, such as wherein sample inlets to the array are downstream of the plurality of sample processing sites of the plurality of unit cells. Individual unit cells may include a column configured to retain beads (e.g., may include a sieve architecture as described herein).

The gene may be a viral gene, such as of an RNA virus. The method may further include capturing a viral RNA sequence of the gene on the beads through hybridization to a ssDNA sequence prior to step of preamplifying. The method may further include eluting the viral RNA sequence and preamplifying the eluted viral RNA sequence to produce a cDNA sequence of the gene prior to the step of preamplifying. The method may further include reverse transcribing the viral RNA sequence captured on the beads to produce a cDNA sequence of the gene prior to step of preamplifying.

The method may include capturing viral particles of the sample with antibody conjugated to the beads prior to step of preamplifying (e.g., wherein the gene is a viral gene). The capture of viral particles may be before an extraction (e.g., RNA extraction) or heating step to make RNA (or DNA) from the viral particle accessible to the later steps of reverse transcription and/or preamplification.

In certain aspects, another format such as a multi-well plate combined with a liquid handler (e.g., including an automated multi-pipette arm), may be used to perform part or all of the subject method of allele detection.

Wherein qPCR of the alleles step of detecting uses the same probe across the plurality of reaction sites in which different alleles of the gene are detected. The probe may include a fluorophore and a quencher (e.g., such as a TakMan probe). The probe may specifically hybridize to a sequence of the gene conserved across the different alleles. In certain aspects, an allele-specific probe may be used, for example, if the allele is defined by another variant site in addition to the variant site specifically amplified by the allele-specific primer pair. In certain aspects, the probe may specifically hybridize to the variant site specifically amplified by the allele-specific primer pair. The method may also include use of probes to additional genes preamplified and detected by qPCR (e.g., introduced in the preamplification mixture or in an assay mixture to reaction sites where one of the additional genes is amplified and detected by qPCR). In certain aspects, a dye such as SYBR Green, may be used instead of a target specific probe.

The step of preamplifying further may include amplifying additional genes with additional preamplification primer pairs. The additional primer pairs may include a primer pair specific for at the SARS-CoV-2 N1 gene or the SARS-CoV-2 N2 gene (e.g., wherein the alleles include SARS-CoV-2 spike S1 alleles).

At least one allele may be amplified in the step of detecting with two allele-specific primers specific for different variant sites of the allele. Alternatively or in addition, at least two alleles are amplified in the step of detecting with the same reverse primer or the same forward primer.

FIG. 29 shows a multi-step process for detecting specific alleles of a gene in a sample according to the subject methods. In a preamplification step, a pair of preamplification primers (a preamplification forward and reverse primer) amplify a gene, such that multiple alleles would be amplified if present in the sample. Amplification may be in the presence of a polymerase, dNTPs, and any other suitable reagents (e.g., such as a reverse transcriptase to reverse transcribed an RNA prior to amplification of the resulting cDNA sequence). The alleles may differ at one or more variant sites amplified by the preamplification primers. A variant site of an allele may be a single nucleotide polymorphism, an insertion, or a deletion as compared to another allele. In certain aspects, reverse transcription (e.g., of mRNA or viral RNA) may be performed to produce a cDNA sequence of the gene suitable for preamplification. Capture of the gene, reverse transcription, and/or preamplification may be performed on a unit cell of a microfluidic device such as that described in FIG. 3 or 4. Following preamplification, the preamplification products (one or more amplified alleles of the gene, and optionally other genes) may be separated into different reaction sites (e.g., wells, chambers, or droplets). For example the reaction sites may be of an array device as described in FIG. 12. At least some different reaction sites may specifically amplify different alleles with one or more different allele-specific primers, as described further herein. Detection of alleles by qPCR may be performed, for example, with a universal detection probe (specific for the gene sequence but not the alleles). Different probes may be used to detect different genes.

While reverse transcription may be described herein as before the preamplification step, both may occur in the same reaction volume (such that an individual RNA strands are each reverse transcribed before premaplification of the resulting cDNA sequences, but the cDNA of a specific RNA strand may be preamplified while another RNA strand is still being reverse transcribed in the reaction volume).

Methods of detecting alleles may further include a step of identifying the presence of one or more alleles based on CT values obtained from the step of detecting by qPCR. The step of identifying may include identifying if an allele is present or absent from a sample, identifying the amount or proportion of the allele (e.g., compared to one or more other alleles), or may include providing a certainty (likelihood) that the allele is present. The step of identifying may be automatically reported to a user by software. As such, aspects of the subject application include a computer readable medium including instructions to compare a CT value of two alleles detected by qPCR to obtain a dCT value, compare the dCT value to a predetermined threshold, and report the presence of one of the two alleles. The computer readable medium may accept input of the predetermined threshold from the user. The computer readable medium may include instructions to identify one or more other genes preamplified and detected by qPCR (e.g., such as by reporting the presence of SARS-CoV-2 based on detection of the N1 gene and/or the N2 gene). The computer readable medium may further include instructions to execute one or more of the steps of preamplifying, splitting, and qPCR detection described herein for allele detection.

Identifying the presence of an allele in the sample may be based on a difference in the CT values (dCT) of the allele and another allele of the plurality of alleles. The plurality of alleles may include at least one wildtype allele and two or more mutant alleles, e.g., wherein the presence of each of the mutant alleles is identified based on whether a dCT between the wildtype allele and the mutant allele is above or below a predetermined dCT threshold. For example, the predetermined dCT threshold is greater than 1 or less than $-1$, greater than 2 or less than $-2$, greater than 3 or less than $-3$, greater than 5 or less than $-5$, or greater than 8 or less than $-5$. The sign value of the predetermined threshold may be based on, e.g., whether the CT of the mutant allele is subtracted from the CT of the wildtype allele or visa-versa. A mutant allele may be identified as present even if it is present at lower abundance than a wildtype allele in the sample, for example, the mutant allele is present at only 10% (e.g., at 5%) of a wildtype allele in the sample.

The method may further include identifying the presence of a virus based on detection of one or more additional genes preamplified and detected by qPCR as described herein. The method may further identifying a viral load based on the CT of one or more additional genes preamplified in the step of preamplifying and detected by qPCR in the step of detecting The one or more additional genes may include at least one of a SARS-CoV-2 N1 gene and a SARS-CoV-2 N2 gene.

In certain aspects, the CT value of at least one of the alleles of the plurality of alleles is used to report a viral load, e.g., wherein the gene is a viral RNA gene.

Wherein the step of preamplifying may include at least 5 cycles of PCR, 10 cycles of PCR, at least 15 cycles of PCR, or at least 20 cycles of PCR. The CT value for at least one allele of the plurality of alleles may be 10 or greater, 15 or greater, 20 or greater, 25 or greater, or 30 or greater (e.g., wherein the allele is still identified as present in the sample). As such, an allele may be amplified (across a preamplification and qPCR reaction) in at least 35 or at least 40 cycles of PCR, such that as few as 10,000, as few as 1,000, as few as 100 copies, or as few as 10 copies of the allele (e.g., present in the preamplification mixture prior to preamplification cycles) may be detected. In certain aspects, the limit of detection by qPCR in the step of detecting may be a CT between 20 and 35, such as between 25 and 30, between 30 and 35.

In certain aspects, the sample for which alleles are detected by the subject methods or kits is a biological sample such as a blood sample, saliva, a nasal swab, or derived from solid tissue. The gene may be a viral gene, e.g., wherein the sample includes a virus such as an RNA virus (such as SARS-CoV-2). The method may further include reverse transcription of viral RNA to produce a cDNA sequence of the gene prior to the step of preamplifying.

Aspects of allele detection also include kits for performing the methods of allele detection described herein. In addition, methods described herein may include use of one or more aspects of the kits described herein.

A kit for detecting at least one of a plurality of alleles of a gene may include: a preamplification mix, wherein the preamplification mix may include a preamplification primer pair that amplifies a plurality of different alleles of a gene; and a plurality of separate assay mixes, wherein each of the assay mixes may include a different allele-specific primer pair that each selectively amplify one of the different alleles of the gene.

A kit may include a microfluidic device, wherein the microfluidic device may include a plurality of reaction sites, wherein individual reaction sites of the array of reaction sites may include an assay chamber and a sample chamber; and wherein sample inlets provide sample to the sample chambers and assay inlets provide assay reagents to the assay chambers.

A kit may include an integrated microfluidic device as described herein. For example, the integrated microfluidic device may include: an array of reaction sites; and a plurality of sample processing unit cells may include a plurality of sample processing sites, wherein the unit cell is in fluidic communication with a plurality of different reagent inlets; wherein sample inlets to the array are downstream of the plurality of sample processing sites of the plurality of unit cells. The unit cell of the microfluidic device may include a column configured to retain beads.

The kit further may include a reverse transcriptase, e.g., wherein the reverse transcriptase is in the preamplification mixture. The kit further may include a polymerase, e.g., wherein the polymerase is in the preamplification mixture. The preamplification mixture further may include additional preamplification primer pairs that selectively amplify additional genes.

The kit further may include additional assay mixes that each include a gene-specific primer pair that selectively amplifies one of the additional genes.

The kit further may include a probe that specifically hybridizes to a sequence of the gene conserved across the different alleles (e.g., present in the preamplification mixture or in assay mixes). The probe may include a fluorophore and a quencher (e.g., such as a TakMan probe). The probe may be in the preamplification mixture or in the assay mixes for allele specific qPCR. The kit may further include one or more probes to additional genes to be preamplified and detected by qPCR.

As described herein, the gene may be of a virus, e.g., an RNA virus such as SARS-CoV-2. For example, the alleles may include at least two SARS-CoV-2 spike S1 alleles. The preamplification mixture further may include additional preamplification primer pairs that selectively amplifies additional genes, wherein the additional preamplification primer pairs include a primer pair specific for at the SARS-CoV-2 N1 gene or the SARS-CoV-2 N2 gene.

The kit may further include beads. The beads may be functionalized with one or more single stranded DNA (ssDNA) sequences that specifically hybridize the gene, or antibodies that bind to a biomolecule such as a viral particle. For example, the preamplification mixture further may include additional preamplification primer pairs that selectively amplifies additional genes, and wherein the beads are functionalized with ssDNA sequences that specifically hybridizes each of the additional genes.

Methods and kits of allele detection may be combined with other aspects of the subject application, such as detection of multiple pathogens, serology, sample barcoding, or any other suitable aspect. For example, multiple assays besides allele detection may be performed on the same microfluidic device in parallel (e.g., for the same sample processed in the same unit cell).

For example, sample multiplexing may be increased by mixing samples with beads functionalized with ssDNA to capture target nucleotide sequences (e.g., viral RNA or DNA, mammalian RNA or DNA, or any gene sequence) and beads from different samples may be mixed together. A first extension (e.g., reverse transcription) may be performed before or after mixing the beads together, wherein the ssDNA incorporates a sample barcode. The mixture of beads may then be processed in the same unit cell (e.g., preamplified) and, after splitting into separate reaction sites, a primer specific for the sample barcode may selectively amplify sequences that incorporated the sample barcode. This sample barcoding may be combined with any other aspects of kits and methods described herein. For example, sample barcoding may be used with allele detection such that allele-specific primer pairs include an allele-specific primer and a sample barcode specific primer.

A gene may be any coding sequence for a protein, or subsequence thereof, and may be present in the sample as an RNA or DNA sequence. In certain aspects, any target nucleotide sequence may be analysed (e.g., variants of the target nucleotide sequence may be identified by the methods and kits described herein, such as alleles of a gene).

While examples herein are described for SARS-CoV-2, any viral sample (e.g., influenza, corona virus, HIV, or another RNA virus) or animal alleles (e.g., of a mammal) may be analyzed by the subject methods or kits.

Example of Allele Identification

FIG. 30 shows exemplary use of a dCT threshold to identify presence of an allele. SARS-CoV-2 S1 gene sequences (both wildtype and mutant) were synthesized and mixed at different ratios in a saliva sample, and were analyzed according to the workflow in FIG. 29. The different distributions each correspond to samples having a different mixture (starting from left: 100%, 90%, 50%, 25%, 10%, 5%, 0% mutant to wildtype), The 0% mutant to wildtype (100% wildtype) distribution is to the right of the dCT threshold of 6. The x-axis is the dCT, calculated as the CT of a mutant allele-specific reaction minus the CT of a wildtype allele-specific reactions. A vertical bar is shown for the predetermined dCT threshold (a dCT value of 6 in this example). This threshold could be shifted to the right (e.g., the absolute value of the predetermined threshold could be increased) to achieve higher sensitivity (e.g., to identify presence of a mutant at a lower amount, or a lower % of wildtype). Alternatively, this threshold could be shifted to the left (e.g., the absolute value of the predetermined threshold could be decreased) to achieve higher specificity. A predetermined threshold of more than 3 was found to be suitable to determine the presence of at least 5% mutant for a plurality of different mutants, including single nucleotide polymorphism mutants and deletion mutants of the SARS-CoV-2 S1 gene. Six separate SARS-CoV-2 S1 alleles (5 mutants and 1 wildtype allele) were simultaneously detected for a plurality of samples on the same microfluidic device by the method shown in FIG. 29 and the presence of alleles in different samples identified by the approach shown in FIG. 30.

The invention claimed is:

1. A method of detecting a presence of at least one of a plurality of alleles of a gene in a sample, the method comprising:
    a) preamplifying a gene by PCR to obtain a preamplified sample such that a plurality of alleles of the gene would be amplified by the same preamplification primer pair;
    b) separating the preamplified sample into an array plurality of reaction sites on a microfluidic device; and
    c) detecting a cycle threshold (CT) of each of the plurality of alleles in a separate reaction site of the array of reaction sites, wherein detection is by qPCR, wherein at least two alleles are amplified with a same forward primer, wherein detection is by qPCR wherein each allele is specifically amplified with a different allele-specific reverse primer, wherein qPCR of the alleles in step c) uses a same probe across the array of reaction sites in which different alleles of the gene are detected,
    wherein the microfluidic device comprises: the array of reaction sites; and a plurality of sample processing unit cells, each sample processing unit cell comprising a plurality of sample processing sites,
    wherein each of the plurality of sample processing sites is upstream from and in fluidic communication with a respective sample inlet of a reaction site of the array of reaction sites,
    wherein each of the plurality of sample processing sites is downstream from a cleanup column, wherein the cleanup column is downstream from a unit cell sample inlet,
    wherein each sample processing unit cell further comprises a valve and a pump configured to move flow
    i) downstream from the unit cell sample inlet, through the cleanup column, and to the plurality of sample processing sites, and
    ii) upstream from the plurality of sample processing sites, through the cleanup column, to the unit cell sample inlet, and
    wherein step a) is optionally performed on the microfluidic device.

2. The method of claim 1, wherein individual reaction sites of the array of reaction sites comprise an assay chamber that is in fluid communication with a respective assay inlet to receive assay reagents and a sample chamber that is in fluid communication with the respective sample inlet of the reaction site.

3. The method of claim 1, wherein the cleanup column is configured to retain beads.

4. The method of claim 3, wherein the gene is a viral gene, and further comprising capturing a viral RNA sequence of the gene on the beads through hybridization to a ssDNA sequence prior to step a).

5. The method of claim 4, further comprising eluting the viral RNA sequence and preamplifying the eluted viral RNA sequence to produce a cDNA sequence of the gene prior to step a) of preamplifying.

6. The method of claim 5, further comprising reverse transcribing the viral RNA sequence captured on the beads to produce a cDNA sequence of the gene prior to step a) of preamplifying.

7. The method of claim 3, further comprising capturing viral particles of the sample with antibody conjugated to the beads prior to step a), wherein the gene is a viral gene.

8. The method of claim 1, wherein the gene is a viral gene, the method further comprising reverse transcription of viral RNA to produce a cDNA sequence of the gene prior to step a) of preamplifying.

9. The method of claim 1, wherein the gene is a viral gene, and the sample is a SARS-COV-2 sample.

10. The method of claim 1, wherein one allele has a single nucleotide polymorphism compared to another allele and is amplified in step c) with an allele-specific primer pair that is specific to a point mutation.

11. The method of claim 1, wherein one allele has an insertion or deletion compared to another allele and is amplified in step c) with an allele-specific primer pair that is specific to the insertion or deletion.

12. The method of claim 1, wherein the sample is a biological sample, wherein the biological sample is a blood sample, a saliva, a nasal swab, or derived from a solid tissue.

13. The method of claim 1, further comprising detecting the presence of at least 4 alleles.

14. The method of claim 1, wherein the probe specifically hybridizes to a sequence of the gene conserved across the different alleles.

15. The method of any claim 1, wherein step a) of preamplifying further comprises amplifying additional genes with additional preamplification primer pairs.

16. The method of claim 15, wherein the additional preamplification primer pairs include a primer pair specific for a SARS-COV-2 N1 gene or a SARS-COV-2 N2 gene.

17. The method of claim 1, wherein the alleles include at least two SARS-COV-2 spike S1 alleles.

18. The method of claim 1, wherein at least one allele is amplified in step c) with two allele-specific primers specific for different variant sites of the allele.

19. The method of claim 1, further comprising step d) of identifying the presence of an allele in the sample based on a difference in the CT values (dCT) of the allele and another allele of the plurality of alleles.

20. The method of claim 19, wherein the plurality of alleles comprises at least one wildtype allele and two or more mutant alleles.

21. The method of claim 20, wherein the presence of each of the mutant alleles is identified in step d) based on whether a dCT between the wildtype allele and the mutant allele is above or below a predetermined dCT threshold.

22. The method of claim 21, wherein the predetermined dCT threshold is greater than 3 or less than -3.

23. The method of claim 19, wherein the presence of a mutant allele is identified in step d) and the mutant allele is present at 10% or less of a wildtype allele in the sample.

24. The method of claim 19, further comprising identifying the presence of a virus based on detection of one or more additional genes preamplified in step a) and detected by qPCR in step c).

25. The method of claim 24, further comprising identifying a viral load based on the CT of one or more additional genes preamplified in step a) and detected by qPCR in step c).

26. The method of claim 23, wherein the one or more additional genes comprise at least one of a SARS-COV-2 N1 gene and a SARS-COV-2 N2 gene.

27. The method of claim 19, wherein the CT value of at least one of the alleles of the plurality of alleles is used to report a viral load, wherein the gene is a viral RNA gene.

* * * * *